(12) United States Patent
O'Neil et al.

(10) Patent No.: US 9,689,047 B2
(45) Date of Patent: Jun. 27, 2017

(54) METHODS AND COMPOSITIONS FOR SEQUENCE-SPECIFIC PURIFICATION AND MULTIPLEX ANALYSIS OF NUCLEIC ACIDS

(75) Inventors: Dominic O'Neil, Hilden (DE); Irina Nazarenko, Gaithersburg, MD (US); Holly Basham, Reisterstown, MD (US); Arvind Virmani, Gaithersburg, MD (US); Shiuli Agarwal, Somerville, MA (US); Mridula Shukla, Jersey City, NJ (US)

(73) Assignee: QIAGEN GAITHERSBURG INC., Gaithersburg, MD (US)

( * ) Notice: Subject to any disclaimer, the term of this patent is extended or adjusted under 35 U.S.C. 154(b) by 0 days.

(21) Appl. No.: 13/015,915

(22) Filed: Jan. 28, 2011

(65) Prior Publication Data

US 2011/0217705 A1    Sep. 8, 2011

Related U.S. Application Data

(60) Provisional application No. 61/299,531, filed on Jan. 29, 2010, provisional application No. 61/326,067, filed on Apr. 20, 2010.

(51) Int. Cl.
| | |
|---|---|
| *C12Q 1/68* | (2006.01) |
| *C07H 21/02* | (2006.01) |
| *C07H 21/04* | (2006.01) |
| *C12Q 1/70* | (2006.01) |

(52) U.S. Cl.
CPC .......... *C12Q 1/708* (2013.01); *C12Q 1/6804* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 4,486,536 | A | 12/1984 | Baker et al. |
| 4,486,539 | A | 12/1984 | Ranki et al. |
| 4,563,417 | A | 1/1986 | Albrella et al. |
| 4,563,419 | A | 1/1986 | Ranki et al. |
| 4,689,294 | A | 8/1987 | Boguslawski et al. |
| 4,731,325 | A | 3/1988 | Palva et al. |

(Continued)

FOREIGN PATENT DOCUMENTS

| | | |
|---|---|---|
| CN | 1690223 A | 11/2005 |
| CN | 101177701 A | 5/2008 |

(Continued)

OTHER PUBLICATIONS

De Muro. Medical BioMethods Handbook. 2005. pp. 13-23.*

(Continued)

*Primary Examiner* — Joseph G Dauner
(74) *Attorney, Agent, or Firm* — McBee Moore Woodward & Vanik IP LLC

(57) ABSTRACT

Methods and materials for determining the presence of at least one nucleic acid in a sample are provided, said methods comprising (1) a purification step using sequence specific hybrid capture; (2) an amplification step; and (3) a detection step using two separate sequence-specific polynucleotide probes. Also provided are nucleic acids comprising SEQ ID NO: 1 to SEQ ID NO: 727 and nucleic acid probes and probe sets comprising the same.

7 Claims, 11 Drawing Sheets

(56) References Cited

U.S. PATENT DOCUMENTS

| | | |
|---|---|---|
| 4,732,847 A | 3/1988 | Stuart et al. |
| 4,743,535 A | 5/1988 | Carrico |
| 4,751,177 A | 6/1988 | Stabinsky et al. |
| 4,775,619 A | 10/1988 | Urdea |
| 4,833,084 A | 5/1989 | Carrico |
| 4,851,330 A | 7/1989 | Kohne et al. |
| 4,865,980 A | 9/1989 | Stuart et al. |
| 4,868,105 A | 9/1989 | Urdea et al. |
| 4,889,798 A | 12/1989 | Rabbani |
| 4,894,325 A | 1/1990 | Englehardt et al. |
| 5,082,830 A | 1/1992 | Brakel et al. |
| 5,106,727 A * | 4/1992 | Hartley et al. ............... 435/6.11 |
| 5,116,734 A | 5/1992 | Higgs et al. |
| 5,200,313 A | 4/1993 | Carrico |
| 5,288,611 A | 2/1994 | Kohne et al. |
| 5,374,524 A | 12/1994 | Miller et al. |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,545,806 A | 8/1996 | Lonberg et al. |
| 5,545,807 A | 8/1996 | Surani et al. |
| 5,556,748 A | 9/1996 | Douglas |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,635,352 A | 6/1997 | Urdea et al. |
| 5,641,630 A | 6/1997 | Snitman |
| 5,656,731 A | 8/1997 | Urdea |
| 5,681,697 A | 10/1997 | Urdea et al. |
| 5,681,897 A | 10/1997 | Silvis et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |
| 5,792,606 A | 8/1998 | Deger et al. |
| 5,800,994 A | 9/1998 | Martinelli et al. |
| 5,814,492 A | 9/1998 | Carrino et al. |
| 5,821,339 A | 10/1998 | Schafer et al. |
| 5,827,661 A | 10/1998 | Blais |
| 5,853,993 A | 12/1998 | Dellinger et al. |
| 5,888,724 A | 3/1999 | Silverstein et al. |
| 5,981,179 A | 11/1999 | Lorincz et al. |
| 5,994,079 A | 11/1999 | De La Rosa et al. |
| 6,010,895 A | 1/2000 | Deacon et al. |
| 6,027,897 A | 2/2000 | Lorincz |
| 6,043,038 A | 3/2000 | Sivaraja et al. |
| 6,057,099 A | 5/2000 | Nathan et al. |
| 6,083,925 A | 7/2000 | Li et al. |
| 6,110,676 A | 8/2000 | Coull et al. |
| 6,110,682 A | 8/2000 | Dellinger et al. |
| 6,110,687 A | 8/2000 | Nilsen |
| 6,207,385 B1 | 3/2001 | Stanley |
| 6,221,581 B1 | 4/2001 | Engelhardt et al. |
| 6,225,053 B1 | 5/2001 | Garcia et al. |
| 6,228,578 B1 | 5/2001 | Impraim |
| 6,228,580 B1 | 5/2001 | Blumenfeld et al. |
| 6,232,462 B1 | 5/2001 | Collins et al. |
| 6,268,128 B1 | 7/2001 | Collins et al. |
| 6,277,579 B1 | 8/2001 | Lazar |
| 6,280,954 B1 | 8/2001 | Ulfendahl |
| 6,326,136 B1 | 12/2001 | Lazar et al. |
| 6,355,424 B1 | 3/2002 | Lorincz et al. |
| 6,436,662 B1 | 8/2002 | Mielzynska et al. |
| 6,521,190 B1 | 2/2003 | Edens et al. |
| 6,544,732 B1 | 4/2003 | Chee et al. |
| 6,583,278 B1 | 6/2003 | Carter |
| 6,686,151 B1 | 2/2004 | Lazar et al. |
| 6,828,098 B2 | 12/2004 | Langmore et al. |
| 6,890,729 B2 | 5/2005 | Mielzynska et al. |
| 6,969,585 B2 | 11/2005 | Lorincz et al. |
| 6,977,148 B2 | 12/2005 | Dean et al. |
| 7,001,776 B2 | 2/2006 | Botacini Das Dores et al. |
| 7,138,505 B1 | 11/2006 | Kuo et al. |
| 7,371,518 B2 | 5/2008 | Lorincz et al. |
| 7,439,016 B1 | 10/2008 | Anthony et al. |
| 7,601,497 B2 | 10/2009 | Nazarenko et al. |
| 7,645,571 B2 | 1/2010 | Anthony |
| 7,812,144 B2 | 10/2010 | Karlsen |
| 7,829,691 B2 | 11/2010 | Anthony |
| 8,012,944 B2 | 9/2011 | LaCasse et al. |
| 2001/0053519 A1* | 12/2001 | Fodor et al. ...................... 435/6 |
| 2001/0055766 A1 | 12/2001 | Aristarkhov et al. |
| 2002/0012936 A1 | 1/2002 | Lorincz et al. |
| 2003/0096232 A1 | 5/2003 | Kris et al. |
| 2003/0108897 A1 | 6/2003 | Drmanac |
| 2003/0175765 A1 | 9/2003 | Kessler et al. |
| 2003/0175789 A1 | 9/2003 | Weininger et al. |
| 2004/0180362 A1 | 9/2004 | Lazar et al. |
| 2004/0214302 A1 | 10/2004 | Anthony et al. |
| 2005/0009063 A1 | 1/2005 | Xia et al. |
| 2005/0026976 A1 | 2/2005 | Curtin et al. |
| 2005/0032038 A1 | 2/2005 | Fisher et al. |
| 2005/0032105 A1 | 2/2005 | Bair et al. |
| 2005/0118568 A1* | 6/2005 | Karlsen ........................... 435/5 |
| 2005/0119217 A1 | 6/2005 | LaCasse et al. |
| 2005/0147996 A1 | 7/2005 | Sorge |
| 2005/0272080 A1* | 12/2005 | Palma et al. ...................... 435/6 |
| 2006/0051809 A1 | 3/2006 | Nazarenko et al. |
| 2006/0160188 A1 | 7/2006 | Kurnit et al. |
| 2006/0240449 A1 | 10/2006 | McGlennen et al. |
| 2007/0109898 A1 | 5/2007 | Kasai |
| 2007/0154884 A1 | 7/2007 | Lorincz |
| 2007/0292899 A1 | 12/2007 | Lovell et al. |
| 2008/0200344 A1 | 8/2008 | Cheng |
| 2008/0247914 A1 | 10/2008 | Edens et al. |
| 2009/0032445 A1 | 2/2009 | Doak et al. |
| 2009/0263819 A1 | 10/2009 | Muraca |
| 2009/0286687 A1 | 11/2009 | Dressman et al. |
| 2009/0298187 A1 | 12/2009 | Nazarenko |
| 2010/0036104 A1 | 2/2010 | Nazarenko |
| 2010/0081124 A1 | 4/2010 | Abravaya et al. |
| 2010/0105060 A1 | 4/2010 | Eder |
| 2010/0126286 A1 | 5/2010 | Self et al. |
| 2010/0129789 A1 | 5/2010 | Self et al. |
| 2010/0159463 A1 | 6/2010 | Eder |
| 2010/0216147 A1 | 8/2010 | Upton |
| 2010/0285473 A1 | 11/2010 | Wolff |
| 2010/0311039 A1 | 12/2010 | Fulbright |
| 2011/0003288 A1 | 1/2011 | Anthony |
| 2011/0009277 A1 | 1/2011 | Devos et al. |
| 2011/0059542 A1 | 3/2011 | Anthony |
| 2011/0065906 A1 | 3/2011 | Liu |
| 2011/0196146 A1 | 8/2011 | Khripin |
| 2011/0294111 A1 | 12/2011 | Nazarenko |
| 2012/0004128 A1 | 1/2012 | Mallonee |
| 2012/0021460 A1 | 1/2012 | Lowe |
| 2012/0045756 A1 | 2/2012 | Rothmann |
| 2012/0196274 A1 | 8/2012 | Rangwala |
| 2012/0322049 A1 | 12/2012 | Lowe |
| 2014/0087449 A1 | 3/2014 | Ballhause et al. |

FOREIGN PATENT DOCUMENTS

| | | |
|---|---|---|
| CN | 101351564 A | 1/2009 |
| CN | 101429564 A | 5/2009 |
| EP | 0079139 | 5/1983 |
| EP | 0 163 220 | 12/1985 |
| EP | 0 167 366 | 1/1986 |
| EP | 0184017 | 6/1986 |
| EP | 0 281 927 | 9/1988 |
| EP | 0 288 737 | 11/1988 |
| EP | 0333465 | 9/1989 |
| EP | 0 336 454 | 11/1992 |
| EP | 0 144 914 | 6/1995 |
| EP | 0 415 978 | 3/1996 |

(56) References Cited

FOREIGN PATENT DOCUMENTS

| | | |
|---|---|---|
| EP | 0 703 296 | 3/1996 |
| EP | 1 806 410 A2 | 7/2007 |
| EP | 2 184 368 A1 | 5/2010 |
| JP | H07505759 A | 6/1995 |
| JP | T H-07-505759 A | 6/1995 |
| JP | H08505770 A | 6/1996 |
| JP | 2003529376 A | 10/2003 |
| JP | 200400508019 A | 3/2004 |
| JP | T-2007-509861 A | 4/2007 |
| JP | 2009 106220 | 5/2009 |
| JP | 2009519010 A | 5/2009 |
| JP | 2009291199 A | 12/2009 |
| WO | 84/02721 | 7/1984 |
| WO | 8607387 | 12/1986 |
| WO | 88/03957 | 6/1988 |
| WO | 91/08312 | 6/1991 |
| WO | 93/10263 | 5/1993 |
| WO | 93/10263 A1 | 5/1993 |
| WO | 94/16108 | 7/1994 |
| WO | 94/16108 A1 | 7/1994 |
| WO | 95/16055 | 6/1995 |
| WO | 95/17430 | 6/1995 |
| WO | 96/40992 | 5/1996 |
| WO | 96/40992 | 12/1996 |
| WO | 97/05277 | 2/1997 |
| WO | 97/10364 | 3/1997 |
| WO | 97/31256 | 8/1997 |
| WO | 98/18488 | 5/1998 |
| WO | 98/22620 | 5/1998 |
| WO | 98/59044 | 12/1998 |
| WO | 99/02488 | 1/1999 |
| WO | 99/29909 | 6/1999 |
| WO | WO 9929890 A2 * | 6/1999 |
| WO | 99/32654 | 7/1999 |
| WO | 99/36571 | 7/1999 |
| WO | 99/39001 | 8/1999 |
| WO | 99/40224 | 8/1999 |
| WO | 99/49224 | 9/1999 |
| WO | 99/50459 | 10/1999 |
| WO | 00/60116 | 10/2000 |
| WO | 01/36681 | 5/2001 |
| WO | 0175174 A2 | 10/2001 |
| WO | 0196608 | 12/2001 |
| WO | 02066993 A1 | 8/2002 |
| WO | 2004/087950 | 10/2004 |
| WO | 2005030041 A2 | 4/2005 |
| WO | 2005042030 A1 | 5/2005 |
| WO | 2005/080602 | 9/2005 |
| WO | 2005/088311 A1 | 9/2005 |
| WO | 2006/004365 A1 | 1/2006 |
| WO | 2006039563 A2 | 4/2006 |
| WO | 2006/124771 A2 | 11/2006 |
| WO | 2007/056723 | 5/2007 |
| WO | 2007056723 A2 | 5/2007 |
| WO | 2007100397 A2 | 9/2007 |
| WO | 2007/130519 A2 | 11/2007 |
| WO | 2007134252 A1 | 11/2007 |
| WO | 2008/036061 | 3/2008 |
| WO | 2008/139938 A1 | 11/2008 |
| WO | 2008149237 A2 | 12/2008 |
| WO | 2009/057993 A1 | 5/2009 |
| WO | 2009/123996 | 10/2009 |
| WO | 2009/129404 A1 | 10/2009 |
| WO | 2009/129505 A2 | 10/2009 |
| WO | 2010/004251 A1 | 1/2010 |
| WO | 2010/028382 | 3/2010 |
| WO | 2010/127228 A1 | 11/2010 |

OTHER PUBLICATIONS

GenBank EF422111.1 (Jun. 23, 2008; retrieved on Jul. 3, 2012 from the internet: <url: http://www.ncbi.nlm.nih.gov/nucleotide/148727537?report=genbank&log$=nuclalign&blast_rank=10&RId=Z659FSKS01N>).*

GenBank Y132183.1 (May 20, 1997; retrieved on 73/2012 from the internet: <url: http://www.ncbi.nlm.nih.gov/nucleotide/2113839?report=genbank&log$=nuclalign&blast_rank=14&RId=Z64XMT4C01N>).*

Tondra. J. Vac. Sci. Technol. 2000. 18(4): 1125-1129.*

Sotlar. J. Clin. Microbiol. 2004. 42(7): 3176-3184.*

Buck. Biotechniques. 1999. 27(3): 528-536.*

GenBank 1 (Human papillomavirus type 18 proteins E6 and E7 mRNA, complete cds, and protein E1, 5' end. GenBank: M20325.1. Dec. 6, 1999).*

Naghashfar. J. gen. Virol. 1987. 68: 3073-3079.*

GenBank 2 (Human papillomavirus—18, complete genome. NCBI Reference Sequence: NC_001357.1. Dec. 8, 2008).*

GenBank 3 (Human papillomavirus type 45 isolate Qv31748, complete genome. GenBank: EF202167.1. Dec. 27, 2007).*

Ludwig. Nucleic Acids Research. 2004. 32(4): 1363-1371.*

Buck. Biotechniques .1999. 27(3): 528-536.*

Bosch et al. Journal of the National Cancer Institute Monographs. 2003. 31: 3-13.*

GenBank 4. HPV18 gene sequences, NCBI Reference Sequence: X05015.1.*

GenBank 5. HPV45 genomic DNA, NCBI Reference Sequence: X74479.1.*

GenBank 6. HPV39 complete genome, NCBI Reference Sequence: NC_001535.*

The Random Primer 36 product of NEB Catalog. 1998/1999.*

Rothstein et al. PNAS. 1994. 91:4155-4159.*

Clifford et al. British Journal of Cancer. 2003. 89:101-105.*

Broker et al., "A Molecular Portrait of Human Papillomavirus Carcinogenesis", Cancer Cells. vol. 7 pp. 197-208, 1989 (Roche EU Opposition).

Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).

Karlsen et al., "Use of Multiple PCR Primer Sets for Optimal Detection of Human Papillomavirus", Journal of Clinical Microbiology, pp. 2095-2100, Sep. 1996 (Roche EU Opposition).

Park et al., "Physical Status and Expression of HPV Genes in Cervical Cancers", Gynecologic Oncology, vol. 65, pp. 121-129, 1997 (Roche EU Opposition).

Stoler et al., "Human Papillomavirus Type 16 and 18 Gene Expression in Cervical Neoplasias". Human Pathology, vol. 23, No. 2, pp. 117-128, Feb. 1992 (Roche EU Opposition).

De Villiers et al., "Classification of Papillomaviruses", Virology, vol. 324, pp. 17-27, 2004.

Howley et al. "A Rapid Method for Detecting, and Mapping Homology between Heterologous DNAs", Journal of Biological Chemisny, vol. 254, No. 11, pp. 4879-4883, Jun. 10, 1979.

Law et al., "Conserved Polynucleotide Sequences Among the Genomics of Papillomaviruses", Journal of Virology, vol. 32, No. 1, pp. 199-207, Oct. 1979.

Heilman et al., "Cloning of Human Papilloma Virus Genomic DNAs and Analysis of Homologous Polynucleotide Sequences", Journal of Virology, vol. 36, No. 2, pp. 395-407, Nov. 1980.

Howard et al., "Optimizing the Hybrid Capture II Human Papillomavirus Test to Detect Cervical Intraepithelial Neoplasia", Obstetrics and Gynecology, vol. 100. No. 5, Part 1, pp. 972-980, Nov. 2002.

Lorincz, A.T., "Molecular Methods for the Detection of Human Papillomavirus Infection", Obstetrics and Gynecology Clinics of North America, vol. 23, No. 3, pp. 707-730, Sep. 1996.

B.D. Hames, et al., "Nucleic Acid Hybridization. A Practical Approach." 1985.

Greg T. Hermanson, et al., "Immobilized Affinity Ligand Techniques." 1992.

Richard F. Taylor, "Protein Immobilization. Fundamentals and Applications," 1991.

Blair et al. "Herpes Simplex Virus Viron Stimulatory Protein mRNA Leader Contains Sequence Elements Which Increase Both Virus-Induced Transcription and tnRNA Stability," Journal of Virology, vol. 61, No. 8, pp. 2499-2508, Aug. 1987.

(56) References Cited

OTHER PUBLICATIONS

Larder et al. "Related Functional Domains in Virus DNA Polymerases,"The EMBO Journal. vol. 6, No. 1, pp. 160-175, 1987.
Chandler et al., Detection of Dengue-2 Viral RNA by Reversible Target Capture Flybridization., J. Clin. Microbiol., vol. 31 (10), pp. 2641-2647, 1993.
Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Miorobiol., vol. 37, No. 4, pp. 958-963, 1999.
Murakami et al., Fluorescent-Labeled Oligonucleotide Probes: Detection of Hybrid Formation in Solution by Fluorscence Polarization Spectroscopy, Nucleic Acids Res., vol. 19 (15), pp. 4097-4102, 1991.
Dunn and Hassell: "A Novel Method to Map Transcripts: Evidence for Homology between an Adenovirus niRNA and Discrete Multiple Regions of the Viral Genome" Cell, 12:23-36, Sep. 1977.
Coutlee et al., "Nonisotopic Detection of RNA in an Enzyme Imunoassay using a Monoclonal Antibody Against DNA-RNA Hybrids" Analytical Biochemistry 181:153-162, 1969.
Chen et al., "DNA Optical Sensor: A Rapid Method for the Detection of DNA Hybridization" Biosensors & Bioelectronics 13:451-458, 1998.
Chevrier et al., "Isolation of a Specific DNA fragment and Development of a PCR Based Method for the Detection of *Mycobacterium genavense*" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.
Gelmetti et al., "Detection of Rabbit Haemorrhagic Disease Virus (RHDV) by In Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detecion of *Salmonella* by Using the Calorimetric DNA/rRNA Sandwich Hybrdization in Microtiter Wells" J. Vet. Med. Sci. 62:615-619, 2000.
Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" Mol. Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay" Biol. Chem. 265:11601-11604.
Stollar, B.D. and A. Rashtchian, 1987 "Immunochemicalal Approaches to Gene Probe Assays" Anal. Biochem. 161:387-394.
Blais, B.W., 1994 "Transcriptional Enhancement of the Listeria Monocytogenes PCR and Simple Immunoenzymatic Assay of the Product Using Anti-RNA:DNA Antibodies" Appl. Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbial. 27:120-125.
Boguslawski et al., 1986 "Characterization of Monoclonal Antibody to DNA:RNA and Its Application to Immunodetection of Hybrids" J. Immunol. Methods 89.123-130.

Coutlee et al., 1989 "Immunodetection of DNA with Biotinylated RNA Probes: A Study of Reactivity of Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Calorimetric Fluorescent, and Enzymatic Amplification Substrate Systems in an Enzyme Immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp. 1953-1961.
Goldsborough et al., Nucleotide Sequence of Human Papillomavirus Type 31; A Cervical Neoplasia Associated Virus, Virology, 1989, vol. 171, pp. 306-311.
McGeoch et al., "DNA Sequence and Genetic Content of the Hindlll 1 Region in the Short Unique Component of the Herpes Simplex Virus Type 2 Genome, Identification of the Gene Encoding Glycoprotein G, and Evolutionary Comparisons," J. Gen. Virol., 1987, vol. 68, pp. 19-38.
McGeoch et al., The Complete DNA Sequence of the Long Unique Region in the Genome of Herpes Simplex Virus Type I, 1 Gen Virol., 1988, vol. 69, pp. 1531-1574.
Yamada et al., Human Papillornavirtis Type 16 Variant Lineages in United States Populations Characterized by Nucleotide Sequence Analysis of the E6, L2, and LI Coding Segments, J. Virol., Dec. 1995, vol. 69, No. 12, pp. 7743-7753.
Swain et al., Nucleotide Sequence of the Herpes Simplex Virus Type 2 Thymidine Kinase Gene, Virol., Jun. 1983. vol. 46, No. 3, pp. 1045-1050.
Delius et al., Primer-Directed Sequencing of Human Papillomavirus Types, Current Topics in Microbiolgy and Immunology, 1994, vol. 185, pp. 13-31.
Blair et al., Herpes Simplex Virus Virion Stimulatory Protein mRNA Leader Contains Sequence Elements Which Increase Both Virus-Induced Transcription and mRNA Stability, J. Virol., Aug. 1987, vol. 62, No. 2, pp. 444-453.
Larder et al., Related functional domains in virus DNA polymerases, The EMBO J., 1987, vol. 6, No. 1, pp. 169-175.
McGeoch et al., Structures of Herpes Simplex Virus Type 1 Genes Required for Replication of Virus DNA, J. Virol., vol. 62, No. 2, pp. 444-453.
Zientara et al., 1998 "Use of reverse transcriptase-polymerase chain reaction (RT-PCR) and dot-blot hybridization for the detection and identification of African horse sickness virus nucleic acids" Arch Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycn-Resistant Enterococci in Denmark by Multiplex PCR and Sandwich Hybridization" APMIS 107:404-12.
Sjoroos et al., 1998 "Time-Resolved Fluorometry Based Sandwich Hybridisation Assay for HLA-DQA1 Typing" Disease Markers 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al.,1997 Evaluation of Performances of Three DNA Enzyme Immunoassays for Detection of Helicobacter pylori PCR Products from Biopsy Specimens Journal of Clinical Microbiology, 35:2931-2936.
Chiu et al., 1998 "Sandwich-type Deoxyribonucleic Acid Hybridization Assays Based on Enzyme Amplified Time-Resolved Fluorometry" Analyst , 123:1315-1319.

(56) References Cited

OTHER PUBLICATIONS

White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpurified Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB 1 Locus Using Group-Specific Amplification and SSO-Hybridisation in Microplates" Hereditas 129:161-167.
Chomvarin et al., 2000 "Development of EIA for Detection of Chlamydia Trachomatis in Genital Specimens" The Southeast Asian Journal of Tropical Medicine and Public Health, 31:96-103.
Alexandre et al., 1998 "Quantitative Determination of CMV DNA Using a Combination of Competitive PCR Amplification and Sandwich Hybridization" BioTechniques, 25: 676-683.
Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.
Hara et al., "Small Sample Whole-Genome Amplification," Optics East 2005, UCRL-PROC-216415, Lawrence Livermore National Laboratory, Oct. 21, 2005.
Brigotti, et al., "A rapid and sensitive method to measure the enzymatic activity of ribosome-inactivating proteins," Nucleic Acids Res., vol. 26, No. 18, pp. 4306-4307, 1998.
PCT/US2009/062061, International Searching Authority, Oct. 26, 2009 (6 pages).
PCT/US2009/062041, International Searching Authority, Oct. 26, 2009 (5 pages).
Bart "General Principles of Immunoprecipitation," Jul. 31, 2008 (XP002560372).
Bhan et al., "2',5'-Linked oligo-3'-deoxyribonucleoside phosphorothioate chimeras: thermal stability and antisense inhibition of gene expression," Nucleic Acids Research, 1997, vol. 25, No. 16, pp. 3310-3317 (XP-002560367).
Genetech Diagnostics Pvt. Ltd., "Digene HBV Test Hybrid Capture II," Jun. 6, 2008 (XP-002560368).
Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp, 29-35 (XP002560369).
Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).
Boston Bioproduct Inc., "Protein Extraction buffers," Sep. 2, 2007 (XP002560371).
Mittendorf T, et al., "HPV-DNA-Diagnostik zur Zervixkarzinomfrüherkennung; Deutsche Agentur füHTA des Deutschen Instituts für Medizinische Dokumentation und Information," 1. Auflage 2007.

Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.
Davey DD, et al., "introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic Issues for Cervical Cancer Prevention in Low-Resource Settings," Path, Dec. 2000.
Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031, Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S. et al., "The Predominant mRNA Class in HPV16-Infected Genital Neoplasias does not Encode the E6 or the E7 Protein," Int. J. Cancer; 55, 791-798 (1993).
Middleton, K, et al., "Organization of Human Papillomavirus Productive Cycle during Neoplastic Progression Provides a Basis for Selection of Diagnostic markers." Journal of Virology, Oct. 2003, pp. 10186-10201.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517, see the whole document.
GenBank Accession No. AB027021, "Human papillomavirus type 82 DNA, complete genome.", Jun. 22, 2000. See http://www.ncbi.nlm.nih.gov/nuccore/6970427.
GenBank Accession No. X67161, "Human papillomavirus type L1 gene for major capsid protein.", Apr. 18, 2005, See http://www.ncbi.nlm.nih.gov/nuccore/1197494.
Park, JS, et al., "Physical Status and Expression of HPV Genes in Cervical Cancers,"Gynec. Oncol. 95 (1997), pp. 121-129.
GenBank Accession No. U31794, "Human papillomavirus type 66, complete genome.", Oct. 18, 1995. See http://www.ncbi.nlm.nih.gov/nuccore/1020290.
Letter dated Jan. 6, 2010 to EPO re EP 1 038 122 (46 pages).
Letter to EPO dated Mar. 2, 209 re EP 1 038 022 (15 pages).
Letter to EPO dated Oct. 6, 2008 re EP 1 038 033 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062041, mail date Jan. 5, 2010.
Partial International Search Report for PCT/US2009/062041, mail date Apr. 8, 2010.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I) Poly(dC) as Immunogens for the Induction of Antibodies to RNA-DNA Hybrids," Molecular Immunology, vol. 19, No. 3, pp. 413-420, 1962.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.

(56) References Cited

OTHER PUBLICATIONS

Jakobovits et al., "Germ-line transmission and expression of a human-derived yeast artificial chromosome," pp. 255-258, Nature, vol. 362, Mar. 18, 1993.
International Search Report for PCT/US2009/041033, dated Dec. 22, 2009.
Sigurdsson et al., "Human papillomavirus (HPV) in an Icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al,, "Classification of papillomarviruses," In: Virology, Jun. 2004; vol. 324(1), pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "human papillomavirus type 45 genomic DNA.", Apr. 18, 2005. See http://www.ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002 See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome.", Apr. 18, 2005. See http://www.ncbi.nlm.nih.gov/nuccore/557236.
Supplementary European Search Report of PCT/US2006/060603, dated Jul. 7, 2010 (8 pages).
Lowe, et al., "A computer program for selection of oligonucleotide primers for polymerase chain reactions". Nucleic Acid Res., vol. 18, No. 7, pp. 1757-1761 (1990).
International Search Report and Written Opinion of PCT/US2010/022264 dated Jun. 7, 2010 (19 pages).
Cohenford et al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit," (Jun. 6, 2008), XP002578832, Retrieved from the Internet: URL: http://www.gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.
Darwin et al., "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6.
Vernick et el., "The HPV DNA virus hybrid capture assay; What is it—and where do we go from here?" MLO Med. Lab. Obs., (Mar. 2003), pp. 8-10, 13, vol. 35, No. 3.
International Search Report and Written Opinion of PCT/US2010/048714, dated Dec. 10, 2010 (14 pages).
International Preliminary Report on Patentability and Written Opinion of PCT/US2009/041033 dated Oct. 19, 2010 (6 pages).
International Search Report and Written Opinion PCT/US2010/047769, dated Nov. 9. 2010 (11 pages).
Pachowics, et al., "Sequence specific large volume sample prep solution utilizing Hybrid Capture technology," 41st Annual Oak Ridge Conference; Baltimore, MD; Apr. 16, 2009, retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Scence, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.
Partial European Search Report of EP10185824; mailed Feb. 16, 2011 (8 pages).

(56) References Cited

OTHER PUBLICATIONS

Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.
Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.
International Search Report and Written Opinion of PCT/US2011/22887, dated Jun. 1, 2011.
International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: <URL:http://www.ncbi.nlm.nih.gov/nuccore/FJ429103.1>]; in entirety.
Lowe et al.; "A Hybrid-Capture Assay to Detect HPV MRNA Ratios in Cervical Specimens"; Journal of Virological Methods; vol. 179; No. 1; Jan. 2012; pp. 142-147.
International Search Report Based on Application No. PCT/US2012/026380 Mailed Oct. 15, 2012.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 2004, pp. 209-217; XP001538494.
International Search Report and Written Opinion based on PCT/US2001/037012 mailed Apr. 17, 2012.
International Search Report Based on Application No. PCT/US2012/020684 Mailed Oct. 25, 2012.
Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD-PUBMED:21191046; vol. 49; No. 3; Dec. 29, 2010; pp. 1071-1076; Abstract.
Li et al; Detection of Human Paillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.
Han et al.; "Simultaneous Amplification and Identification of 25 Human Papillomavirus Types With Templex Technology"; Journal of Clinical Microbiology 200611 US LNKD- DOI:10.1128/JCM.01762-06; vol. 44; No. 11; Nov. 2006; pp.4157-4162; Abstract.
Database EMBL [Online]; Jul. 19, 2007; "Sequence 25 From Patent EP1806410"; XP002675256; Retrieved From EBI Accession No. EMBL:CS642417; Database Accession No. CS642417; The Whole Document.
Database EMBL [Online]; Dec. 14, 2010; "Sequence 26 From Patent US 7812144"; XP00267527; Retrieved from EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.
Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.
Database Geneseq [Online]; Apr. 1, 2010; "HPV16 E7 Gene Forward RT-PCR Primer Seq ID 49"; XP002675260; Retrieved From EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, Seq ID No. 37"; XP002675261; Retrieved From EBI Accession No. GSN:ADX15568; Database Accession No. ADX15568; Sequence.
Database Geneseq [Online] Jan. 11, 2007, "Human papillomavirus (HPV) PCR primer SEQ ID No. 49," XP002716503, retrieved from EBI accession No. GSN:AEM05072 & KR 2006 0005089 A Jan. 17, 2006 (category Y).
Database EMBL [Online] Feb. 19, 2007, "Human papillomavirus type 2 isolate C1, complete genome," XP002716507, retrieved from EBI accession No. EM_STD:EF362755 (category Y).
Database EMBL [Online] Oct. 5, 2007, "Human papillomavirus type 2 isolate CN-SC1, complete genome," XP002716504, retrieved from EBI accession No. EM_STD:EF117890 (category Y).
Database EMBL [Online] Feb. 18, 1991, "Human papilloma virus type 2a complete DNA," XP002716505, retrieved from EBI accession No. EM_STD:X55964 (category Y).
Database EMBL [Online] Feb. 19, 2007, "Human papillomavirus type 2 isolate C2, complete genome," XP002716506, retrieved from EBI accession No. EM_STD:EF362754 (category Y).
Yan-Jun Lei et al: "HPV-2 Isolates from Patients with Huge Verrucae Vulgaris Possess Stronger Promoter Activities," Intervirology, vol. 50, No. 5, Jan. 1, 2007 (Jan. 1, 2007), pp. 353-360, XP055088346 (category Y).
Wang et al: "Detection of HPV-2 and identification of novel mutations by whole genome sequencing from biopsies of two patients with multiple cutaneous horns," Journal of Clinical Virology, vol. 39, No. 1, Apr. 17, 2007 (Apr. 17, 2007), pp. 34-42, XP022032678 (category Y).
Hirsch-Behnam A et al: "A comparative sequence analysis of two human papillomavirus (HPV) types 2a and 57, " Virus Research, vol. 18, No. 1, Dec. 1, 1990, pp. 81-97, XP023887424 (category Y).
Chinese First Action dated Apr. 26, 2013, issued in Application No. 201180012414.0 and English translation thereof.
Chinese Office Action (Second) issued in Application No. 200980143682.9, dated Aug. 5, 2013, and English translation thereof.
Instructions RIPA Buffer (No. 89900 89901) [online] Thermo Scientific, 2006, [<Retrieved from the Internet: http://www.piercenet.com/instructions/2161782.pdf>].
Japanese Notice of Reasons for Rejection dated Nov. 27, 2013, issued in Application No. 2011-533405 and English translation thereof.
Notice of Reasons for Rejection dated Aug. 26, 2013, issued in Japanese Application No. 2011-505244 and English translation thereof.
International Preliminary Report on Patentability dated Aug. 27, 2013, issued in Application No. PCT/US2012/026380.
Chinese First Action dated Aug. 2, 2013, issued in Application No. 201180016276.3 and English translation thereof.
Molijin A. et al., "Molecular diagnosis of human papillomavirus (HPV) infections," Journal of Clinical Virology, 2005, Vo. 32S at pp. S43-S51.
Chinese First Action dated Apr. 15, 2013, issued in Application No. 201080018737.6.
European Office Action dated Oct. 18, 2013, issued in Application No. 11 726 003.4-1403.
Rychlik et al., A computer program for choosing optimal oligonucleotides for filter hybridization, sequence and in vitro amplification of DNA. Nucleic Acids Research, 17, 8543-8551, 1989.
Australian Patent Examination Report No. 1, dated Oct. 24, 2013, issued for Application No. 2009238247.
Huang SL et al., Comparison between the Hybrid Capture II Test and an SPF1/GP6+ PCR-based assay for detection of human papillomavirus DNA in cervical swab samples. J. Clin Microbiol. 2006, 44(5):1733-9.
European Search Report issued in Application No. 11737712.7-1404/2528932 PCT/US2011022887, dated Dec. 6, 2013.

(56) References Cited

OTHER PUBLICATIONS

International Search Report based on PCT/US2011/22887 mailed Apr. 17, 2011.
International Preliminary Report on Patentability based on PCT/US2011/22887 mailed Jun. 1, 2011.
Luo et al., "Adiponectin stimulates human osteoblasts proliferation and differentiation via the MAPK signaling pathway," Experimental Cell Research, Academic Press, US, 309:1, (Sep. 10, 2005) 99-109, XP005037411.
Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.
Scholz et al., "Analysis of human immunodeficieny virus matrix domain replacements," Virology, Elsevier, Amsterdam, NL. 371:2, (Nov. 8, 2007) 322-335, XP022439785.
Xie H. et al., "Apelin in and its receptor are expressed in human obsteoblasts," Regulatory Peptides, Elsevier Science B.V., NL, 134: 2-3, (May 15, 2006), 118-125, XP27895144.
Zhang W. et al., "Bone-Targeted Overexpression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.
European Office Action dated Jul. 14, 2014, issued in Application No. 10 755 291.1-1406.
Yu N. et al., "D3-Human papillomavirus type 16 isolate b00721 E6 (E6) and E7 (E7) genes,—Nucleotide—NCBI, Accession: FJ429103.1." GenBank Database. Nov. 1, 2009.
Chinese First Office Action dated Feb. 20, 2014, issued in Application No. 201180015544.X English translation thereof.
Chinese Search Report/First Office Action dated Feb. 11, 2014, issued in Application No. 20118001554.X. No English Translation provided.
European Office Action dated Jul. 4, 2014, issued in Application No. 09 752 940.8-1403.
Japanese Office Action dated Jun. 30, 2014, issued in Application No. 2011-548258.
Chinese Office Action dated May 4, 2014, issued in Application No. 200980143682.9, English translation.
Coutlee et al., "Nonisotopic Detection of RNA in an Enzyme Immunoassay Using a Monoclonal Antibody against DNA-RNA Hybrids." Analytical Biochemistry 181, 153-162 (1989).
Saxtre-Garau X et al., "Human papillomavirus type 45, E6 and E7 genes" Gene Bank Databse, Accession No. Y13218.1. http://www.ncbi.nlm.nih.gov/nuccore/Y13218.1. 1997.
Villiers et al., "Classification of papillomaviruses" Virology. vol. 324: 17-27, (2004).

\* cited by examiner

FIG. 2

Detection of quadruple infections in 20-Plex

| Types | Input | 6 | 11 | 16 | 18 | 31 | 33 | 45 | 34 | 35 | 52 | 53 | 58 | 59 | 66 | 67 | 68 | 69 | 70 | 73 | 82 |
|---|---|---|---|---|---|---|---|---|---|---|---|---|---|---|---|---|---|---|---|---|---|
| 6, 11, 16, 18 | 10^7 | 108 | 1202 | 606 | 1600 | 65 | 37 | 44 | 58 | 60 | 46 | 97 | 57 | 37 | 101 | 69 | 53 | 66 | 73 | 69 | 82 |
|  | 10^6 | 67 | 1428 | 787 | 1605 | 71 | 56 | 31 | 75 | 63 | 66 | 147 | 76 | 96 | 107 | 67 | 61 | 72 | 69 | 75 | 46 |
|  | 10^5 | 670 | 1280 | 700 | 1720 | 84 | 48 | 54 | 86 | 44 | 65 | 117 | 56 | 61 | 113 | 64 | 83 | 93 | 39 | 58 | 69 |
|  | 10^4 | 610 | 770 | 1037 | 2007 | 67 | 81 | 83 | 88 | 81 | 71 | 166 | 94 | 96 | 120 | 83 | 85 | 95 | 47 | 62 | 39 |
|  | 10^3 | 777 | 770 | 772 | 1618 | 71 | 81 | 74 | 86 | 54 | 54 | 109 | 76 | 73 | 102 | 64 | 100 | 74 | 37 | 51 | 82 |
|  | 10^2 | 830 | 830 | 710 | 1609 | 95 | 59 | 85 | 84 | 41 | 103 | 138 | 56 | 74 | 80 | 44 | 96 | 56 | 64 | 56 | 70 |
| 31, 33, 34, 45 | 10^7 | 52 | 47 | 38 | 66 | 109 | 604 | 646 | 1108 | 43 | 52 | 94 | 47 | 50 | 49 | 50 | 35 | 57 | 45 | 44 | 57 |
|  | 10^6 | 55 | 39 | 44 | 75 | 402 | 717 | 816 | 1863 | 48 | 59 | 87 | 44 | 38 | 70 | 62 | 50 | 51 | 42 | 45 | 44 |
|  | 10^5 | 34 | 41 | 51 | 57 | 493 | 550 | 570 | 2098 | 51 | 32 | 95 | 22 | 43 | 56 | 48 | 53 | 70 | 44 | 41 | 36 |
|  | 10^4 | 39 | 36 | 53 | 76 | 599 | 652 | 650 | 2177 | 43 | 40 | 79 | 44 | 63 | 87 | 50 | 36 | 38 | 52 | 46 | 49 |
|  | 10^3 | 45 | 32 | 37 | 49 | 507 | 559 | 583 | 2050 | 42 | 54 | 91 | 44 | 47 | 106 | 54 | 50 | 51 | 51 | 53 | 57 |
|  | 10^2 | 39 | 51 | 58 | 54 | 95 | 59 | 85 | 1070 | 46 | 60 | 112 | 51 | 50 | 79 | 61 | 76 | 64 | 36 | 54 | 56 |
| 35, 52, 53, 58 | 10^7 | 72 | 67 | 49 | 59 | 51 | 40 | 68 | 58 | 144 | 1062 | 335 | 210 | 42 | 87 | 60 | 44 | 70 | 48 | 53 | 63 |
|  | 10^6 | 39 | 44 | 56 | 47 | 39 | 51 | 43 | 33 | 945 | 330 | 458 | 210 | 57 | 51 | 54 | 30 | 46 | 48 | 36 | 50 |
|  | 10^5 | 62 | 49 | 58 | 50 | 47 | 32 | 42 | 47 | 574 | 164 | 517 | 372 | 70 | 56 | 51 | 60 | 54 | 26 | 48 | 54 |
|  | 10^4 | 46 | 36 | 76 | 62 | 60 | 30 | 35 | 68 | 716 | 248 | 865 | 411 | 56 | 87 | 55 | 64 | 67 | 43 | 50 | 65 |
|  | 10^3 | 68 | 38 | 47 | 49 | 48 | 37 | 27 | 34 | 901 | 679 | 800 | 327 | 44 | 81 | 52 | 53 | 60 | 43 | 48 | 57 |
|  | 10^2 | 50 | 62 | 61 | 50 | 43 | 34 | 28 | 52 | 506 | 180 | 365 | 124 | 56 | 63 | 48 | 35 | 62 | 36 | 27 | 49 |
| 59, 66, 67, 68 | 10^7 | 46 | 27 | 53 | 52 | 37 | 46 | 45 | 29 | 24 | 40 | 72 | 59 | 41 | 174 | 60 | 250 | 42 | 56 | 54 | 31 |
|  | 10^6 | 34 | 38 | 54 | 58 | 44 | 34 | 44 | 22 | 33 | 29 | 57 | 41 | 70 | 164 | 54 | 194 | 54 | 58 | 46 | 47 |
|  | 10^5 | 34 | 57 | 58 | 75 | 45 | 32 | 34 | 42 | 51 | 48 | 83 | 48 | 44 | 216 | 51 | 310 | 43 | 36 | 40 | 58 |
|  | 10^4 | 40 | 34 | 67 | 40 | 63 | 45 | 63 | 52 | 31 | 38 | 92 | 40 | 43 | 230 | 55 | 419 | 60 | 37 | 58 | 54 |
|  | 10^3 | 53 | 49 | 51 | 77 | 37 | 49 | 55 | 47 | 61 | 49 | 99 | 59 | 46 | 81 | 52 | 130 | 65 | 37 | 32 | 34 |
|  | 10^2 | 42 | 45 | 60 | 74 | 52 | 51 | 34 | 37 | 38 | 46 | 86 | 46 | 56 | 63 | 48 | 250 | 74 | 47 | 60 | 53 |
| 69, 70, 73, 82 | 10^7 | 47 | 39 | 35 | 44 | 48 | 21 | 38 | 58 | 53 | 53 | 57 | 34 | 41 | 48 | 57 | 35 | 109 | 149 | 196 | 149 |
|  | 10^6 | 57 | 37 | 64 | 63 | 44 | 36 | 52 | 47 | 64 | 43 | 50 | 50 | 70 | 61 | 41 | 46 | 220 | 183 | 537 | 175 |
|  | 10^5 | 36 | 33 | 52 | 49 | 39 | 36 | 40 | 34 | 34 | 36 | 68 | 49 | 44 | 72 | 54 | 37 | 255 | 205 | 749 | 403 |
|  | 10^4 | 49 | 73 | 51 | 70 | 55 | 59 | 54 | 40 | 65 | 44 | 83 | 63 | 43 | 74 | 75 | 51 | 301 | 165 | 660 | 270 |
|  | 10^3 | 55 | 47 | 70 | 48 | 68 | 34 | 26 | 48 | 34 | 59 | 101 | 51 | 46 | 65 | 55 | 48 | 677 | 358 | 814 | 630 |
|  | 10^2 | 35 | 58 | 27 | 63 | 34 | 83 | 41 | 53 | 68 | 41 | 72 | 56 | 46 | 59 | 46 | 58 | 398 | 239 | 220 | 210 |

FIGURE 6

| | 6 | 11 | 16 | 18 | 26 | 31 | 33 | 34 | 35 | 39 | 45 | 51 | 52 | 53 | 54 | 58 | 56 | 59 | 66 | 67 | 68 | 69 | 70 | 73 | 82 | 85 |
|---|---|---|---|---|---|---|---|---|---|---|---|---|---|---|---|---|---|---|---|---|---|---|---|---|---|---|
| HPV6 | 15.2 | 1.1 | 1.2 | 1.2 | 1.0 | 1.2 | 1.1 | 1.1 | 1.1 | 1.2 | 1.0 | 1.2 | 1.1 | 1.2 | 1.3 | 1.1 | 1.0 | 1.3 | 1.0 | 1.2 | 1.1 | 1.1 | 1.2 | 1.1 | 1.2 | 1.2 |
| HPV11 | 1.1 | 12.8 | 1.2 | 0.9 | 0.8 | 1.8 | 0.6 | 0.6 | 1.0 | 1.2 | 0.7 | 0.7 | 0.8 | 1.2 | 1.2 | 0.7 | 0.6 | 0.6 | 1.0 | 0.5 | 0.6 | 0.7 | 0.6 | 0.7 | 0.5 | 1.1 |
| HPV16 | 1.1 | 1.3 | 19.4 | 1.2 | 1.4 | 1.2 | 1.2 | 1.2 | 1.1 | 0.8 | 1.1 | 1.2 | 1.2 | 1.3 | 1.1 | 1.2 | 1.1 | 1.3 | 1.1 | 1.2 | 1.1 | 1.1 | 1.2 | 1.2 | 1.1 | 0.9 |
| HPV18 | 1.3 | 1.2 | 1.3 | 50.0 | 1.2 | 1.2 | 1.3 | 1.4 | 1.3 | 1.3 | 1.2 | 1.2 | 1.2 | 1.6 | 1.5 | 1.2 | 1.2 | 1.4 | 1.1 | 2.4 | 1.3 | 1.2 | 1.3 | 1.2 | 1.1 | 1.7 |
| HPV26 | 0.9 | 0.8 | 1.3 | 0.9 | 15.2 | 0.8 | 1.3 | 0.5 | 0.9 | 1.3 | 0.9 | 0.9 | 0.3 | 1.1 | 1.0 | 0.7 | 0.6 | 0.9 | 1.2 | 0.5 | 0.6 | 0.8 | 0.8 | 0.8 | 0.5 | 0.9 |
| HPV31 | 0.8 | 0.9 | 1.1 | 0.8 | 0.6 | 26.9 | 0.8 | 0.6 | 0.9 | 0.8 | 0.6 | 1.2 | 0.7 | 1.4 | 1.2 | 0.9 | 1.3 | 0.6 | 1.3 | 0.6 | 0.8 | 0.8 | 0.8 | 0.8 | 0.5 | 0.9 |
| HPV33 | 1.2 | 1.2 | 1.2 | 1.2 | 1.2 | 1.3 | 19.9 | 1.3 | 1.7 | 1.2 | 1.2 | 1.2 | 1.3 | 1.5 | 1.4 | 1.2 | 1.3 | 1.4 | 1.2 | 1.4 | 1.3 | 1.2 | 1.3 | 1.3 | 1.3 | 1.0 |
| HPV34 | 1.2 | 1.5 | 1.3 | 1.3 | 1.2 | 1.3 | 1.2 | 14.8 | 1.2 | 1.2 | 1.2 | 1.3 | 1.3 | 1.5 | 1.4 | 1.3 | 1.2 | 1.4 | 1.1 | 1.3 | 1.2 | 1.2 | 1.4 | 1.3 | 1.4 | 1.3 |
| HPV35 | 1.3 | 1.7 | 1.3 | 1.4 | 1.2 | 1.4 | 1.3 | 2.3 | 18.1 | 1.3 | 1.3 | 1.5 | 1.3 | 1.6 | 1.4 | 1.8 | 1.2 | 1.4 | 1.2 | 1.4 | 1.3 | 1.3 | 1.4 | 1.4 | 1.4 | 1.2 |
| HPV39 | 1.2 | 2.2 | 1.3 | 1.3 | 1.2 | 1.3 | 1.3 | 1.4 | 1.3 | 21.3 | 1.3 | 1.4 | 1.3 | 1.5 | 1.4 | 1.2 | 1.2 | 1.5 | 1.2 | 1.3 | 1.3 | 1.2 | 1.4 | 1.3 | 1.4 | 1.2 |
| HPV45 | 1.3 | 1.3 | 1.3 | 1.4 | 1.3 | 1.4 | 1.4 | 1.3 | 1.3 | 1.3 | 37.3 | 1.4 | 1.3 | 1.5 | 1.4 | 1.3 | 1.2 | 1.3 | 1.2 | 1.3 | 1.3 | 1.2 | 1.4 | 1.4 | 1.4 | 1.1 |
| HPV51 | 1.1 | 1.1 | 0.7 | 1.2 | 1.0 | 1.1 | 0.9 | 0.7 | 0.9 | 1.2 | 1.0 | 11.2 | 1.0 | 1.2 | 1.1 | 1.0 | 0.7 | 0.9 | 1.1 | 0.9 | 1.0 | 0.7 | 0.7 | 0.7 | 1.3 | 1.1 |
| HPV52 | 1.2 | 1.6 | 1.4 | 1.6 | 1.2 | 1.3 | 1.3 | 1.3 | 1.3 | 1.3 | 1.2 | 1.5 | 20.2 | 1.3 | 1.4 | 1.3 | 1.3 | 1.4 | 1.2 | 1.2 | 1.3 | 1.3 | 1.4 | 1.4 | 1.4 | 1.1 |
| HPV53 | 1.3 | 1.3 | 2.0 | 1.4 | 1.1 | 1.4 | 1.4 | 1.3 | 1.3 | 1.4 | 1.2 | 1.4 | 1.3 | 21.4 | 1.4 | 1.3 | 1.2 | 1.5 | 1.2 | 1.3 | 1.3 | 1.3 | 1.4 | 1.3 | 1.4 | 1.1 |
| HPV54 | 1.4 | 1.3 | 1.3 | 1.4 | 1.3 | 1.4 | 1.3 | 1.4 | 1.3 | 1.4 | 1.3 | 1.4 | 1.4 | 1.5 | 21.8 | 1.3 | 1.2 | 1.4 | 1.2 | 1.3 | 1.3 | 1.3 | 1.5 | 1.4 | 1.4 | 1.1 |
| HPV56 | 1.2 | 0.9 | 1.0 | 1.0 | 1.0 | 1.1 | 0.6 | 0.8 | 1.2 | 0.7 | 1.1 | 1.3 | 0.8 | 1.0 | 1.3 | 22.1 | 0.7 | 0.9 | 0.6 | 0.7 | 0.6 | 0.7 | 0.7 | 0.7 | 0.8 | 0.7 |
| HPV58 | 1.4 | 1.5 | 1.4 | 1.6 | 1.3 | 1.4 | 1.4 | 1.4 | 1.4 | 1.3 | 1.3 | 1.4 | 1.4 | 1.6 | 1.4 | 1.4 | 20.8 | 1.5 | 1.3 | 1.6 | 1.3 | 1.3 | 1.4 | 1.4 | 1.4 | 0.9 |
| HPV59 | 1.0 | 1.0 | 1.1 | 1.1 | 1.3 | 1.1 | 1.3 | 1.3 | 1.0 | 1.3 | 1.1 | 1.3 | 1.3 | 1.3 | 1.1 | 1.0 | 1.2 | 23.0 | 1.0 | 2.1 | 1.1 | 1.3 | 1.4 | 1.1 | 1.1 | 1.1 |
| HPV66 | 1.6 | 1.9 | 1.6 | 1.7 | 1.6 | 1.7 | 1.8 | 1.7 | 1.6 | 1.5 | 1.5 | 1.7 | 1.7 | 1.7 | 1.6 | 2.1 | 1.6 | 1.7 | 10.6 | 1.9 | 1.6 | 1.6 | 1.8 | 1.6 | 2.0 | 1.0 |
| HPV67 | 0.8 | 1.2 | 0.7 | 0.7 | 0.9 | 0.6 | 0.8 | 0.8 | 0.9 | 0.8 | 0.9 | 0.6 | 0.9 | 1.1 | 1.2 | 0.8 | 0.6 | 0.5 | 0.8 | 7.0 | 0.8 | 0.7 | 0.8 | 0.8 | 0.6 | 0.9 |
| HPV68 | 1.3 | 1.3 | 1.4 | 1.6 | 1.4 | 1.5 | 1.4 | 1.5 | 1.4 | 1.4 | 1.4 | 1.5 | 1.4 | 1.6 | 1.5 | 1.3 | 1.3 | 1.7 | 1.4 | 1.8 | 24.1 | 1.3 | 1.5 | 1.5 | 1.1 | 1.2 |
| HPV69 | 1.0 | 1.1 | 1.1 | 1.2 | 1.2 | 1.1 | 1.2 | 1.1 | 1.1 | 1.1 | 1.1 | 1.1 | 1.2 | 1.4 | 1.3 | 1.5 | 1.0 | 1.2 | 1.0 | 1.9 | 1.3 | 7.6 | 1.2 | 1.2 | 1.5 | 1.1 |
| HPV70 | 1.2 | 1.3 | 1.7 | 1.2 | 1.2 | 1.0 | 1.1 | 0.7 | 0.6 | 1.1 | 1.0 | 0.8 | 0.9 | 1.0 | 1.2 | 1.0 | 0.6 | 1.0 | 0.6 | 0.7 | 1.0 | 1.0 | 22.2 | 0.8 | 0.8 | 0.9 |
| HPV73 | 1.2 | 1.1 | 0.8 | 0.9 | 0.9 | 1.0 | 0.5 | 0.9 | 0.9 | 0.9 | 0.9 | 0.8 | 0.9 | 0.9 | 1.0 | 1.0 | 1.0 | 1.0 | 1.2 | 0.6 | 0.7 | 0.9 | 0.7 | 8.8 | 0.8 | 1.0 |
| HPV82 | 0.9 | 0.8 | 1.1 | 1.1 | 1.0 | 1.0 | 1.1 | 1.1 | 1.0 | 1.1 | 1.0 | 1.0 | 1.1 | 1.3 | 1.2 | 0.8 | 0.8 | 1.1 | 0.9 | 1.8 | 0.9 | 1.0 | 1.0 | 1.8 | 4.8 | 1.0 |
| HPV85 | 0.9 | 0.9 | 0.9 | 1.0 | 0.8 | 0.9 | 1.1 | 1.0 | 1.0 | 0.9 | 0.8 | 1.0 | 1.0 | 1.3 | 1.2 | 0.8 | 0.8 | 1.1 | 0.9 | 1.2 | 1.0 | 0.9 | 1.0 | 1.0 | 1.5 | 7.7 |

SEQUENCE LISTING

```
<160> NUMBER OF SEQ ID NOS: 726

<210> SEQ ID NO 1
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 1
aaccgaaacc gguuaguaua aaagc                                          25

<210> SEQ ID NO 2
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 2
uuagaaugug uguacugcaa gcaac                                          25

<210> SEQ ID NO 3
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 3
gguauaugac uuugcuuuuc gggau                                          25

<210> SEQ ID NO 4
<211> LENGTH: 25
<212> TYPE: RNA
```

```
<213> ORGANISM: Artificial Sequence
<220> FEATURE:
<223> OTHER INFORMATION: Nucleic acid probe

<400> SEQUENCE: 4
aguauauaga gaugggaauc cauau                                            25

<210> SEQ ID NO 5
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 5
acaacaaacc guugugugau uuguu                                            25

<210> SEQ ID NO 6
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 6
uuagguguau uaacugucaa aagcc                                            25

<210> SEQ ID NO 7
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 7
gauuccauaa uauaagggu cggug                                             25

<210> SEQ ID NO 8
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 8
auguugcacg cacaaacaua uauua                                            25

<210> SEQ ID NO 9
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 9
guuccuaaag uaucaggauu acaau                                            25

<210> SEQ ID NO 10
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 10
ucccuauuuu ccuauuaaaa aaccu                                            25
```

```
<210> SEQ ID NO 11
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 11
guuugggccu guguaggugu ugagg                                         25

<210> SEQ ID NO 12
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 12
gucagccauu aggugugggc auuag                                         25

<210> SEQ ID NO 13
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 13
uguguuuaau ugguugcaaa ccacc                                         25

<210> SEQ ID NO 14
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 14
ggugauuguc caccauuaga guuaa                                         25

<210> SEQ ID NO 15
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 15
caguuauuca ggauggugau auggu                                         25

<210> SEQ ID NO 16
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 16
gaaauccuuu uucucaagga cgugg                                         25

<210> SEQ ID NO 17
<211> LENGTH: 25
<212> TYPE: RNA
<213> ORGANISM: Artificial Sequence
<220> FEATURE:
```

<223> OTHER INFORMATION: Nucleic acid probe

<400> SEQUENCE: 17
caauguguag acauuauaaa cgagc                                           25

<210> SEQ ID NO 18
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 18
uuagacauuu auuuaauagg gcugg                                           25

<210> SEQ ID NO 19
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 19
cauaugauaa uccugcauau gaagg                                           25

<210> SEQ ID NO 20
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 20
aauaugauuu acaguuuauu uuuca                                           25

<210> SEQ ID NO 21
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 21
auccuuuauu aaauaaauug gauga                                           25

<210> SEQ ID NO 22
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 22
cuauuaguac acauaauuau gaaga                                           25

<210> SEQ ID NO 23
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 23
gguacaaugg gcauaugaca augau                                           25

```
<210> SEQ ID NO 24
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 24
gacaaacagu auuacagcau aguuu                                      25

<210> SEQ ID NO 25
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 25
gaugguauag auauagugug uaugg                                      25

<210> SEQ ID NO 26
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 26
gauuaaauuu gcacgaggaa agagg                                      25

<210> SEQ ID NO 27
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 27
acgaugaacu aagauugaau ugugu                                      25

<210> SEQ ID NO 28
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 28
acagagguau uagauuuugc auuua                                      25

<210> SEQ ID NO 29
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 29
uuaauuaggu guauaacgug ucaaa                                      25

<210> SEQ ID NO 30
<211> LENGTH: 25
<212> TYPE: RNA
<213> ORGANISM: Artificial Sequence
<220> FEATURE:
<223> OTHER INFORMATION: Nucleic acid probe
```

```
<400> SEQUENCE: 30
agaagaaaaa caaagacauu uggau                                              25

<210> SEQ ID NO 31
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 31
aggaaggugg acaggacguu gcaua                                              25

<210> SEQ ID NO 32
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 32
gaaccaacau auauuaucac gcagg                                              25

<210> SEQ ID NO 33
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 33
auccauauua uuccauaccu aaauc                                              25

<210> SEQ ID NO 34
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 34
ucaggauuac aauauagggu auuua                                              25

<210> SEQ ID NO 35
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 35
gacacugaaa acucuaauag auaug                                              25

<210> SEQ ID NO 36
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 36
aauguauauc aauggauuau aaaca                                              25

<210> SEQ ID NO 37
<211> LENGTH: 25
```

```
<212> TYPE: RNA
<213> ORGANISM: Artificial Sequence
<220> FEATURE:
<223> OTHER INFORMATION: Nucleic acid probe

<400> SEQUENCE: 37
cuauuggaga gcauuggggu aaagg                                         25

<210> SEQ ID NO 38
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 38
ggugauuguc cuccauuaga auuaa                                         25

<210> SEQ ID NO 39
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 39
uaguauauag ggacgacaca ccaca                                         25

<210> SEQ ID NO 40
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 40
cugaaaccca aguguaaaca ugcgu                                         25

<210> SEQ ID NO 41
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 41 gcaugauuu guguauagua uauag                                          25

<210> SEQ ID NO 42
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 42
uccaguugaa aagcaaagac auuua                                         25

<210> SEQ ID NO 43
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 43
```
uuguaaaugu gaggcgacac uacgu                                              25

<210> SEQ ID NO 44
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 44
aagauuuauu aaugggcaca uuugg                                              25

<210> SEQ ID NO 45
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 45
gcacaaacau cuacuaucau gcagg                                              25

<210> SEQ ID NO 46
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 46
caauacagag uauuuagagu aaaau                                              25

<210> SEQ ID NO 47
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 47
cuaauaaguu uggauuucca gacac                                              25

<210> SEQ ID NO 48
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 48
ugguuugggc cuguacagga guuga                                              25

<210> SEQ ID NO 49
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 49
guacagauaa cagggaaugc auuuc                                              25

<210> SEQ ID NO 50
<211> LENGTH: 25
<212> TYPE: RNA
<213> ORGANISM: Artificial Sequence

```
<220> FEATURE:
<223> OTHER INFORMATION: Nucleic acid probe

<400> SEQUENCE: 50
uaaccgaaaa cgguuugacc gaaaa                                              25

<210> SEQ ID NO 51
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 51
cgaaaaacca cgcaaccugc acgaa                                              25

<210> SEQ ID NO 52
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 52
cuuuggaaac cacggugcau gaaau                                              25

<210> SEQ ID NO 53
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 53
cuuuggacag aaacgaggua uauga                                              25

<210> SEQ ID NO 54
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 54
ucugugagug cacuuugcgu uugug                                              25

<210> SEQ ID NO 55
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 55
aauccagcag augcuuauga acaca                                              25

<210> SEQ ID NO 56
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 56
uauugaaaua gggcgaggac agccu                                              25
```

```
<210> SEQ ID NO 57
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 57
cugauaauag ggaaugcuug ucuau                                    25

<210> SEQ ID NO 58
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 58
uuuggaacuu augaauacug uuauu                                    25

<210> SEQ ID NO 59
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 59
gagcagguaa auuagggag gaugu                                     25

<210> SEQ ID NO 60
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 60
gcaaacacuu cugcacugca aaccu                                    25

<210> SEQ ID NO 61
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 61
gcuaaaccua aacuaaaacg uucuu                                    25

<210> SEQ ID NO 62
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 62
caaaacguaa aagguuaaa aggua                                     25

<210> SEQ ID NO 63
<211> LENGTH: 25
<212> TYPE: RNA
<213> ORGANISM: Artificial Sequence
<220> FEATURE:
<223> OTHER INFORMATION: Nucleic acid probe
```

-continued

```
<400> SEQUENCE: 63
guguagcuaa cgcacggcca uguuu                                              25

<210> SEQ ID NO 64
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 64
ugcacgaauu gugugaggug cugga                                              25

<210> SEQ ID NO 65
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 65
uacaacgaag agagguauac aaguu                                              25

<210> SEQ ID NO 66
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 66
acgaauagua uauagagaca auaau                                              25

<210> SEQ ID NO 67
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 67
ggcauuauca auauucacug uaugg                                              25

<210> SEQ ID NO 68
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 68
cuaugagcaa uuaggugaca gcuca                                              25

<210> SEQ ID NO 69
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 69
gccagaugga caagcagaac aagcc                                              25

<210> SEQ ID NO 70
```

```
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 70
uaacaguagg acaucccuau uuuuc                                              25

<210> SEQ ID NO 71
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 71
aaaaaaguuu aguucccaa ggugu                                               25

<210> SEQ ID NO 72
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 72
uuugaugaua cugaaaccag uaaca                                              25

<210> SEQ ID NO 73
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 73
agggaauguu uaucuaugga uuaua                                              25

<210> SEQ ID NO 74
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 74
ugcaaaccuc cuauagguga acauu                                              25

<210> SEQ ID NO 75
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 75 aggauggga caugguagau acagg                                               25

<210> SEQ ID NO 76
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 76
```
uagaagacag cggauauggc aauac                                      25

<210> SEQ ID NO 77
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 77
gcuguacaga uugguguaua acagg                                      25

<210> SEQ ID NO 78
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 78
auugguuuag aacagcaaug ucaaa                                      25

<210> SEQ ID NO 79
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 79
ucauauuuug gaaugaguuu aauac                                      25

<210> SEQ ID NO 80
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 80
uuuugguugc agccauuauc agaug                                      25

<210> SEQ ID NO 81
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 81
aauagaggaa gaggacaagg aaaac                                      25

<210> SEQ ID NO 82
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 82
auggaggaaa uaucagcacg uuuaa                                      25

<210> SEQ ID NO 83
<211> LENGTH: 25
<212> TYPE: RNA

<213> ORGANISM: Artificial Sequence
<220> FEATURE:
<223> OTHER INFORMATION: Nucleic acid probe

<400> SEQUENCE: 83
caucacaaau ugaacauugg aaacu                               25

<210> SEQ ID NO 84
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 84
ggacauugca acaaacaagc uuaga                               25

<210> SEQ ID NO 85
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 85
auuuuaaaua uuuuaaagag gaugc                               25

<210> SEQ ID NO 86
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 86
aauauccacu acugaaacug cugac                               25

<210> SEQ ID NO 87
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 87
caaauaguuu aaaauguuua agaua                               25

<210> SEQ ID NO 88
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 88
ugauguguau uaauuuucau gcaca                               25

<210> SEQ ID NO 89
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 89
ucuacaaggc gcaagcgugc aucug                               25

```
<210> SEQ ID NO 90
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 90
gaaaacauac caauggauac cuuug                                          25

<210> SEQ ID NO 91
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 91
gcccuguggc acgccuuggu uuaua                                          25

<210> SEQ ID NO 92
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 92
cagauguccg uguggcggcc uagug                                          25

<210> SEQ ID NO 93
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 93
acauugcagg cuaauaaaag ugaug                                          25

<210> SEQ ID NO 94
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 94
caguacaugc aaauauccag auuau                                          25

<210> SEQ ID NO 95
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 95
gagaaauggu gcaaugggca uauga                                          25

<210> SEQ ID NO 96
<211> LENGTH: 25
<212> TYPE: RNA
<213> ORGANISM: Artificial Sequence
<220> FEATURE:
```

<223> OTHER INFORMATION: Nucleic acid probe

<400> SEQUENCE: 96
uuuuuaaaag guauaccuaa aaaaa                                              25

<210> SEQ ID NO 97
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 97
uaacagugca auacgauaau gauaa                                              25

<210> SEQ ID NO 98
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 98
cagauguccg uguggcggcc uagug                                              25

<210> SEQ ID NO 99
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 99
aggccacugu guaccugccu ccugu                                              25

<210> SEQ ID NO 100
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 100
uuagaggacu ggcaauuugg ccuua                                              25

<210> SEQ ID NO 101
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 101
cauguuuuaa acugcuuuua ggcac                                              25

<210> SEQ ID NO 102
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 102
augcugcaug ccauaaaugu auaga                                              25

```
<210> SEQ ID NO 103
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 103
uuaaaacgaa aguuugcagg aggca                                            25

<210> SEQ ID NO 104
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 104
ucagauagug gcuauggcug uucug                                            25

<210> SEQ ID NO 105
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 105
uuagaaauuu uaaaagugau aaaac                                            25

<210> SEQ ID NO 106
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 106
uguaaauggg gaguauuaau auuag                                            25

<210> SEQ ID NO 107
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 107
caccaaaauu gcgaaguagu guugc                                            25

<210> SEQ ID NO 108
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 108
augcauuucc auuugauaaa aaugg                                            25

<210> SEQ ID NO 109
<211> LENGTH: 25
<212> TYPE: RNA
<213> ORGANISM: Artificial Sequence
<220> FEATURE:
<223> OTHER INFORMATION: Nucleic acid probe
```

```
<400> SEQUENCE: 109
gaaaggacau gguccagauu agauu                                         25

<210> SEQ ID NO 110
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 110
uugauuguaa ugacucuaug ugcag                                         25

<210> SEQ ID NO 111
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 111
uaccagugac gacacgguau ccgcu                                         25

<210> SEQ ID NO 112
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 112
gugguaacac uacgccuaua auaca                                         25

<210> SEQ ID NO 113
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 113
guaauaaaac ugcuuuuagg cacau                                         25

<210> SEQ ID NO 114
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 114
aggauccaac acggcgaccc uacaa                                         25

<210> SEQ ID NO 115
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 115
cuucacugca agacauagaa auaac                                         25

<210> SEQ ID NO 116
<211> LENGTH: 25
```

-continued

<212> TYPE: RNA
<213> ORGANISM: Artificial Sequence
<220> FEATURE:
<223> OTHER INFORMATION: Nucleic acid probe

<400> SEQUENCE: 116
agguauuuga auuugcauuu aaaga                                      25

<210> SEQ ID NO 117
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 117
gaggccagug ccauucgugc ugcaa                                      25

<210> SEQ ID NO 118
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 118
ugguaaucca uauuuaggg uuccu                                       25

<210> SEQ ID NO 119
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 119
uuccuaaggu uucugcauac caaua                                      25

<210> SEQ ID NO 120
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 120
auccugaaac acaacguuua gugug                                      25

<210> SEQ ID NO 121
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 121
aggacguuag ggacaaugug ucugu                                      25

<210> SEQ ID NO 122
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 122

```
ugacgaucca aagcaacgac ccuac                                          25

<210> SEQ ID NO 123
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 123
uagacaccuu aaggacaaac gaaga                                          25

<210> SEQ ID NO 124
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 124
gugugacggc agaauugagc uuaca                                          25

<210> SEQ ID NO 125
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 125
uacagcagcu guuuugagc accuu                                           25

<210> SEQ ID NO 126
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 126
uguaggcaau ccauauuuua gggguu                                         25

<210> SEQ ID NO 127
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 127
uuccuaaggu auccgcauau cagua                                          25

<210> SEQ ID NO 128
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 128
auaauccuga aacacaacgu uuggu                                          25

<210> SEQ ID NO 129
<211> LENGTH: 25
<212> TYPE: RNA
<213> ORGANISM: Artificial Sequence
```

```
<220> FEATURE:
<223> OTHER INFORMATION: Nucleic acid probe

<400> SEQUENCE: 129
aggauguuag ggauaaugug ucagu                                    25

<210> SEQ ID NO 130
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 130
ccauacaaau ugccagaccu gugca                                    25

<210> SEQ ID NO 131
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 131
ucgguguaug caacuacauu agaaa                                    25

<210> SEQ ID NO 132
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 132
uacaaugaaa uacagccggu ugacc                                    25

<210> SEQ ID NO 133
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 133
uuguauguca cgagcaauua ggaga                                    25

<210> SEQ ID NO 134
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 134
gaugaaauag augaacccga ccaug                                    25

<210> SEQ ID NO 135
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 135
agcgugagac agcacaggua cuuuu                                    25
```

<210> SEQ ID NO 136
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 136
agugcuauag auagugaaaa ccagg                                     25

<210> SEQ ID NO 137
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 137 guaaagauu gugcaacaau gugua                                      25

<210> SEQ ID NO 138
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 138
aaauuuccua augcauuucc auuug                                     25

<210> SEQ ID NO 139
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 139
gaaaagacuu ggugcagauu agacu                                     25

<210> SEQ ID NO 140
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 140
gacgaggaug aaggagacaa ugaug                                     25

<210> SEQ ID NO 141
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 141
aagcauauca agcuauugaa cugca                                     25

<210> SEQ ID NO 142
<211> LENGTH: 25
<212> TYPE: RNA
<213> ORGANISM: Artificial Sequence
<220> FEATURE:
<223> OTHER INFORMATION: Nucleic acid probe

```
<400> SEQUENCE: 142
cauuguccug acucuaugug cagua                                          25

<210> SEQ ID NO 143
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 143
acaccaguac caacauuuac aggca                                          25

<210> SEQ ID NO 144
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 144
cagguucgug uuaguaauuu ugauu                                          25

<210> SEQ ID NO 145
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 145
cacccuucau cauuuguaac auuug                                          25

<210> SEQ ID NO 146
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 146
auaauccugc uuuugagccu guuga                                          25

<210> SEQ ID NO 147
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 147
gauccggauu uucuggacau uguuc                                          25

<210> SEQ ID NO 148
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 148
ugcaaauguc ugcagaugug uaugg                                          25

<210> SEQ ID NO 149
```

```
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 149
cuaaacacaa acguaaacgu guguc                                              25

<210> SEQ ID NO 150
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 150
gcaacagaua cagguucaga cuugg                                              25

<210> SEQ ID NO 151
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 151
auuuguguac aggcagagcg cgaga                                              25

<210> SEQ ID NO 152
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 152
uuagucauca uccguccag gugca                                               25

<210> SEQ ID NO 153
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 153
uauaaaacca ugcaaaaguu gcuug                                              25

<210> SEQ ID NO 154
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 154
ccugcagaac ggccauacaa auugc                                              25

<210> SEQ ID NO 155
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 155
```
ugcaugccaa aauguauua aauuu                                    25

<210> SEQ ID NO 156
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 156
gacguauacg aagagaaaca caagu                                   25

<210> SEQ ID NO 157
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 157
acauugcaag agauuguuuu agauu                                   25

<210> SEQ ID NO 158
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 158
cuacacugca cuuaguagua gaagc                                   25

<210> SEQ ID NO 159
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 159
gcagcuguuu auggagacac uguca                                   25

<210> SEQ ID NO 160
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 160
ggguaucccu accugauccu aauaa                                   25

<210> SEQ ID NO 161
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 161
uauaauccug acacacaacg ccugg                                   25

<210> SEQ ID NO 162
<211> LENGTH: 25
<212> TYPE: RNA

<213> ORGANISM: Artificial Sequence
<220> FEATURE:
<223> OTHER INFORMATION: Nucleic acid probe

<400> SEQUENCE: 162
cuucagaguu auauauuaaa ggcac                                   25

<210> SEQ ID NO 163
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 163
auguauauuc cccuucccca agugg                                   25

<210> SEQ ID NO 164
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 164
cacguaguac uaauuuuaca uuguc                                   25

<210> SEQ ID NO 165
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 165
cuguauauag cccuacaaag uuuaa                                   25

<210> SEQ ID NO 166
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 166
ucuaaacaca aacggaaacg ugugu                                   25

<210> SEQ ID NO 167
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 167
uuauagugua uagagacugu acacc                                   25

<210> SEQ ID NO 168
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 168
uuuuaugcaa gaguaagaga auuaa                                   25

```
<210> SEQ ID NO 169
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 169
uauuauagag auuccguguaa uggag                                              25

<210> SEQ ID NO 170
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 170
ugccuaaaac cucuaugucc aacag                                               25

<210> SEQ ID NO 171
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 171
accacaaaau uaugaggaag uugac                                               25

<210> SEQ ID NO 172
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 172
cuccgagaau gaaaagaug aacca                                                25

<210> SEQ ID NO 173
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 173
uggacaucca uauuuaaag uaccu                                                25

<210> SEQ ID NO 174
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 174
uuccuaaggu gucugcauau caaua                                               25

<210> SEQ ID NO 175
<211> LENGTH: 25
<212> TYPE: RNA
<213> ORGANISM: Artificial Sequence
<220> FEATURE:
```

<223> OTHER INFORMATION: Nucleic acid probe

<400> SEQUENCE: 175
uggaugacac ugaaaacucu caugu                              25

<210> SEQ ID NO 176
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 176
gauaauguau cuguggauua uaaac                              25

<210> SEQ ID NO 177
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 177
ugaaucacua uauauuaaag guacu                              25

<210> SEQ ID NO 178
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 178 uauucccuu ccccaagugg gucug                               25

<210> SEQ ID NO 179
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 179
gugcagcgcc ugccccuacc ucuac                              25

<210> SEQ ID NO 180
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 180
ucuuccagaa aauaguguug uuugu                              25

<210> SEQ ID NO 181
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 181
uguauuguuu gccuguuugu auguu                              25

```
<210> SEQ ID NO 182
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 182
ccguuuuguu caaucugcug cugua                                              25

<210> SEQ ID NO 183
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 183
aagacagcaa cgacaagcgc guagu                                              25

<210> SEQ ID NO 184
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 184
aagcggaugu agaaaacagu uauuu                                              25

<210> SEQ ID NO 185
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 185
acggaccagc cgcguacucu agcug                                              25

<210> SEQ ID NO 186
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 186
uaugcauagu uugcaacuuc cuugu                                              25

<210> SEQ ID NO 187
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 187
gcagagauuu augcauuuca auaua                                              25

<210> SEQ ID NO 188
<211> LENGTH: 25
<212> TYPE: RNA
<213> ORGANISM: Artificial Sequence
<220> FEATURE:
<223> OTHER INFORMATION: Nucleic acid probe
```

<400> SEQUENCE: 188
guggagacac ggcuuccac augcu                                         25

<210> SEQ ID NO 189
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 189
aaauaaauua uagaaggcau cgcga                                        25

<210> SEQ ID NO 190
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 190
ugcauggaaa uguggcuaca auuga                                        25

<210> SEQ ID NO 191
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 191
guggaggugu guguuguaag acagu                                        25

<210> SEQ ID NO 192
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 192
cauaagggua cugcaggaac ugcuu                                        25

<210> SEQ ID NO 193
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 193
aaacgaaagu auauaggcag uccgu                                        25

<210> SEQ ID NO 194
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 194
gaguuuuaug gaccuagcac ggucc                                        25

<210> SEQ ID NO 195
<211> LENGTH: 25

```
<212> TYPE: RNA
<213> ORGANISM: Artificial Sequence
<220> FEATURE:
<223> OTHER INFORMATION: Nucleic acid probe

<400> SEQUENCE: 195
uuauuggcug uuggacaucc auauu                                               25

<210> SEQ ID NO 196
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 196
uauuccuaaa guaucaggau aucaa                                               25

<210> SEQ ID NO 197
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 197
cuauagguga acacugggcu aaagg                                               25

<210> SEQ ID NO 198
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 198
gcuggugacu guccuccuuu ggaau                                               25

<210> SEQ ID NO 199
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 199
ggauuuuaaa acccuacaaa ccuca                                               25

<210> SEQ ID NO 200
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 200
auuuguaaau auccugauua ccuua                                               25

<210> SEQ ID NO 201
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 201
```
guaguacuaa ccuaacauug ugugc                                              25

<210> SEQ ID NO 202
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 202
uucugacuuu agggaguaua uuaga                                              25

<210> SEQ ID NO 203
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 203
uaugcugcaa cuccuagugg cucua                                              25

<210> SEQ ID NO 204
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 204
uagaugacag uguauuugac cuguc                                              25

<210> SEQ ID NO 205
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 205 uaugggaca guauguuuuu uuguu                                               25

<210> SEQ ID NO 206
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 206
gaggaauaug auuuacaauu uauau                                              25

<210> SEQ ID NO 207
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 207
cuacccgacc cuacaaacua ccaga                                              25

<210> SEQ ID NO 208
<211> LENGTH: 25
<212> TYPE: RNA
<213> ORGANISM: Artificial Sequence

```
<220> FEATURE:
<223> OTHER INFORMATION: Nucleic acid probe

<400> SEQUENCE: 208
aagauauaga aauaagcugu guaua                                              25

<210> SEQ ID NO 209
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 209
auagcgacuc uguguauggg gaaac                                              25

<210> SEQ ID NO 210
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 210
augauauauu aauaaggugu uuacg                                              25

<210> SEQ ID NO 211
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 211
auauaaugaa gugcaagagg uugac                                              25

<210> SEQ ID NO 212
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 212
aggaagaaau agaugaacca gauaa                                              25

<210> SEQ ID NO 213
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 213
augacacaga aaauucccau guugc                                              25

<210> SEQ ID NO 214
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 214
gauaaugugu caguggauua uaaac                                              25
```

<210> SEQ ID NO 215
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 215
gggaacauug ggcuaagggu acugc                                              25

<210> SEQ ID NO 216
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 216
uguccuccau uagaacuagu aaaua                                              25

<210> SEQ ID NO 217
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 217
gaaacuuaua uauaaaggu acuaa                                               25

<210> SEQ ID NO 218
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 218
uauucuccau caccuagugg gucua                                              25

<210> SEQ ID NO 219
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 219
caucugccau uacaugucag aagga                                              25

<210> SEQ ID NO 220
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 220
uaugaaaaau uaaaguuuug gaaug                                              25

<210> SEQ ID NO 221
<211> LENGTH: 25
<212> TYPE: RNA
<213> ORGANISM: Artificial Sequence
<220> FEATURE:
<223> OTHER INFORMATION: Nucleic acid probe

```
<400> SEQUENCE: 221
guuuuuacuu gcuuuaauua cacua                                    25

<210> SEQ ID NO 222
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 222
acaagaaaua ucguuaaaua gcuau                                    25

<210> SEQ ID NO 223
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 223
caagggagca uggucuuaaa acaau                                    25

<210> SEQ ID NO 224
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 224
gcagguacag uguguauauu gcaag                                    25

<210> SEQ ID NO 225
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 225
gugccgcaac ccgaaauuga ccuac                                    25

<210> SEQ ID NO 226
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 226
ggacuaugaa caauuugaca gcuca                                    25

<210> SEQ ID NO 227
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 227
guaauaguau agugcagcua gcugu                                    25

<210> SEQ ID NO 228
```

```
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 228
guacagggug guuuucagua gaagc                                              25

<210> SEQ ID NO 229
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 229
agaacagccc guugcaagac auaac                                              25

<210> SEQ ID NO 230
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 230
auacugaagu ggaaacucuu acgcc                                              25

<210> SEQ ID NO 231
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 231
agugugugua gucagggggg gucaa                                              25

<210> SEQ ID NO 232
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 232
uguggcaggc ucuguagcag aaagu                                              25

<210> SEQ ID NO 233
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 233
auuuaucaaa aauggugcaa ugggc                                              25

<210> SEQ ID NO 234
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 234
```
ggcaaaauau guaaaagacu gugca                                      25

<210> SEQ ID NO 235
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 235
gacagcaaug ggaauccugu auaug                                      25

<210> SEQ ID NO 236
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 236
ugguccagau uagauuugga ggagg                                      25

<210> SEQ ID NO 237
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 237
aucuaccugg cauuggacca guaau                                      25

<210> SEQ ID NO 238
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 238
guuugugcuu ugcgugugug ugugu                                      25

<210> SEQ ID NO 239
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 239
ccuuugauaa uccugcauau gaacc                                      25

<210> SEQ ID NO 240
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 240
guacuaguga cagcaaggua uaucu                                      25

<210> SEQ ID NO 241
<211> LENGTH: 25
<212> TYPE: RNA

<213> ORGANISM: Artificial Sequence
<220> FEATURE:
<223> OTHER INFORMATION: Nucleic acid probe

<400> SEQUENCE: 241
gaaacagcau guuuuuuuuu cuucg                                              25

<210> SEQ ID NO 242
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 242
acaacacauc cugccuccua cgcuu                                              25

<210> SEQ ID NO 243
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 243
aauaaaacug cuguuaggca cauau                                              25

<210> SEQ ID NO 244
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 244
cacuugggcc ugaagaaaag caaaa                                              25

<210> SEQ ID NO 245
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 245
guguaauaaa gccaugcgug guaau                                              25

<210> SEQ ID NO 246
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 246
aaauugacuu gcaaugcuac gagca                                              25

<210> SEQ ID NO 247
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 247
uggacaggcu acguguuaca gaauu                                              25

<210> SEQ ID NO 248
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 248
agcagcccau uaggagacau uacaa                                          25

<210> SEQ ID NO 249
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 249
gauuacugga caguuauccg gacag                                          25

<210> SEQ ID NO 250
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 250
uguggaagca acguugcagg uagau                                          25

<210> SEQ ID NO 251
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 251
acagccacua gaggaugcua aaaua                                          25

<210> SEQ ID NO 252
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 252
guccagauua gauuuggagg aggaa                                          25

<210> SEQ ID NO 253
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 253
ugccaggaga aaauacuaga cuguu                                          25

<210> SEQ ID NO 254
<211> LENGTH: 25
<212> TYPE: RNA
<213> ORGANISM: Artificial Sequence
<220> FEATURE:

<223> OTHER INFORMATION: Nucleic acid probe

<400> SEQUENCE: 254
ucaaccuggc auuggaccag uaaua                                              25

<210> SEQ ID NO 255
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 255
acaagccaau augugcugcu aauug                                              25

<210> SEQ ID NO 256
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 256
ugugugugug ucuuguguug uguug                                              25

<210> SEQ ID NO 257
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 257
acaugcaaag cugcugguac auguc                                              25

<210> SEQ ID NO 258
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 258
uggagugggu uggguauauu uuugg                                              25

<210> SEQ ID NO 259
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 259
gaacuugaaa ugcagccuuu acuuu                                              25

<210> SEQ ID NO 260
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 260
ugucuucauc uuaugcaaau guuac                                              25

```
<210> SEQ ID NO 261
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 261
uggggauuac uauuuguggc ccuau                                              25

<210> SEQ ID NO 262
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 262
aaacgccgua aacguauacc cuauu                                              25

<210> SEQ ID NO 263
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 263
ucuuccucuu ccucuucagc caaac                                              25

<210> SEQ ID NO 264
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 264
ccgaaaacgg uacauauaaa agcac                                              25

<210> SEQ ID NO 265
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 265
gacaccagag gaaaaacagu uacac                                              25

<210> SEQ ID NO 266
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 266
augagcaauu gaacagcuca gagga                                              25

<210> SEQ ID NO 267
<211> LENGTH: 25
<212> TYPE: RNA
<213> ORGANISM: Artificial Sequence
<220> FEATURE:
<223> OTHER INFORMATION: Nucleic acid probe
```

<400> SEQUENCE: 267
caauggcguc accugaaggu acaga								25

<210> SEQ ID NO 268
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 268
uaaaacgaaa guauuuaggc agucc								25

<210> SEQ ID NO 269
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 269
cagcggguau ggcaauacuu uggaa								25

<210> SEQ ID NO 270
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 270
acacagucac uuuugguuac aaccg								25

<210> SEQ ID NO 271
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 271
gaaaggacau gguccagauu agauu								25

<210> SEQ ID NO 272
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 272
cgugccagga gaaaauucua gacug								25

<210> SEQ ID NO 273
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 273
uacaagugug uaaagcaaag gcaug								25

<210> SEQ ID NO 274
<211> LENGTH: 25

```
<212> TYPE: RNA
<213> ORGANISM: Artificial Sequence
<220> FEATURE:
<223> OTHER INFORMATION: Nucleic acid probe

<400> SEQUENCE: 274
uaaaggcaca ugggaagugc auaug                                      25

<210> SEQ ID NO 275
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 275
guauuuauug ucccgacucu guguc                                      25

<210> SEQ ID NO 276
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 276
gaaauaccua ugcaaacauu ugcug                                      25

<210> SEQ ID NO 277
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 277
cacagaccug ccuuuacaac acgua                                      25

<210> SEQ ID NO 278
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 278
gguggugugc guuuuaguag gcuug                                      25

<210> SEQ ID NO 279
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 279
agaaguggca aacaaauagg ugcuc                                      25

<210> SEQ ID NO 280
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 280
```
gauggccuau augauauuua ugcaa    25

<210> SEQ ID NO 281
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 281
uucccuauuu ucuugcagau ggcgg    25

<210> SEQ ID NO 282
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 282
gcuuagagga caaauacaga uaugu    25

<210> SEQ ID NO 283
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 283
uguaugacug uauguaugug uaaug    25

<210> SEQ ID NO 284
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 284
ccgaaaacgg uacauauaaa aggca    25

<210> SEQ ID NO 285
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 285
cucagaggau gaggaugagg augaa    25

<210> SEQ ID NO 286
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 286
gcggccacag caagcuagac aagcu    25

<210> SEQ ID NO 287
<211> LENGTH: 25
<212> TYPE: RNA
<213> ORGANISM: Artificial Sequence

```
<220> FEATURE:
<223> OTHER INFORMATION: Nucleic acid probe

<400> SEQUENCE: 287
gcguuaacag uaacgugccc acucu                                              25

<210> SEQ ID NO 288
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 288
gcaaguacaa acagcacaug cagau                                              25

<210> SEQ ID NO 289
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 289
acagacguug caaaaacuaa aacga                                              25

<210> SEQ ID NO 290
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 290
augaauaugu gccaguggau aaagc                                              25

<210> SEQ ID NO 291
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 291 ugaaggggu gauuggaaac ccauu                                               25

<210> SEQ ID NO 292
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 292
ggauaacgac gaggacaaag aaaac                                              25

<210> SEQ ID NO 293
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 293
uguaaagcaa aagcauguag ugcaa                                              25
```

<210> SEQ ID NO 294
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 294
guccugacuc ugugucuagu accug                                  25

<210> SEQ ID NO 295
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 295
guaucccaca gaccaggaaa acgac                                  25

<210> SEQ ID NO 296
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 296
guuugcgcuu ugcuuuugug uuugu                                  25

<210> SEQ ID NO 297
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 297
auaggccugc auuuacuaca cguag                                  25

<210> SEQ ID NO 298
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 298
gauauaaguc cuauugcaca ggcug                                  25

<210> SEQ ID NO 299
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 299
aggcgccgua aacguauucc cuauu                                  25

<210> SEQ ID NO 300
<211> LENGTH: 25
<212> TYPE: RNA
<213> ORGANISM: Artificial Sequence
<220> FEATURE:
<223> OTHER INFORMATION: Nucleic acid probe -continued

```
<400> SEQUENCE: 300
cuaccuccaa caccuguuuc aaagg                                          25

<210> SEQ ID NO 301
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 301
uucuaugugg uuuuacuuac gcagg                                          25

<210> SEQ ID NO 302
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 302
auaaaccuua uugguugcaa cgugc                                          25

<210> SEQ ID NO 303
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 303
acgcgugguu gcauaaacua aggug                                          25

<210> SEQ ID NO 304
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 304
uaauaaggug cggaaaaugc caaaa                                          25

<210> SEQ ID NO 305
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 305
gacaacucag aggaugagga ugaaa                                          25

<210> SEQ ID NO 306
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 306
agaagauggc ugauucaggu aauug                                          25

<210> SEQ ID NO 307
```

```
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 307
cgggaugguu uaauguagaa gccau                                           25

<210> SEQ ID NO 308
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 308 uggggauuu uauugauaau gcaca                                            25

<210> SEQ ID NO 309
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 309
aaugcagaca augaggcuau acgug                                           25

<210> SEQ ID NO 310
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 310
gauauggcaa uacugaagug gaaac                                           25

<210> SEQ ID NO 311
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 311
uagugggucc aguagcauuu caaau                                           25

<210> SEQ ID NO 312
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 312
uuuaacagag gacgacgaca aggaa                                           25

<210> SEQ ID NO 313
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 313
```
aagccuugca guaucacgau ccaaa                                          25

<210> SEQ ID NO 314
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 314
uguugcaacc uccuccaccc uuaga                                          25

<210> SEQ ID NO 315
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 315
gccucuggca gacuuuuauu uucaa                                          25

<210> SEQ ID NO 316
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 316
aacagguuaa gguuguagac ccugc                                          25

<210> SEQ ID NO 317
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 317
cagcacagug acuugcauaa ugcuc                                          25

<210> SEQ ID NO 318
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 318
uacuagaagu ggcaaacgua uaggu                                          25

<210> SEQ ID NO 319
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 319
aaagguauac cugcccccug ugucu                                          25

<210> SEQ ID NO 320
<211> LENGTH: 25
<212> TYPE: RNA

```
<213> ORGANISM: Artificial Sequence
<220> FEATURE:
<223> OTHER INFORMATION: Nucleic acid probe

<400> SEQUENCE: 320
aaaguuucag guuugcaaua caggg                                          25

<210> SEQ ID NO 321
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 321
cuguuguaga uacuacuaga agcac                                          25

<210> SEQ ID NO 322
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 322
uuuuggcuuc cugcaggcaa cuugg                                          25

<210> SEQ ID NO 323
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 323
ugcacacaca uuuuuaccc acccu                                           25

<210> SEQ ID NO 324
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 324
gaaaacgguu caaccgaaaa cgguu                                          25

<210> SEQ ID NO 325
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 325
gaccaguugu gcaagacguu uaauc                                          25

<210> SEQ ID NO 326
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 326
acugcuggac aacaugcaug gaaga                                          25
```

<210> SEQ ID NO 327
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 327
gacccuguag gguuacauug cuaug                                           25

<210> SEQ ID NO 328
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 328
agacagcuca gaagaugagg uggac                                           25

<210> SEQ ID NO 329
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 329
guugcugugg augugacagc aacgu                                           25

<210> SEQ ID NO 330
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 330
cggacgauuc agguacagaa aauga                                           25

<210> SEQ ID NO 331
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 331
cauuaugcga cugugcagga ccuaa                                           25

<210> SEQ ID NO 332
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 332
acagccaaaa aagguaaagc gacgg                                           25

<210> SEQ ID NO 333
<211> LENGTH: 25
<212> TYPE: RNA
<213> ORGANISM: Artificial Sequence
<220> FEATURE:

```
<223> OTHER INFORMATION: Nucleic acid probe

<400> SEQUENCE: 333
gaaaaugggg gagaugguca ggaaa                                    25

<210> SEQ ID NO 334
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 334
gaggacgagg aagauggaag caaua                                    25

<210> SEQ ID NO 335
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 335
ggcagcacag uuauauguuc uccug                                    25

<210> SEQ ID NO 336
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 336
cuacuacaua caccccgca cagac                                     25

<210> SEQ ID NO 337
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 337
cuaugggaac acccuuuagu ccugu                                    25

<210> SEQ ID NO 338
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 338
acgccguaaa cguaucccu uauuu                                     25

<210> SEQ ID NO 339
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 339
uagcgacagc acaguauaug ugccu                                    25
```

<210> SEQ ID NO 340
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 340
caggcuuugg ugcuaugaau uuugc                                    25

<210> SEQ ID NO 341
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 341
cugugguaga uaccacacgc aguac                                    25

<210> SEQ ID NO 342
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 342
gaguaaccua aggucacaca ccugc                                    25

<210> SEQ ID NO 343
<211> LENGTH: 25
<212> TYPE: RNA
<213> ORGANISM: Artificial Sequence
<220> FEATURE:
<223> OTHER INFORMATION: Nucleic acid probe

<400> SEQUENCE: 343
ccacacccua cauauuuccu ucuua                                    25

<210> SEQ ID NO 344
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 344
tgtatggtgc aaacggccgt tatcagag                                 28

<210> SEQ ID NO 345
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 345
acattgcatg aactgcgggt catc                                     24

<210> SEQ ID NO 346
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 346
tctactgtgc agaaacaccg gaatagga                                            28

<210> SEQ ID NO 347
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 347
tacgaaacag ctgactacaa ctgaactaca a                                        31

<210> SEQ ID NO 348
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 348
tctggtcatt ggaggggggag ctgtcagtac                                         30

<210> SEQ ID NO 349
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 349
cagctgacta caactgaact acaagc                                              26

<210> SEQ ID NO 350
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 350
ggctatccat atgcagcctg cgcgtgc                                             27

<210> SEQ ID NO 351
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 351
caagacatct tagacgtgct aattcgg                                             27

<210> SEQ ID NO 352
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 352
caagacattt tagacgtgct aattcgg                                             27

<210> SEQ ID NO 353
<211> LENGTH: 28

```
<212> TYPE: DNA
<213> ORGANISM: Artificial Sequence
<220> FEATURE:
<223> OTHER INFORMATION: Nucleic acid probe

<400> SEQUENCE: 353
ggtaaaacat atactaacca aggcgcgg                                         28

<210> SEQ ID NO 354
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 354
ggtaaaacat atactaacca aggcacgg                                         28

<210> SEQ ID NO 355
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 355
acagctagaa ctttatttga attatgtg                                         28

<210> SEQ ID NO 356
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 356
taacagcatt ttacaaacag ctgaggtgct g                                     31

<210> SEQ ID NO 357
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 357
agcgtgtgta aagtgtttag aattttat                                         28

<210> SEQ ID NO 358
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 358
tgcagaagct atgtccatgg gtgcacagga                                       30

<210> SEQ ID NO 359
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 359
```
gcttttgtgt agaaattgtg gaatacctttg    31

<210> SEQ ID NO 360
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 360
ggcagcattt gcacttagag aattat    26

<210> SEQ ID NO 361
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 361
gtgtgcctgt tgcttagaac tgcaaggg    28

<210> SEQ ID NO 362
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 362
actaaagcac atattgggaa aggcacgc    28

<210> SEQ ID NO 363
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 363
gagtgcacag acggagacat cagacaacta c    31

<210> SEQ ID NO 364
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 364
cagacatttt atgcaccaaa aaagaact    28

<210> SEQ ID NO 365
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 365
agtttgtatg gaacaacatt agaacagcaa t    31

<210> SEQ ID NO 366
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 366
cataaagtta ccagatttat gcacagagc                                    29

<210> SEQ ID NO 367
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 367
cgatgtatgt cttgttgcag atcatca                                      27

<210> SEQ ID NO 368
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 368
gctacctgat ctgtgcacgg aactgaaca                                    29

<210> SEQ ID NO 369
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 369
gcaagacagt attggaactt acag                                         24

<210> SEQ ID NO 370
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 370
ccgagcacga caggaacgac tccaacgacg c                                 31

<210> SEQ ID NO 371
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 371
agagaacgac ccagaacgct acatgagc                                     28

<210> SEQ ID NO 372
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 372
tgcaatttgt gacctaagag tagtatatag ag                                32

<210> SEQ ID NO 373
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 373
acgttcgagt gctggagcag atgttaatgg aa                          32

<210> SEQ ID NO 374
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 374
tccttggtgt gccatcagtg tgctgcacag t                           31

<210> SEQ ID NO 375
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 375
acactgcatg cagtgcgggt caac                                   24

<210> SEQ ID NO 376
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 376
gcgtgtattg cagacgagcg ctttcagac                              29

<210> SEQ ID NO 377
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 377
gcgtgtattg cagacgagcg ctttcagac                              29

<210> SEQ ID NO 378
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 378
agcgctttca gacgctgatg tatt                                   24

<210> SEQ ID NO 379
<211> LENGTH: 24
<212> TYPE: DNA
<213> ORGANISM: Artificial Sequence
<220> FEATURE:
<223> OTHER INFORMATION: Nucleic acid probe

```
<400> SEQUENCE: 379
agcgctttca gacgctgatg tatt                                       24

<210> SEQ ID NO 380
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 380
gcactgcata ttctgcgcca aagtgc                                     26

<210> SEQ ID NO 381
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 381
gccaaagtgc tgaccacagc ggagctat                                   28

<210> SEQ ID NO 382
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 382
actgcagggc attgtgcgac gcctgaagca c                               31

<210> SEQ ID NO 383
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 383
tgcatagctg gctactggag agggagctgt c                               31

<210> SEQ ID NO 384
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 384
cagcccagaa ctggcagcat tttgc                                      25

<210> SEQ ID NO 385
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 385
cgctgcttat tgtttgaagg cataaagc                                   28

<210> SEQ ID NO 386
```

```
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 386
gtgccacaag ccacttgtca gagagg                                              26

<210> SEQ ID NO 387
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 387
caaaatttct ggatactgga gagggagttg c                                        31

<210> SEQ ID NO 388
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 388
gcaccatctt tgtgaggtac aagaaacatc g                                        31

<210> SEQ ID NO 389
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 389
caagaaggaa ttatccagct cagagg                                              26

<210> SEQ ID NO 390
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 390
gactggtata tagggaggac agccca                                              26

<210> SEQ ID NO 391
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 391
cacaacgtcc actgagacag cagtataat                                           29

<210> SEQ ID NO 392
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 392
```
ctgcgtgccc tacaacagat gcttatgggc                      30

<210> SEQ ID NO 393
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 393
ctactgcaaa ggtcagttaa cagaaa                          26

<210> SEQ ID NO 394
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 394
ctactgcaaa ggtcagttaa cagaaaca                        28

<210> SEQ ID NO 395
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 395
ttgacaaaca aggtatatg tgatttg                          27

<210> SEQ ID NO 396
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 396
aaaaagaaac gattccacaa catagg                          26

<210> SEQ ID NO 397
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 397
accacttaac cagtgctgaa gcgtatgca                       29

<210> SEQ ID NO 398
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 398
gcatacagta gaacaagaaa caggactact g                    31

<210> SEQ ID NO 399
<211> LENGTH: 28
<212> TYPE: DNA

```
<213> ORGANISM: Artificial Sequence
<220> FEATURE:
<223> OTHER INFORMATION: Nucleic acid probe

<400> SEQUENCE: 399
cctgccaacg tgtgacccga caacgtgc                                          28

<210> SEQ ID NO 400
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 400
gccagtgtag taaccgggga aacacc                                            26

<210> SEQ ID NO 401
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 401
ctgtgtttgc ggttcttatc taaaattagt g                                      31

<210> SEQ ID NO 402
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 402
cacaacattg aactacagtg cgtggaatgc                                        30

<210> SEQ ID NO 403
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 403
attattctgt atatggacat acattagaac a                                      31

<210> SEQ ID NO 404
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 404
attattctgt atatggaaat acattagaac a                                      31

<210> SEQ ID NO 405
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 405
tgtaaaaacg ccatgagagg acacaagcc                                         29
```

```
<210> SEQ ID NO 406
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 406
acacaacatt gaactacagt gcgtgga                                          27

<210> SEQ ID NO 407
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 407
acaccacatt gaactacagt gcgtgga                                          27

<210> SEQ ID NO 408
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 408
attattcgct atatggagaa acattagaac a                                     31

<210> SEQ ID NO 409
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 409
caggatataa atctaaaaca tattc                                            25

<210> SEQ ID NO 410
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 410
caggatgtaa atctaaaata tattc                                            25

<210> SEQ ID NO 411
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 411
atctgcaaat gcaaaatcat atacctcag                                        29

<210> SEQ ID NO 412
<211> LENGTH: 29
<212> TYPE: DNA
<213> ORGANISM: Artificial Sequence
<220> FEATURE:
```

```
<223> OTHER INFORMATION: Nucleic acid probe

<400> SEQUENCE: 412
atctgcaaat acaaagtcat atacctcag                                       29

<210> SEQ ID NO 413
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 413
cagccttatg tgaagaggtc aacatttca                                       29

<210> SEQ ID NO 414
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 414
gcaggacatt gtgttagatc tgaaaccaac g                                    31

<210> SEQ ID NO 415
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 415
cacacgctga cctattagtg ttagaagacc                                      30

<210> SEQ ID NO 416
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 416
agaaggccag ccatatggag tatgcatg                                        28

<210> SEQ ID NO 417
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 417
gaagaaaaaa aacgattcca taacatcgg                                       29

<210> SEQ ID NO 418
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 418
acagagcaca cacattgaca tacgtaaatt gg                                   32
```

```
<210> SEQ ID NO 419
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 419
tgcagacgac cactacagca aaccgagg                                        28

<210> SEQ ID NO 420
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 420
gcagacgacc actacagcaa accgagg                                         27

<210> SEQ ID NO 421
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 421
ccagcagaaa aattaagaca cctaaatagc                                      30

<210> SEQ ID NO 422
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 422
aagagaaacc caagtataac atcagatatg cg                                   32

<210> SEQ ID NO 423
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 423
ctaacacgaa gagaaaccca agtataacat c                                    31

<210> SEQ ID NO 424
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 424
caggccagga ccctgtatga actgtgtg                                        28

<210> SEQ ID NO 425
<211> LENGTH: 30
<212> TYPE: DNA
<213> ORGANISM: Artificial Sequence
<220> FEATURE:
<223> OTHER INFORMATION: Nucleic acid probe
```

<400> SEQUENCE: 425
aagacggtcc taaaaacagc tgaggtactg        30

<210> SEQ ID NO 426
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 426
cgcatgtcca cggtgcctgg acctgcac        28

<210> SEQ ID NO 427
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 427
gcacttaaca ggcgcagagg tgctcgcg        28

<210> SEQ ID NO 428
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 428
gtatacagtg gagaaagaaa ctggactact t        31

<210> SEQ ID NO 429
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 429
gtacagcaga cacaggtaga acacggac        28

<210> SEQ ID NO 430
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 430
ctttgactac gcagcatatg cagatactgt        30

<210> SEQ ID NO 431
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 431
cagtgtttga tttgtgcatt agatgc        26

<210> SEQ ID NO 432
<211> LENGTH: 26

```
<212> TYPE: DNA
<213> ORGANISM: Artificial Sequence
<220> FEATURE:
<223> OTHER INFORMATION: Nucleic acid probe

<400> SEQUENCE: 432
atcaccagtg gaaaaagtac agcata                                    26

<210> SEQ ID NO 433
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 433
gcacatcctg tctgtgtgta attcgac                                   27

<210> SEQ ID NO 434
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 434
gaaaaacgtt aagtactgca gaggttt                                   27

<210> SEQ ID NO 435
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 435
taagtcaatt ctggacgtgc tgatacg                                   27

<210> SEQ ID NO 436
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 436
ccacctgtgg tacatgtagt cggaagg                                   27

<210> SEQ ID NO 437
<211> LENGTH: 21
<212> TYPE: DNA
<213> ORGANISM: Artificial Sequence
<220> FEATURE:
<223> OTHER INFORMATION: Nucleic acid probe

<400> SEQUENCE: 437
gcattacagg atggcgcgct t                                         21

<210> SEQ ID NO 438
<211> LENGTH: 23
<212> TYPE: DNA
<213> ORGANISM: Artificial Sequence
<220> FEATURE:
<223> OTHER INFORMATION: Nucleic acid probe

<400> SEQUENCE: 438
```
ccattgaacc cagcagaaaa acg                                           23

<210> SEQ ID NO 439
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 439
gtagagagct cggcagagga ccttagaaca c                                  31

<210> SEQ ID NO 440
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 440
gaagctttga acgtttctat gcacaatata                                    30

<210> SEQ ID NO 441
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 441
caaaaattag agagtataga cgttatagca gg                                 32

<210> SEQ ID NO 442
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 442
atgcgctaat tgctggcaac gtacacgac                                     29

<210> SEQ ID NO 443
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 443
gaggatccag caacacgacc ccggaccc                                      28

<210> SEQ ID NO 444
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 444
ggctgcagtg tgtgcagtgc aaaaaagagc                                    30

<210> SEQ ID NO 445
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 445
ccatatggcg tgtgtattat gtgcctacgc                             30

<210> SEQ ID NO 446
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 446
gatgaggagg atacagatgg tgtggaccg                              29

<210> SEQ ID NO 447
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 447
gaggatccag cgacacgacc ccgg                                   24

<210> SEQ ID NO 448
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 448
aggctgcagt gtgtgcagtg caaaaaagag c                           31

<210> SEQ ID NO 449
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 449
aggctgcagt gtgtgcagtg taaaaaagag c                           31

<210> SEQ ID NO 450
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 450
tgtgcagtgc aaaaaagagc tacaacgaag a                           31

<210> SEQ ID NO 451
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 451
ggaaaacatt agaagagagg gtaaaaaaac ca                          32

<210> SEQ ID NO 452
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 452
ggaaaacatt agaagagagg gtaagaaaac ca                                    32

<210> SEQ ID NO 453
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 453
ggaaaacatt agaagagagg gtaaaaagac ca                                    32

<210> SEQ ID NO 454
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 454
ggaaaacatt agaagagagg ttaaaaaaac ca                                    32

<210> SEQ ID NO 455
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 455
ggaaaacatt agaagagagg gtcgaaaaac ca                                    32

<210> SEQ ID NO 456
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 456
tatataattt tgcatataca gatctaagag                                       30

<210> SEQ ID NO 457
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 457
gcaagaaggc attgacagcg tcagagg                                          27

<210> SEQ ID NO 458
<211> LENGTH: 24
<212> TYPE: DNA
<213> ORGANISM: Artificial Sequence
<220> FEATURE:
<223> OTHER INFORMATION: Nucleic acid probe

```
<400> SEQUENCE: 458
gtatagagac gggtatccgt atgg                                              24

<210> SEQ ID NO 459
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 459
atggtataga gacgggtatc cgtatgg                                           27

<210> SEQ ID NO 460
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 460
gggggcaatg tctgctactg aaccccac                                          28

<210> SEQ ID NO 461
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 461
gccttttgca agaagacggt gtgtaca                                           27

<210> SEQ ID NO 462
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 462
gcttgtgcac tgtgcctaga actgcacggg c                                      31

<210> SEQ ID NO 463
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 463
acggctatgt gtgtatagca cgcacacagg                                        30

<210> SEQ ID NO 464
<211> LENGTH: 23
<212> TYPE: DNA
<213> ORGANISM: Artificial Sequence
<220> FEATURE:
<223> OTHER INFORMATION: Nucleic acid probe

<400> SEQUENCE: 464
gggggcaatg tctgctactg aac                                               23

<210> SEQ ID NO 465
```

```
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 465
gacggtgtgt acagcagata tttatgca                                          28

<210> SEQ ID NO 466
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 466
taaattacag aatacctgga agggtcg                                           27

<210> SEQ ID NO 467
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 467
ccacctgtgg tacatgtaac cggaacg                                           27

<210> SEQ ID NO 468
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 468
ttgcaaaaaa gaactaacac gtgctgagg                                         29

<210> SEQ ID NO 469
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 469
agtgtatagg gatgattttc cttatgc                                           27

<210> SEQ ID NO 470
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 470
aacatctaga gaacctagag aatcta                                            26

<210> SEQ ID NO 471
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 471
```
gaactaacac gtgctgaggt atataat                                    27

<210> SEQ ID NO 472
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 472
gcaataaaca ccatctgcaa tggatgacc                                  29

<210> SEQ ID NO 473
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 473
cctgtaacaa cgccatgaga ggaaacaacc caacgc                          36

<210> SEQ ID NO 474
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 474
gtatgcagcg tgtctgaaat gcatttca                                   28

<210> SEQ ID NO 475
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 475
gaacattaga ggctgaaacc aagacacc                                   28

<210> SEQ ID NO 476
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 476
catgagctgc tgatacgctg ttataga                                    27

<210> SEQ ID NO 477
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 477
cttgtgtgct acgagcaatt acctgactcc ga                              32

<210> SEQ ID NO 478
<211> LENGTH: 27
<212> TYPE: DNA

```
<213> ORGANISM: Artificial Sequence
<220> FEATURE:
<223> OTHER INFORMATION: Nucleic acid probe

<400> SEQUENCE: 478
aacattagag gctgaaacca agacacc                                          27

<210> SEQ ID NO 479
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 479
ccgtagggtc agcaaagcac actcatctat                                       30

<210> SEQ ID NO 480
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 480
gcagcaaacc gttaagtata cagg                                             24

<210> SEQ ID NO 481
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 481
agcaaaccgt taagtataca ggaaaaggag c                                     31

<210> SEQ ID NO 482
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 482
gctacatgaa ctactgctgg gcgacttgtc c                                     31

<210> SEQ ID NO 483
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 483
tgtggacctg gacgacctgc accta                                            25

<210> SEQ ID NO 484
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 484
acggcggtgg cagcactcat gcttt                                            25
```

<210> SEQ ID NO 485
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 485
ggaaaaggag tatcaggtag agagggg        27

<210> SEQ ID NO 486
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 486
gattccatat tcagcaatac acaggaa        27

<210> SEQ ID NO 487
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 487
gatcccatat tcagcaatac acaggaa        27

<210> SEQ ID NO 488
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 488
caaaaaggaa cttacaagtt tagagc        26

<210> SEQ ID NO 489
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 489
agtatataga aacaattggc catatgc        27

<210> SEQ ID NO 490
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 490
ccggagtatg gggcaacatt agaaagta        28

<210> SEQ ID NO 491
<211> LENGTH: 23
<212> TYPE: DNA
<213> ORGANISM: Artificial Sequence
<220> FEATURE:

<223> OTHER INFORMATION: Nucleic acid probe

<400> SEQUENCE: 491
gtatggggca acattagaaa gta                                          23

<210> SEQ ID NO 492
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 492
tatatagaaa caattggcca tatgc                                        25

<210> SEQ ID NO 493
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 493
attagtatat agaaacaatt ggccatatgc ag                                32

<210> SEQ ID NO 494
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 494
cggtaaatat ataaagcaca ccagtgtcca                                   30

<210> SEQ ID NO 495
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 495
cagtgcaaga aatatgtttc aggacacaga                                   30

<210> SEQ ID NO 496
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 496
aagtttgccc tgcgtgcagt gcaaaaaaa                                    29

<210> SEQ ID NO 497
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 497
cattcacagt acagcagcag acgtccgaac                                   30

```
<210> SEQ ID NO 498
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 498
gcagaaggca actacaacgg acagagg                                         27

<210> SEQ ID NO 499
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 499
tcaagaaaca caagtttaag taactatgca                                      30

<210> SEQ ID NO 500
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 500
cgtccgagcg gtggagcagc tgctgatggg c                                    31

<210> SEQ ID NO 501
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 501
gagtttggtg tgccaccagt gtgctacata c                                    31

<210> SEQ ID NO 502
<211> LENGTH: 23
<212> TYPE: DNA
<213> ORGANISM: Artificial Sequence
<220> FEATURE:
<223> OTHER INFORMATION: Nucleic acid probe

<400> SEQUENCE: 502
gagtttggtg tgccaccagt gtg                                             23

<210> SEQ ID NO 503
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 503
acgtccgagc ggtggagcag ctgctg                                          26

<210> SEQ ID NO 504
<211> LENGTH: 28
<212> TYPE: DNA
<213> ORGANISM: Artificial Sequence
<220> FEATURE:
<223> OTHER INFORMATION: Nucleic acid probe
```

```
<400> SEQUENCE: 504
cccatacgga atggcgcgat ttcccaat                                           28

<210> SEQ ID NO 505
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 505
atagtatata gaaacgggga gccatatgc                                          29

<210> SEQ ID NO 506
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 506
ataaatataa atatgcatgg accacggccg                                         30

<210> SEQ ID NO 507
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 507
ctcacaagag aacctgcgat ctctact                                            27

<210> SEQ ID NO 508
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 508
acaagtataa atataaatat gcatggacca cg                                      32

<210> SEQ ID NO 509
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 509
gtttgctgca tgtgcctgct gtttggaaat                                         30

<210> SEQ ID NO 510
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 510
tagacaccgg aacgccagtt acagagcaac                                         30

<210> SEQ ID NO 511
<211> LENGTH: 27
```

```
<212> TYPE: DNA
<213> ORGANISM: Artificial Sequence
<220> FEATURE:
<223> OTHER INFORMATION: Nucleic acid probe

<400> SEQUENCE: 511
agaaagaata attacagaag gcaggcg                                          27

<210> SEQ ID NO 512
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 512
acgatactgg acgtattcgg gctacgg                                          27

<210> SEQ ID NO 513
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 513
gtcaggaaaa ggaatatcag gtgcagacag g                                     31

<210> SEQ ID NO 514
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 514
atgagaggga cggtgttggt gtgcag                                           26

<210> SEQ ID NO 515
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 515
aacctggact gtgtgttttg ccaacgtgg                                        29

<210> SEQ ID NO 516
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 516
gtataggcga tatagacaat cagtatatgg ca                                    32

<210> SEQ ID NO 517
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 517
```

```
actttagacc tgaaaccaac aaccgaaat                                          29

<210> SEQ ID NO 518
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 518
acaaagctga tttaagagtg atagaagagt                                         30

<210> SEQ ID NO 519
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 519
ccatttgcag cgtgcgccat ttgctta                                            27

<210> SEQ ID NO 520
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 520
aaactaggcg acacctggaa agggcgctgc                                         30

<210> SEQ ID NO 521
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 521
gtgcagtgta caggaccaga catcaacaat                                         30

<210> SEQ ID NO 522
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 522
gctggggcca gcaaatccta ccaatttgtt t                                       31

<210> SEQ ID NO 523
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 523
cgcagcgtgc ttgtgcagag aagctaaagt ac                                      32

<210> SEQ ID NO 524
<211> LENGTH: 31
<212> TYPE: DNA
<213> ORGANISM: Artificial Sequence
```

<220> FEATURE:
<223> OTHER INFORMATION: Nucleic acid probe

<400> SEQUENCE: 524
gcggcggtgg caatattcgt gcttcggacc a                          31

<210> SEQ ID NO 525
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 525
ccacaagtaa aggacatagt gttggag                               27

<210> SEQ ID NO 526
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 526
ggtggtggac gacaaaaaaa ggtttcat                              28

<210> SEQ ID NO 527
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 527
gcctggtggg cccgtgttgc gcgaacaact                            30

<210> SEQ ID NO 528
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 528
ccactggcac agctgtatat acgatgccat                            30

<210> SEQ ID NO 529
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 529
tgtgctgtgc caggaatacg aggtggagtt cgacg                      35

<210> SEQ ID NO 530
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 530
aggaagaatt aacggaaggc gaagtgc                               27

```
<210> SEQ ID NO 531
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 531
gtaaaggaat tactaattgt ttggagg                                        27

<210> SEQ ID NO 532
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 532
cctatgcaac acactggaca catcactgc                                      29

<210> SEQ ID NO 533
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 533
gttagaaaaa ctaacaaata gcaatatat                                      29

<210> SEQ ID NO 534
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 534
ctgtattgct atgaggaatt aaacaactca g                                   31

<210> SEQ ID NO 535
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 535
gacctatgca acacactgga cacatcactg c                                   31

<210> SEQ ID NO 536
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 536
ctaaaggaat tattactggt ctggaaa                                        27

<210> SEQ ID NO 537
<211> LENGTH: 29
<212> TYPE: DNA
<213> ORGANISM: Artificial Sequence
<220> FEATURE:
<223> OTHER INFORMATION: Nucleic acid probe
```

```
<400> SEQUENCE: 537
caagacacag gcgtatcatt ggcacactt                                    29

<210> SEQ ID NO 538
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 538
ctgcatatgg tggaattaaa tctgcat                                      27

<210> SEQ ID NO 539
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 539
ttaagggaat tattgctggt gtggaga                                      27

<210> SEQ ID NO 540
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 540
gggaattatt gctggtgtgg agatttgg                                     28

<210> SEQ ID NO 541
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 541
gagcatatga tacacgcgaa tctgcac                                      27

<210> SEQ ID NO 542
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 542
atattgcacc aaggagctta caac                                         24

<210> SEQ ID NO 543
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 543
ggcagctgcc ccatggtgta tgtgcaccg                                    29

<210> SEQ ID NO 544
```

```
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 544
cggccgcacg ccgaccatcc aggat                                    25

<210> SEQ ID NO 545
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 545
cgtgtggtgt gtgctatcgt gcagttagg                                29

<210> SEQ ID NO 546
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 546
gtacgcggca ttagcagtaa cagtagag                                 28

<210> SEQ ID NO 547
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 547
cgagtgcacc tcttgttatt gttcaattcg t                             31

<210> SEQ ID NO 548
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 548
gcacctcttg ttattgttca attcgtc                                  27

<210> SEQ ID NO 549
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 549
gtgctgcgtg ttctgcacca aacagc                                   26

<210> SEQ ID NO 550
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 550
```
cgtgttctgc accaaacagc tgaccgtagc c        31

<210> SEQ ID NO 551
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 551
cagctgaccg tagccgaatt gactgc        26

<210> SEQ ID NO 552
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 552
ctggagaggg tgttgtgctt attgctggac ac        32

<210> SEQ ID NO 553
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 553
cgatgctgat ttgtatgatc cagatacccca        30

<210> SEQ ID NO 554
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 554
tcagttccaa ctccaggcag tcatgtt        27

<210> SEQ ID NO 555
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 555
caagcgcgcc gctgtttcgg ggaccacgc        29

<210> SEQ ID NO 556
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 556
tccctgacct tttgggatgt ggatctcagt        30

<210> SEQ ID NO 557
<211> LENGTH: 31
<212> TYPE: DNA

<213> ORGANISM: Artificial Sequence
<220> FEATURE:
<223> OTHER INFORMATION: Nucleic acid probe

<400> SEQUENCE: 557
ccccaaatct tctaattcca agatggatat t                           31

<210> SEQ ID NO 558
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 558
agcagaatgc gtcaccgggt gattgt                                 26

<210> SEQ ID NO 559
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 559
tctagagctt attactgcac ctatacaag                              29

<210> SEQ ID NO 560
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 560
gttgtacatt aaaggtgaca gtcagagcgg c                           31

<210> SEQ ID NO 561
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 561
aacagtgtac taatacacct gtacaggc                               28

<210> SEQ ID NO 562
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 562
tcctattgac atatgtggca ctacatgt                               28

<210> SEQ ID NO 563
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 563
tataattaag ggtagtggaa atcgcacgt                              29

<210> SEQ ID NO 564
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 564
gctgccccta aacgtaagcg cgcc                                            24

<210> SEQ ID NO 565
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 565
ggaacccacc tgcacagggc gattgccc                                        28

<210> SEQ ID NO 566
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 566
caacggtggg gggcgagacg ttggta                                          26

<210> SEQ ID NO 567
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 567
taccaatatg tgcttgtgtg ttccttct                                        28

<210> SEQ ID NO 568
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 568
gcctcccctg ccactacgta tgacgcc                                         27

<210> SEQ ID NO 569
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 569
ttcatccctg tttgacccca ctacacag                                        28

<210> SEQ ID NO 570
<211> LENGTH: 30
<212> TYPE: DNA
<213> ORGANISM: Artificial Sequence
<220> FEATURE:

<223> OTHER INFORMATION: Nucleic acid probe

<400> SEQUENCE: 570
agtggtgggt atggtggtaa tcctggtcag                                  30

<210> SEQ ID NO 571
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 571
gggtacacaa tgttcaaata cctctgtaca aaa                              33

<210> SEQ ID NO 572
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 572
tgttcccctt gatatttgtg gaactgtctg c                                31

<210> SEQ ID NO 573
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 573
aacatccaga ctacttgcag ttgga                                       25

<210> SEQ ID NO 574
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 574
attttacaat ccagatacac agcggctg                                    28

<210> SEQ ID NO 575
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 575
agcaaatgca ggtgtggata ataga                                       25

<210> SEQ ID NO 576
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 576
tccccatgta acaatgttgc agtaaatcca                                  30

```
<210> SEQ ID NO 577
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 577
gcaggtggtg gcaataagca ggata                                          25

<210> SEQ ID NO 578
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 578
ggcctgtgct ggagtggaaa ttggc                                          25

<210> SEQ ID NO 579
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 579
ccatgccgcc acgtctaatg tttctg                                         26

<210> SEQ ID NO 580
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 580
gtctcctgta cctgggcaat atgatg                                         26

<210> SEQ ID NO 581
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 581
cctgcaatag ttgtgcatgg ggata                                          25

<210> SEQ ID NO 582
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 582
tggccaaaag gccgaaattc ctaag                                          25

<210> SEQ ID NO 583
<211> LENGTH: 27
<212> TYPE: DNA
<213> ORGANISM: Artificial Sequence
<220> FEATURE:
<223> OTHER INFORMATION: Nucleic acid probe
```

<400> SEQUENCE: 583
gacactgaca acagggacaa tgtttca                                27

<210> SEQ ID NO 584
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 584
ggagccccct acatcttcta tttat                                  25

<210> SEQ ID NO 585
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 585
aaacctgcaa tagttgtgca tggggata                               28

<210> SEQ ID NO 586
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 586
ggcgggggct gttggggatg ctata                                  25

<210> SEQ ID NO 587
<211> LENGTH: 22
<212> TYPE: DNA
<213> ORGANISM: Artificial Sequence
<220> FEATURE:
<223> OTHER INFORMATION: Nucleic acid probe

<400> SEQUENCE: 587
gggggctgtt ggggatgcta ta                                     22

<210> SEQ ID NO 588
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 588
actggccaaa aggccgaaat tcctaag                                27

<210> SEQ ID NO 589
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 589
attaaaggtg ctgaatcagg cagggagccc                             30

<210> SEQ ID NO 590
<211> LENGTH: 36

<210> SEQ ID NO 590
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 590
taaggcgggg gctgttgggg atgctatacc caccac                                36

<210> SEQ ID NO 591
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 591
cactaactta cctgcaatag ttgtgcatgg ggata                                 35

<210> SEQ ID NO 592
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 592
aaaacgcacc gctgttgcgg gggcggcgg                                       29

<210> SEQ ID NO 593
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 593
agctgaggtg tctgataata ctaattataa a                                    31

<210> SEQ ID NO 594
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 594
actatctcgg accccggcag tcatgtg                                         27

<210> SEQ ID NO 595
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 595
ggtagcaata ataggttggc agtgcctaag gtg                                  33

<210> SEQ ID NO 596
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 596

```
atcatccact aacaaagcag atgtgcccaa a                                31
```

```
<210> SEQ ID NO 597
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 597
gtcaaaatac acaacaggga gattgccctc cg                               32
```

```
<210> SEQ ID NO 598
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 598
tattacaggc caataaatcg gacgtgccct                                  30
```

```
<210> SEQ ID NO 599
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 599
cagggcaacg ggagggatgt gattggt                                     27
```

```
<210> SEQ ID NO 600
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 600
acattattca attcccaaat cctctggta                                   29
```

```
<210> SEQ ID NO 601
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 601
ggaggtaggt cgagggcaac ctctcggtgt c                                31
```

```
<210> SEQ ID NO 602
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 602
cactgtgtgt gcacgcacta gttccgctgc                                  30
```

```
<210> SEQ ID NO 603
<211> LENGTH: 31
<212> TYPE: DNA
<213> ORGANISM: Artificial Sequence
```

```
<220> FEATURE:
<223> OTHER INFORMATION: Nucleic acid probe

<400> SEQUENCE: 603
gttgtgtgct accacagagt ctcaaccgtt g                             31

<210> SEQ ID NO 604
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 604
gcccctcagg ccccatttga cactaca                                  27

<210> SEQ ID NO 605
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 605
ggctggtaat tccaaaacag atgtt                                    25

<210> SEQ ID NO 606
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 606
aaataacagg gatcccccgc caagctca                                 28

<210> SEQ ID NO 607
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 607
ttccttacta tttattgtgc atgaatgtat g                             31

<210> SEQ ID NO 608
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 608
cagtgctagg ctgcttacag taggc                                    25

<210> SEQ ID NO 609
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 609
gacaatccta aaaaatagt tgtaccaaag gtg                            33
```

<210> SEQ ID NO 610
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 610
ccggtggtcc tggcactgat aatagg                                26

<210> SEQ ID NO 611
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 611
tagtccttgt agtaacaatg ctattacccc t                          31

<210> SEQ ID NO 612
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 612
gccattagat attatgaact ccattag                               27

<210> SEQ ID NO 613
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 613
ggacatgtat ataaaagctt ctaatgg                               27

<210> SEQ ID NO 614
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 614
tatccaactc ccagtggttc tatggtca                              28

<210> SEQ ID NO 615
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 615
ctgaagacac atacaagtct actaac                                26

<210> SEQ ID NO 616
<211> LENGTH: 30
<212> TYPE: DNA
<213> ORGANISM: Artificial Sequence
<220> FEATURE:
<223> OTHER INFORMATION: Nucleic acid probe

```
<400> SEQUENCE: 616
gctaaaaaat tattggtacc caaagtatca                                         30

<210> SEQ ID NO 617
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 617
agtatcctgg acaaccgggt gctgataat                                          29

<210> SEQ ID NO 618
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 618
cttggatgta agcctccaac aggggaa                                            27

<210> SEQ ID NO 619
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 619
cacatccacc cgcacatcgt ctgca                                              25

<210> SEQ ID NO 620
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 620
actaatggga aacgtaagat tgctgta                                            27

<210> SEQ ID NO 621
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 621
gtggaaacat agcagatagt agggag                                             26

<210> SEQ ID NO 622
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 622
aggtactgta ggcgatgcta ttccagatga ct                                      32

<210> SEQ ID NO 623
```

```
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 623
gtctgcacct tcatcatcta gtacag                                              26

<210> SEQ ID NO 624
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 624
aaagtggaaa catagcagat agtagggag                                           29

<210> SEQ ID NO 625
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 625
cagttctagg ctattagctg tgggtcac                                            28

<210> SEQ ID NO 626
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 626
gcagtaccca aggtatctgg tttg                                                24

<210> SEQ ID NO 627
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 627
atcattttat gatccctgcc tccagcgtt                                           29

<210> SEQ ID NO 628
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 628
aaatatgttg gtaactctgg taactctg                                            28

<210> SEQ ID NO 629
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 629
```

-continued

```
atatagggta tttcgcgtga cattgccc                                28

<210> SEQ ID NO 630
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 630
aaaggcatgc aagcccaata atgtatcta                               29

<210> SEQ ID NO 631
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 631
acgtgcaaac cccggtagtt ctgtatactg                              30

<210> SEQ ID NO 632
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 632
cagtttggta gacacttaca gatacc                                  26

<210> SEQ ID NO 633
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 633
caaaaaggcc aaataagaca tctatcccca aa                           32

<210> SEQ ID NO 634
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 634
taatttatat aacccagata cgcagcgca                               29

<210> SEQ ID NO 635
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 635
acatatggtg gaggccctgg tacagac                                 27

<210> SEQ ID NO 636
<211> LENGTH: 30
<212> TYPE: DNA
```

<213> ORGANISM: Artificial Sequence
<220> FEATURE:
<223> OTHER INFORMATION: Nucleic acid probe

<400> SEQUENCE: 636
actgtctgta ggtaaacgaa aggcgtctac                               30

<210> SEQ ID NO 637
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 637
gtacctaatg gtgcaggtaa taaacaggct g                             31

<210> SEQ ID NO 638
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 638
gtttagagta gctttacccg atcct                                    25

<210> SEQ ID NO 639
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 639
ttgggcatgt gtaggtatgg aaattggt                                 28

<210> SEQ ID NO 640
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 640
gctcatgcag ctacagctgt tattacgc                                 28

<210> SEQ ID NO 641
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 641
ccaagcattc tattgttata ctaggtgggg                               30

<210> SEQ ID NO 642
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 642
ctcaacgcgt gctgctattc ctaaa                                    25

<210> SEQ ID NO 643
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 643
gtaatggccg tgaccctata gaaag                                    25

<210> SEQ ID NO 644
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 644
tatgttagtt tttgtatgct tgtgcacact                               30

<210> SEQ ID NO 645
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 645
ttaactatta gcactgccac tgctgc                                   26

<210> SEQ ID NO 646
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 646
aacctcaacg cgtgctgcta ttcctaaa                                 28

<210> SEQ ID NO 647
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 647
aacctcaacg cgtgctgcta ttcctaaagt a                             31

<210> SEQ ID NO 648
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 648
tattaaaaac accagtagtg gtaatggt                                 28

<210> SEQ ID NO 649
<211> LENGTH: 29
<212> TYPE: DNA
<213> ORGANISM: Artificial Sequence
<220> FEATURE:

<210> SEQ ID NO 650
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 649
aatatgctgg taaacctggt atagataat					29

<210> SEQ ID NO 650
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 650
aaccccttgt aataataatt caggaa					26

<210> SEQ ID NO 651
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 651
cctacagctc attaacagtg taatac					26

<210> SEQ ID NO 652
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 652
atagctattc aggatactgc cccggac					27

<210> SEQ ID NO 653
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 653
cccattggaa cttatcaatt cacctatt					28

<210> SEQ ID NO 654
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 654
cgttattggt gaggaaatac ctaatgac					28

<210> SEQ ID NO 655
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 655
ctttccgcaa ccacacagtc tatgtc					26

```
<210> SEQ ID NO 656
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 656
ttaaagtaca aaaaccaat aataagcaaa g                              31

<210> SEQ ID NO 657
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 657
caacctatgt acacctaata cattggct                                 28

<210> SEQ ID NO 658
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 658
agtgaggtac cccttgatgt agctacctca                               30

<210> SEQ ID NO 659
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 659
tacagcatcc acgcaggata gctttaataa                               30

<210> SEQ ID NO 660
<211> LENGTH: 23
<212> TYPE: DNA
<213> ORGANISM: Artificial Sequence
<220> FEATURE:
<223> OTHER INFORMATION: Nucleic acid probe

<400> SEQUENCE: 660
gactaaggac aataccaaaa caa                                      23

<210> SEQ ID NO 661
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 661
gtactgctac agaacagtta agtaa                                    25

<210> SEQ ID NO 662
<211> LENGTH: 22
<212> TYPE: DNA
<213> ORGANISM: Artificial Sequence
<220> FEATURE:
<223> OTHER INFORMATION: Nucleic acid probe
```

```
<400> SEQUENCE: 662
gccagtggcc accagcctag aa                                              22

<210> SEQ ID NO 663
<211> LENGTH: 22
<212> TYPE: DNA
<213> ORGANISM: Artificial Sequence
<220> FEATURE:
<223> OTHER INFORMATION: Nucleic acid probe

<400> SEQUENCE: 663
actaggtcaa agcctgctgt ag                                              22

<210> SEQ ID NO 664
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 664
aaaatctgct cctacctcca cctctacac                                       29

<210> SEQ ID NO 665
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 665
atctgctcct acctccacct ctacac                                          26

<210> SEQ ID NO 666
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 666
gagctctagg ctcctcacag taggccat                                        28

<210> SEQ ID NO 667
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 667
gaaaaatagc actaataagg tgtctgta                                        28

<210> SEQ ID NO 668
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 668
caacctctat gatcccgaca cccagcgtct g                                    31

<210> SEQ ID NO 669
<211> LENGTH: 31
```

<212> TYPE: DNA
<213> ORGANISM: Artificial Sequence
<220> FEATURE:
<223> OTHER INFORMATION: Nucleic acid probe

<400> SEQUENCE: 669
tgtcaaaagt tctaccgtcc agaccccgg t                              31

<210> SEQ ID NO 670
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 670
cagttccaga cttttggctg ttggca                                   26

<210> SEQ ID NO 671
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 671
cagatatccc gcacagccag ggtct                                    25

<210> SEQ ID NO 672
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 672
cccggatgac ctttatatta aaggg                                    25

<210> SEQ ID NO 673
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 673
attacactaa ctgcagagat aatgac                                   26

<210> SEQ ID NO 674
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 674
aaaggtggta atggtagaca ggatg                                    25

<210> SEQ ID NO 675
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 675
agcatctgct gttgatacca aagatacacg t    31

<210> SEQ ID NO 676
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 676
gacatacgtg ccaacccagg cagttattta    30

<210> SEQ ID NO 677
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 677
cccatcacca aaacgtgtta agcgtcgcaa g    31

<210> SEQ ID NO 678
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 678
ccgtgaaatc aatcaatacc ttcgc    25

<210> SEQ ID NO 679
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 679
cattcctaca gatttgtatt ggaagggtg    29

<210> SEQ ID NO 680
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 680 tagacccct agacccaagg ctagt    25

<210> SEQ ID NO 681
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 681
aaagcacatt aactaaatat gatgcccgtg    30

<210> SEQ ID NO 682
<211> LENGTH: 28
<212> TYPE: DNA
<213> ORGANISM: Artificial Sequence

```
<220> FEATURE:
<223> OTHER INFORMATION: Nucleic acid probe

<400> SEQUENCE: 682
tattagtgga catccattac ttaataag                                      28

<210> SEQ ID NO 683
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 683
ataataaata ccctagccag cctggta                                       27

<210> SEQ ID NO 684
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 684
acctacagat ttgtatttta agggatct                                      28

<210> SEQ ID NO 685
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 685
caccttcttc ttcctcttcc tcctctg                                       27

<210> SEQ ID NO 686
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 686
ggtaattgta tgactgttgt gtgt                                          24

<210> SEQ ID NO 687
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 687
agtgttcctg agtctacatt atataatcca                                    30

<210> SEQ ID NO 688
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 688
ataaaaatcc taaagacagt agggac                                        26
```

<210> SEQ ID NO 689
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 689
cttgtagata cataccgcta cctacaa                                              27

<210> SEQ ID NO 690
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 690
ggaccaattc ccattaggac gcaaa                                                25

<210> SEQ ID NO 691
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 691
tctggttcaa cagcagaaat tcctaaagtg                                           30

<210> SEQ ID NO 692
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 692
ctctcgatta ttaactttgg gtcatccc                                             28

<210> SEQ ID NO 693
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 693
ctgctaatgc agacactgat aatagggac                                            29

<210> SEQ ID NO 694
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 694
taaaaatgca cagtctcagg tacagcgtgg c                                         31

<210> SEQ ID NO 695
<211> LENGTH: 25
<212> TYPE: DNA
<213> ORGANISM: Artificial Sequence
<220> FEATURE:
<223> OTHER INFORMATION: Nucleic acid probe

```
<400> SEQUENCE: 695
gtttggcctt ccggatcctt ccctt                                          25

<210> SEQ ID NO 696
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 696
ggatatacgt gagcgtcctg gtactc                                         26

<210> SEQ ID NO 697
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 697
tgcctgcacc gaaacggcca tacctg                                         26

<210> SEQ ID NO 698
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 698
gtcagctaaa tcgtcttcct cagcc                                          25

<210> SEQ ID NO 699
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 699
ctggacaaaa tacagatggt agagaa                                         26

<210> SEQ ID NO 700
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 700
acttcacaaa ctgttaatac tggtgat                                        27

<210> SEQ ID NO 701
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 701
tggtgatacc ggtgataaaa tcccagatga cc                                  32

<210> SEQ ID NO 702
```

```
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 702
ggctagtagc tctactacaa cgtatgcc                                        28

<210> SEQ ID NO 703
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 703
accagtacac gtgctgaaat acctaag                                         27

<210> SEQ ID NO 704
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 704
ccctttagat atagctcagt ccgtgtgt                                        28

<210> SEQ ID NO 705
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 705
gcattactat aatagggccg gtgtggtt                                        28

<210> SEQ ID NO 706
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 706
tactggtact ggccgtgacc ctattgg                                         27

<210> SEQ ID NO 707
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 707
actaatgtgc aatatcgtgc gggtgattgc                                      30

<210> SEQ ID NO 708
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 708
```

```
tttggatctc tgcaccacta cctgt                                              25

<210> SEQ ID NO 709
<211> LENGTH: 22
<212> TYPE: DNA
<213> ORGANISM: Artificial Sequence
<220> FEATURE:
<223> OTHER INFORMATION: Nucleic acid probe

<400> SEQUENCE: 709
tcagtctttt taccttaagg gg                                                 22

<210> SEQ ID NO 710
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 710
gggccgccgc cgccaagcct aaggac                                             26

<210> SEQ ID NO 711
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 711
tacttctgta gttacacacg acactaga                                           28

<210> SEQ ID NO 712
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 712
ctgtaagccc ggtgctgtgc aaacaggtga c                                       31

<210> SEQ ID NO 713
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 713
tgatagggca acacctggaa gctgtatt                                           28

<210> SEQ ID NO 714
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 714
tgtggttgtt ccacaaaaaa aggatcca                                           28

<210> SEQ ID NO 715
<211> LENGTH: 28
<212> TYPE: DNA
```

<213> ORGANISM: Artificial Sequence
<220> FEATURE:
<223> OTHER INFORMATION: Nucleic acid probe

<400> SEQUENCE: 715
cctgttactg tttcctccag ccctggac                                28

<210> SEQ ID NO 716
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 716
aaaccagggg actgccccccc atta                                   24

<210> SEQ ID NO 717
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 717
ctccacaagt ttggaggata cctaccgt                                28

<210> SEQ ID NO 718
<211> LENGTH: 22
<212> TYPE: DNA
<213> ORGANISM: Artificial Sequence
<220> FEATURE:
<223> OTHER INFORMATION: Nucleic acid probe

<400> SEQUENCE: 718
ggtgttttgg gaggttgacc tt                                      22

<210> SEQ ID NO 719
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 719
caagacaggg gattgtccac cattgcaa                                28

<210> SEQ ID NO 720
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 720
cgaaaagtta caggaaaaca agtcc                                   25

<210> SEQ ID NO 721
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 721 ctatttttg aaggggcgt cgtct                                     25

```
<210> SEQ ID NO 722
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 722
taacaaaccc tattggctgc agcggg                                      26

<210> SEQ ID NO 723
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 723
ggccggtggt gaccaaaacg ttggtag                                     27

<210> SEQ ID NO 724
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 724
tgtgcgtccc ttctgatgcc tccaccgcc                                   29

<210> SEQ ID NO 725
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 725
ccatctctgt ccgcaaacgc tcggcgaccg                                  30

<210> SEQ ID NO 726
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 726
ggccggtggt gaccaaaacg ttggta                                      26
```

METHODS AND COMPOSITIONS FOR SEQUENCE-SPECIFIC PURIFICATION AND MULTIPLEX ANALYSIS OF NUCLEIC ACIDS

REFERENCE TO RELATED APPLICATIONS

This application claims priority to U.S. Provisional Patent Application No. 61/299,531, filed on Jan. 29, 2010, and U.S. Provisional Patent Application No. 61/326,067, filed on Apr. 20, 2010, each of which is incorporated herein by reference in its entirety.

FIELD OF INVENTION

The present disclosure relates to methods and compositions for purifying, detecting, and characterizing nucleic acids.

BACKGROUND

The identification of the presence or absence of specific nucleic acid sequences in a sample is a central part of many assays and tests used in the modern research lab and clinical setting. In the typical scheme, the nucleic acids from the sample are first separated from other macromolecules present in the sample by manipulating various physical properties. For example, nucleic acids typically bear a net negative charge at neutral pH, owing to the phosphodiester backbone. This property can be manipulated to separate nucleic acids from other macromolecules using anion exchange resins. As another example, differential solubility of nucleic acids compared to other macromolecules in certain solvents is used to extract nucleic acids from the sample. Numerous other such schemes exist. However, the amount of target nucleic acid relative to the total amount of nucleic acid purified typically is very low. Therefore, some type of amplification is necessary. Either the amount of specific nucleotide sequence(s) is increased by target amplification methods such as polymerase chain reaction (PCR) or the specific nucleotide sequence(s) is/are reacted with a detectable label and the signal from the label is amplified to detectable levels.

Unfortunately, these methods have limited utility. One limitation is that target-specific amplification methods such as PCR are inherently error-prone. For example, although the stringency of primer hybridization can be controlled, there nonetheless exists the potential for non-specific primer binding and primer-independent amplification, which can lead to false-positive results. Moreover, different sequences can amplify at different rates, resulting in amplification bias. As a result, quantitative analysis of multiple nucleic acid sequences in a single reaction often suffers from a lack of sensitivity. In addition, target nucleic acids that are present at low concentrations relative to other nucleic acids may be effectively "masked" from the polymerase, which could result in false-negative results. Other factors may exist that reduce both the specificity and sensitivity of such assays. Another limitation of PCR is that a relatively small fragment of the target is amplified. As a result, in case of mutations/deletions the assay may produce false-negative results.

Therefore, methods and compositions are needed for specific and sensitive isolation and analysis of at least one target nucleic acid segment containing at least one specific sequence.

SUMMARY

The present disclosure in aspects and embodiments addresses these various needs and problems by providing a method of detecting and genotyping at least one target nucleic acid and isolated nucleic acids useful for the same.

In one embodiment, an isolated nucleic acid is provided, having an overall length of not more than 100 nucleotides comprising, consisting essentially of, or consisting of at least one nucleotide sequence having at least 75-percent homology to a nucleotide sequence selected from the group consisting of SEQ ID NO: 1 to SEQ ID NO: 727 and a complement thereof.

In an aspect, the isolated nucleic acid is capable of hybridizing under stringent conditions to a portion of a human papillomavirus (HPV) genome selected from the group consisting of: HPV2, HPV3, HPV6, HPV10, HPV11, HPV16, HPV18, HPV26, HPV27, HPV28, HPV29, HPV30, HPV31, HPV32, HPV33, HPV34, HPV35, HPV39, HPV42, HPV45, HPV51, HPV52, HPV53, HPV54, HPV56, HPV57, HPV58, HPV59, HPV64, HPV66, HPV67, HPV68, HPV69, HPV70, HPV73, HPV82, HPV84, HPV85, HPV86, HPV87, and HPV94.

In an aspect, the nucleic acid is capable of hybridizing under selective stringency conditions to an HPV gene selected from the group consisting of E6, E7, and L1.

In an aspect, the nucleic acid is not capable of hybridizing under stringent conditions to more than one human papillomavirus (HPV) genomes.

In an aspect, the nucleic acid is capable of hybridizing under stringent conditions to at least two of a group of human papillomavirus (HPV) genomes selected from the group consisting of: a) group A7, consisting of HPV18, HPV39, HPV45, HPV59, HPV68, HPV70, and HPV85; and b) group A9, consisting of HPV16, HPV31, HPV33, HPV35, HPV52, HPV58, and HPV67.

In another aspect, the nucleic acid is capable of hybridizing to a pair of HPV genomes selected from the group consisting of: a) HPV18 and HPV45; b) HPV39 and HPV68; c) HPV59 and HPV70; d) HPV70 and HPV85; e) HPV16 and HPV35; f) HPV31 and HPV35; g) HPV52 and HPV67; h) HPV33 and HPV58; i) HPV26 and HPV69; j) HPV51 and HPV82; k) HPV30 and HPV53; l) HPV56 and HPV66; m) HPV34 and HPV73; and n) HPV6 and HPV11.

In an aspect, the isolated nucleic acid has at least 75-percent homology across its entire length to a portion of the human papillomavirus genome, the HPV selected from the group consisting of: HPV2, HPV3, HPV6, HPV10, HPV11, HPV16, HPV18, HPV26, HPV27, HPV28, HPV29, HPV30, HPV31, HPV32, HPV33, HPV34, HPV35, HPV39, HPV42, HPV45, HPV51, HPV52, HPV53, HPV54, HPV56, HPV57, HPV58, HPV59, HPV64, HPV66, HPV67, HPV68, HPV69, HPV70, HPV73, HPV82, HPV84, HPV85, HPV86, HPV87, and HPV94.

In an aspect, the isolated nucleic acid has at least 75-percent homology across its entire length to a portion of a gene selected from the group consisting of E6, E7, and L1.

In an aspect, the isolated nucleic acid comprises a sequence selected from the group consisting of SEQ ID NO: 1 to SEQ ID NO: 727, an RNA or DNA equivalent thereof, and a complement thereof.

In another aspect, a nucleic acid probe is provided, comprising an isolated nucleic acid as disclosed herein and optionally further comprising a detectable label and/or a ligand. In a further aspect, the nucleic acid probe is provided bound to a solid support.

In a further aspect, the nucleic acid probes as set forth above are provided as a part of a probe set.

In another aspect, a method of detecting a target nucleic acid in a sample comprising non-target nucleic acids is provided, said method comprising:

(a) purifying the target nucleic acid from the sample by a method comprising:
  (i) contacting the sample with at least one purification probe, wherein at least a portion of the nucleic acid probe hybridizes to the at least one target nucleic acid to form a DNA:RNA hybrid;
  (ii) immobilizing the DNA:RNA hybrid to a first solid support by a method comprising contacting the DNA:RNA hybrid with at least a first antibody capable of binding to the DNA:RNA hybrid, wherein the antibody is bound to or adapted to be bound to the first solid support; and
  (iii) separating the first solid support from the sample to generate at least one purified target nucleic acid;
b. genotyping the purified target nucleic acid by a method comprising:
  (i) amplifying at least a portion of the purified target nucleic acid to generate an amplicon, such as by an isothermal amplification, such as whole genome amplification;
  (ii) immobilizing the amplicon to a second solid support by a method comprising contacting the amplicon with at least one immobilization probe, wherein:
    (α) the immobilization probe is bound to or adapted to be bound to the second solid support; and
    (β) at least a portion of the immobilization probe hybridizes the at least one target nucleic acid;
  (iii) contacting the immobilized amplicon with at least one detection probe, wherein the at least a portion of the detection probe hybridizes to the at least one target nucleic acid to generate a detection complex; and
  (iv) detecting at least a first detectable signal generated by the detection complex, wherein the detectable signal indicates the genotype of the target nucleic acid.

In another aspect, the purified nucleic acid is fragmented before amplification.

In another aspect, the second solid support generates the first detectable signal.

In another aspect, a plurality of distinct purified target nucleic acids are generated.

In another aspect, the plurality of purified target nucleic acids is contacted with a plurality of immobilization probes, wherein each of the plurality of immobilization probes is specific for a distinct purified target nucleic acid.

In another aspect, at least two of the plurality of immobilization probes are specific for the same purified target nucleic acid.

In another aspect, at least two of the plurality of immobilization probes are specific for different regions of the same purified target nucleic acid.

In another aspect, a plurality of distinct second solid supports are used, wherein: (α) each second solid support comprises at least one immobilization probe specific for a single target nucleic acid and does not comprise any immobilization probes specific for any other of the plurality of target nucleic acids; and (β) each solid support generates a unique first detectable signal that indicates the genotype of the target nucleic acid.

In another aspect, a second detectable signal is generated that indicates immobilization of the amplicon to the second solid support.

In another aspect, the detection probe comprises a detectable label that generates the second detectable signal.

In another aspect, the second detectable signal further indicates the genotype of the target nucleic acid.

In another aspect, the second detectable signal further indicates the quantity of amplicon immobilized to each solid support.

In another aspect, the first detectable signal indicates a genotype of a human papillomavirus (HPV) selected from the group consisting of: high-risk HPV (HR-HPV) types 16, 18, 26, 31, 33, 35, 39, 45, 51, 52, 56, 58, 59, 66, 68, and 82; and low-risk HPV (LR-HPV) types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, at least one of the purification probe, immobilization probe, and/or detection probe comprises an isolated nucleic acid having an overall length of not more than 100 nucleotides and comprising a sequence having at least 75-percent homology to a nucleotide sequence selected from the group consisting of SEQ ID NO: 1 to SEQ ID NO: 727, a DNA or RNA equivalent thereof, and a complement thereof.

In another aspect, the purification probe comprises a nucleotide sequence selected from the group consisting of SEQ ID NO: 1 to SEQ ID NO: 727 and a complement thereof.

In another aspect, the immobilization probe comprises a nucleotide sequence selected from the group consisting of SEQ ID NO: 344 to SEQ ID NO: 727 and a complement thereof.

In another aspect, the detection probe comprises a nucleotide sequence selected from the group consisting of SEQ ID NO: 1 to SEQ ID NO: 727 and a complement thereof.

In another aspect, a method is provided comprising:
a. a purifying step comprising:
  generating a double-stranded nucleic acid hybrid of the at least one target nucleic acid by hybridizing the at least one target nucleic acid to a hybrid probe set comprising at least a first nucleic acid probe specific for the at least one target nucleic acid;
  immobilizing the double-stranded nucleic acid hybrid to a first solid support through by contacting the double-stranded nucleic acid hybrid with at least a first antibody capable of binding to the double-stranded nucleic acid hybrid and binding the at least a first antibody to the first solid support; and
  separating the double-stranded nucleic acid hybrid from the sample to generate at least one purified nucleic acid;
b. an amplifying step, wherein at least a portion of the at least one purified nucleic acid is amplified to generate amplified nucleic acids; and
c. a genotyping step comprising:
  immobilizing the amplified nucleic acids to at least a second solid support by hybridizing the amplified nucleic acids to an immobilization probe set comprising at least one polynucleotide probe specific for the at least one target nucleic acid; and
  detecting the presence of the at least one target nucleic acid with a detection probe set comprising at least one polynucleotide probe specific for the at least one target nucleic acid.

In a further aspect, the amplification step comprises an isothermal amplification.

In a further aspect, the amplification step comprises whole genome amplification.

In a further aspect, the amplified nucleic acids are fragmented before the genotyping step.

In a further aspect, the immobilization probe set is bound to a plurality of solid supports placed in suspension.

In a further aspect, the plurality of solid supports is detectably labeled.

In a further aspect, the methods described herein are adapted to detect the presence of a plurality of target nucleic acids.

In a further aspect, the immobilization probe set comprises at least one probe specific for each of the plurality of target nucleic acids.

In a further aspect, the immobilization probe set consists essentially of two probes specific for each of the plurality of target nucleic acids.

In a further aspect, the two probes specific for of the plurality of target nucleic acids bind to distinct regions of the variants.

In a further aspect, each solid support of the plurality of solid supports contains only probes specific for one nucleic acid of the plurality of target nucleic acids, such that only the one nucleic acid of the plurality of target nucleic acids will bind to each of the plurality of solid supports.

In a further aspect, each of the plurality of solid supports is detectably labeled such that a solid support specific for a first nucleic acid of the plurality of target nucleic acids bears a different detectable label than a solid support specific for a second nucleic acid of the plurality of target nucleic acids.

In a further aspect, the detection probe set is detectably labeled.

In a further aspect, the detectable label of each of the plurality of solid supports is used to indicate the identity of the target nucleic acid bound thereto; and the detectable label of the detection probe set is used to indicate the relative amount of the target nucleic acid bound to each solid support.

In a further aspect, the at least one target nucleic acid is an human papillomavirus (HPV) nucleic acid.

In a further aspect, the HPV nucleic acid is selected from the group consisting of: high-risk HPV (HR-HPV) types 16, 18, 26, 31, 33, 35, 39, 45, 51, 52, 56, 58, 59, 66, 68, and 82; and low-risk HPV (LR-HPV) types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In a further aspect, a plurality of HPV nucleic acids are detected.

In a further aspect, the plurality of HPV nucleic acids comprises, consists, or consists essentially of: HR-HPV types 16, 18, 26, 31, 33, 35, 39, 45, 51, 52, 56, 58, 59, 66, 68, and 82, or any subset thereof; and/or LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

In a further aspect, the methods disclosed herein are adapted such that 59 high- and LR-HPV types can be detected and identified in a single reaction.

In another aspect, a kit for genotyping a nucleic acid is provided comprising: (a) an isolated nucleic acid as disclosed herein; (b) a nucleic acid polymerase; (c) a primer; (d) a first solid support; (e) an anti-DNA:RNA hybrid antibody bound to or adapted to be bound to the first solid support; and (f) a detectably labeled second solid support.

BRIEF DESCRIPTION OF THE DRAWINGS

FIG. 2 is a graph showing the results of a 20-plex reaction detecting quadruple HPV infections.

FIG. 6 is a data table displaying S/N values of multiplex experiment results testing for 26 HPV types and all HR-HPV types.

DETAILED DESCRIPTION

Figure 1A:
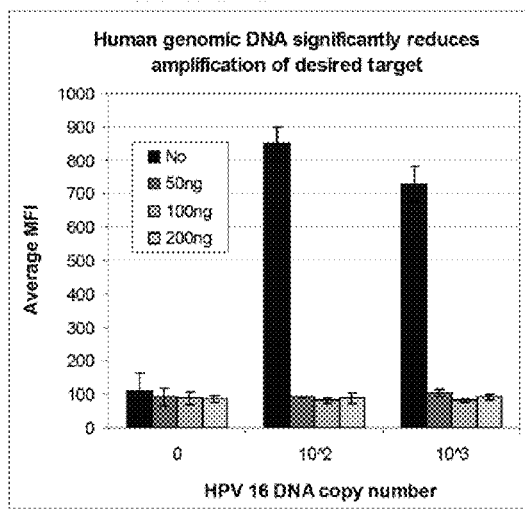
FIG. 1A is a graphical representation of conventional amplification results and how human genomic DNA reduces the amplification of the desired target.

The present disclosure covers methods, compositions, reagents, and kits for determining the presence of at least one target nucleic acid in a sample. The methods, compositions, reagents, systems, and kits may be used for clinical diagnostic purposes, including but not limited to the detection and identification of pathogenic organisms and the detection of a genetic predisposition to a particular disease.

I. Samples and Sample Preparation

A. Samples

Any sample may be used as a starting point, including, without limitation, a specimen or culture (e.g., cellular, microbiological and viral cultures) including clinical and laboratory biological and environmental samples. Biological samples may be from an animal, including a human, fluid, solid (e.g., stool) or tissue, as well as liquid and solid food and feed products and ingredients such as dairy items, vegetables, meat and meat by-products, and waste. Environmental samples include environmental material such as surface matter, soil, water and industrial samples, as well as samples obtained from food and dairy processing instruments, apparatus, equipment, utensils, disposable and non-disposable items.

Exemplary biological samples include, but are not limited to, cervical epithelial cells (e.g., a sample obtained from a cervical swab), adenoid cells, anal epithelial cells, blood, saliva, cerebral spinal fluid, pleural fluid, milk, lymph, sputum and semen.

In an aspect, the biological sample is collected and stored in a collection medium. The collection medium has several functions including as a preservative medium to preserve nucleic acids and inhibit nucleases to prevent degradation of nucleic acids prior to analysis. In one aspect, the collection medium is detergent-based. Without being limited, exemplary collection media include those found in U.S. Patent Publication No. US 2010-0105060 A1 and U.S. Patent Publication No. US 2010-0159463 A1, both of which are hereby incorporated by reference in their entirety.

In one aspect the detergent-based collection medium comprises, consists essentially of, or consists of 1.0% NP-40, 0.25% sodium deoxycholate, 50 mM Tris-HCl, 25 mM EDTA, 150 mM NaCl and 0.05% sodium azide. In another aspect the detergent-based collection medium comprises, consists essentially of, or consists of about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide. In other aspects the detergent-based collection medium comprises, consists essentially of, or consists of about 0.8% to about 1.5% NP-40, about 0.20% to about 0.40% sodium deoxycholate, about 30 mM to about 60 mM Tris-HCl, about 20 mM to about 40 mM EDTA, about 100 mM to about 200 mM NaCl, and about 0.025% to about 0.075% sodium azide. In yet another aspect the detergent-based collection medium comprises, consists essentially of, or consists of about 0.9% to about 1.2% NP-40, about 0.20% to about 0.30% sodium deoxycholate, about 30 mM to about 60 mM Tris-HCl, about 20 mM to about 30 mM EDTA, about 100 mM to about 150 mM NaCl, and about 0.04% to about 0.06% sodium azide.

In an aspect, the collection medium comprises, consists essentially of, or consists of NP-40 and EDTA. In another aspect, the collection medium comprises, consists essentially of, or consists of NP-40, EDTA, and sodium azide. In one aspect, the collection medium comprises, consists essentially of, or consists of sodium deoxycholate, EDTA, and sodium azide. In an aspect, the collection medium comprises, consists essentially of, or consists of about NP-40, sodium deoxycholate, EDTA, and sodium azide. In an aspect, the collection medium comprises, consists essentially of, or consists of NP-40, sodium deoxycholate, Tris-HCl, EDTA, and sodium azide.

In another aspect, the collection medium comprises, consists essentially of, or consists of 0.5% to about 2.0% NP-40 and 10 mM to about 50 mM EDTA. In another aspect, the collection medium comprises, consists essentially of, or consists of 0.5% to about 2.0% NP-40, 10 mM to about 50 mM EDTA, and about 0.01% to about 0.10% sodium azide. In one aspect, the collection medium comprises, consists essentially of, or consists of about 0.10% to about 0.40% sodium deoxycholate, 10 mM to about 50 mM EDTA, and about 0.01% to about 0.10% sodium azide. In an aspect, the collection medium comprises, consists essentially of, or consists of about 0.5% to about 2.0% NP-40, about 0.10% to about 0.40% sodium deoxycholate, 10 mM to about 50 mM EDTA, and about 0.01% to about 0.10% sodium azide. In an aspect, the collection medium comprises, consists essentially of, or consists of about 0.5% to about 2.0% NP-40, about 0.10% to about 0.40% sodium deoxycholate, about 25 mM to about 75 mM Tris-HCl, about 10 mM to about 50 mM EDTA, and about 0.01% to about 0.10% sodium azide. In certain aspects, the medium comprises or consists essentially of 1% NP-40, 0.25% sodium deoxycholate, 50 mM Tris-HCl, 25 mM EDTA, 150 mM NaCl and 0.09% sodium azide. This medium is often referred to herein as Digene Collection Medium or DCM.

Samples may be collected in other known collection mediums and can be used in the methods described herein. Examples of other collection media include PRESERVCYT, SUREPATH, urine, and STM (Sample/Specimen Transport Medium). Samples collected in some of these media may require processing before the nucleic acids in the samples can be detected and analyzed. Various methods of processing samples (also known as preparing the samples) are known in the art. For example, cervical cell samples collected for cytological analysis in medium such as PRESERVCYT may be combined with a detergent-based lysis buffer followed by the addition of magnetic beads comprising nucleic acid binding surfaces.

In another aspect, the sample may comprise, consist, or consist essentially of nucleic acids that have been extracted from a biological sample. Numerous methods are known for extracting nucleic acids from a biological or environmental sample, including but not limited to: phenol/chloroform extraction; anion exchange chromatography; cesium chloride gradient ultracentrifugation; size exclusion chromatography; and silca/chaotropic salt extraction. Extracted nucleic acids may be further separated according to size by gel electrophoresis and extracted from the gel if samples comprising specific nucleic acid sizes are desired.

B. Target Nucleic Acids

As noted above, the methods disclosed herein relate to the detection and genotyping of at least one target nucleic acid in a sample. The at least one target nucleic acid may be DNA or RNA or both DNA and RNA and can be single-stranded, double-stranded, or partially single-stranded. The at least one target nucleic acid can be contained within a larger nucleic acid. Detection of either the at least one target nucleic acid or the larger nucleic acid comprising the at least one target nucleic acid is contemplated by this disclosure.

The at least one target nucleic acids may include, without limitation, nucleic acids found in specimens or cultures (e.g., cellular, microbiological and viral cultures) including biological and environmental samples. The at least one target nucleic acids may be found in biological samples from an animal, including a human, fluid, solid (e.g., stool) or tissue, as well as liquid and solid food and feed products and ingredients such as dairy items, vegetables, meat and meat by-products, and waste. At least one target nucleic acids may be found in environmental samples and include environmental material such as surface matter, soil, water and industrial samples, as well as samples obtained from food and dairy processing instruments, apparatus, equipment, utensils, disposable and non-disposable items.

The at least one target nucleic acids found in biological samples include, but are not limited to, cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen. The at least one target nucleic acids may be from other viral, bacteria, mycobacteria or plasmodia, such as cytomegalovirus (CMV), herpes simplex virus (HSV), human immunodeficiency virus (HIV), H1N1, *Neisseria gonorrhoeae* (GC), *Chlamydia trachomatis* (CT), *Trichomonas vaginalis, Staphylococcus aureus, mycobacterium tuberculosis*, SARS-associated coronavirus or influenza.

In an aspect the at least one target nucleic acids are at least 75%, at least 80%, at least 85%, at least 90%, at least 95%, at least 96%, at least 97%, at least 98%, at least 98%, at least 99%, or 100% identical to nucleic acids associated with any one of cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen, other viral, bacteria, mycobacteria or plasmodia, for example cytomegalovirus (CMV), herpes simplex virus (HSV), human immunodeficiency virus (HIV), H1N1, *Neisseria gonorrhoeae* (GC), *Chlamydia trachomatis* (CT), *Trichomonas vaginalis, Staphylococcus aureus, mycobacterium tuberculosis*, SARS-associated coronavirus or influenza.

In one aspect, the at least one target nucleic acid is an HPV nucleic acid. In another aspect, the HPV nucleic acid is HPV DNA of a HR-HPV type. In another aspect, the HPV nucleic acid is HPV RNA of a LR-HPV type. In another aspect the at least one target nucleic acids are any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of target nucleic acid is targeted. In one aspect, the plurality of target nucleic acids consists of a set of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleic acids having distinct nucleotide sequences. Any set of nucleic acids to be targeted can be used. In one aspect, the plurality of target nucleic acids is selected such that each is related to the others. By way of example and not limitation, the set of nucleic acids can be: structurally related to one another (for example, members of a gene family); functionally related to one another (for example, nucleic acids encoding proinflammatory cytokines); phylogenetically related to one another (for example, nucleic acids specific for different members of a family of viruses, such as HPV-family viruses); related by virtue of differential expression in a different cell or tissue type (for example, macrophage-associated nucleic acids and prostate-associated nucleic acids) or disease states (cervical cancer associated nucleic acids). In another aspect, the set of nucleic acids is unrelated.

In one aspect, a set of target nucleic acids comprises, consists, or consists essentially of HR-HPV types 16, 18, 26, 31, 33, 35, 39, 45, 51, 52, 56, 58, 59, 66, 68, and 82, or any subset thereof. In another aspect, a set of target nucleic acids comprises, consists, or consists essentially of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In another aspect a set of target nucleic acids comprises, consists, or consists essentially of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In another aspect, the at least one target nucleic acid is at least 75%, at least 80%, at least 85%, at least 90%, at least 95%, at least 96%, at least 97%, at least 98%, at least 98%, at least 99%, or 100% identical to nucleic acids associated with any one of HPV, genetic variants of HPV, HPV DNA of a HR-HPV type, or HPV RNA of a HR-HPV type. In another aspect the at least one target nucleic acids are at least 75%, at least 80%, at least 85%, at least 90%, at least 95%, at least 96%, at least 97%, at least 98%, at least 98%, at least 99%, or 100% identical to nucleic acids associated with any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

As noted previously, the at least one target nucleic acid may be DNA or RNA. When the at least one target nucleic acid is DNA, the probe can be RNA and when the at least one target nucleic acid is RNA, the probe is can be DNA. However, a DNA probe can be used with DNA at least one target nucleic acid and an RNA probe can be used with RNA at least one target nucleic acid.

C. Sample Preparation

After the sample is collected in a collection medium as described above, the sample may be treated with a denaturation reagent to render the at least one target nucleic acid accessible to hybridization. In one aspect, the sample is denatured with an alkaline solution. Without being limited, suitable alkali include NaOH and KOH.

Alkaline treatment of protein effectively homogenizes the specimen to ensure reproducibility of analysis results for a given sample. It can also reduce the viscosity of the sample to increase kinetics, homogenize the sample, and reduce background by destroying any endogenous single stranded RNA nucleic acids, DNA-RNA hybrids or RNA-RNA hybrids in the sample. It also helps inactivate enzymes such as RNases and DNases that may be present in the sample. One skilled in that art would appreciate that if RNA is the at least one target nucleic acid (as opposed to DNA), different reagents may be preferable including, but not limited to phenol extraction and TCA/acetone precipitation, and guanidinium thiocyanate-phenol-chloroform extraction.

Other methods of denaturation may be employed such as utilizing a heating step, for example, heating the sample to about 95° C. to separate the strands of nucleic acid. Enzymes such as helicase may be used as well.

II. Purification

In the typical assay to detect nucleic acids in a sample, a large, non-specific extraction of nucleic acids is performed. The user then attempts to amplify or detect the target nucleic acid in the presence of this large pool of non-specific nucleic acids. However, the non-specific pool of nucleic acids oftentimes interferes with the amplification or detection step desired, particularly when the target nucleic acid is at a low concentration compared to the non-specific nucleic acids. The presently disclosed methods therefore separate the target nucleic acid from the non-specific pool of nucleic acid before the detection is performed by: (1) hybridizing a sequence specific polynucleotide purification probe to the target nucleic acid to form a double-stranded nucleic acid hybrid; (2) complexing the double-stranded nucleic acid hybrid to at least one molecule that specifically binds to double-stranded nucleic acid hybrids; and (3) capturing the complex to a solid support.

A. Hybridization of Probes

After the sample comprising the nucleic acid is prepared for hybridization, it is contacted with at least one polynucleotide hybrid probe under a condition sufficient for the one or more polynucleotide hybrid probes to hybridize to the at least one target nucleic acid in the sample to form a double-stranded nucleic acid hybrid. The at least one polynucleotide hybrid probe can be full length, truncated, or synthetic DNA or full length, truncated, or synthetic RNA. If the at least one target nucleic acid is DNA, then the at least one polynucleotide hybrid probe may be RNA and if the at least one target nucleic acid is RNA, then the probe may be DNA.

In one aspect, a single polynucleotide probe is used to purify the target nucleic acid. The single polynucleotide probe may be specific for only a single target nucleic acid or may be designed so as to hybridize to a plurality of target nucleic acids under stringent conditions. By way of example and not limitation, a polynucleotide probe may be designed against a highly conserved region of nucleic acids encoding a specific gene product, such that the polynucleotide probe would be expected to hybridize under stringent conditions to substantially all nucleic acids encoding that gene product.

In another aspect, a plurality of polynucleotide probes is used to purify the target nucleic acid. The plurality of polynucleotide probes may be specific for only a single target nucleic acid or may be specific for a plurality of target nucleic acids. By way of example and not limitation, a plurality of polynucleotide probes specific for a single target nucleic acid may be generated by fragmenting the target nucleic acid. In one aspect, at least one polynucleotide hybrid probes is provided for each target nucleic acid. In another aspect, at least two polynucleotide hybrid probes are provided for each target nucleic acid.

In an aspect, the polynucleotide hybrid probe is capable of hybridizing or binding to nucleic acids at least 75%, at least 80%, at least 85%, at least 90%, at least 95%, at least 96%, at least 97%, at least 98%, at least 98%, at least 99%, or 100% identical to nucleic acids associated with HPV, genetic variants of HPV, HPV DNA of a HR-HPV type, or HPV RNA of a HR-HPV type, or any one of one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91. In another aspect, the probe is complementary to HPV, genetic variants of HPV, HPV DNA of a HR-HPV type, HPV RNA of a HR-HPV type, or any one of one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of polynucleotide hybrid probes is provided, the plurality being selected to hybridize to and purify each of a set of target nucleic acids. In one aspect, the plurality of polynucleotide hybrid probes is capable of hybridizing to each nucleic acid of a set of target nucleic acids consisting of HR-HPV types 16, 18, 26, 31, 33, 35, 39, 45, 51, 52, 56, 58, 59, 66, 68, and 82 nucleic acids, or any subset thereof. In one aspect, the plurality of polynucleotide hybrid probes is capable of hybridizing to each nucleic acid of a set of target nucleic acids consisting of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In one aspect, the plurality of polynucleotide hybrid probes is capable of hybridizing to each nucleic acid of a set of target nucleic acids consisting of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

If the at least one target nucleic acid was denatured using an alkaline treatment, the one or more polynucleotide probes may be diluted in a probe diluent that also can act as a neutralizing hybridization buffer (to neutralize the basic denaturation reagent).

The probe diluent used for DNA or RNA probes will differ due to the different requirements necessary for DNA versus RNA stability. For example, if the probes are RNA, it is preferable to neutralize the sample first and then add the probe or alternatively, add the RNA probe and neutralizing agent (probe diluent) to the sample at the same time as excessive alkalinity can destroy RNA. The probe diluent can be used to dissolve and dilute the probe and also help restore the sample to about a neutral pH, e.g., about pH 6 to about pH 9, to provide a more favorable environment for hybridization. Sufficient volume of probe diluent, preferably one-half volume of the sample, may be used to neutralize the base-treated sample.

For full length probes, a heated alkaline solution may be added to the sample, then probe diluent may be added to the sample at room temperature, and then the sample may be reheated. Such a process can inhibit secondary structure from forming. Antibodies tend to irreversibly bind to structures with secondary structure. When using non-full length probes such as truncated or synthetic probes, heating the solutions or sample may not be necessary because secondary structures issues are not present. In an aspect, the sample is not heated when used with truncated or synthetic probes.

After treatment with the denaturation reagent, an aliquot of neutralization buffer, in an aspect the probe diluent described, in which the one or more probes are dissolved, can be added to the sample under appropriate conditions to allow hybridization or binding of the probe and the at least one target nucleic acid to occur. The neutralization buffer may contain a single buffering salt. In an aspect, the neutralization buffer does not contain more than a single buffering salt. The hybridization condition is sufficient to allow the one or more polynucleotide probes to anneal to a corresponding complementary nucleic acid sequence, if present, in the sample to form a double-stranded nucleic acid hybrid.

Hybridization conditions suitable for the particular probes and diluents described herein are employed. For example, the probes and sample nucleic acids can be incubated for a hybridization time, preferably at least about 5 to about 30 minutes, about 5 to about 20 minutes, or from about 7 to about 15 minutes, or about 10 minutes, as well as any number within the recited ranges sufficient to allow the one or more polynucleotide probes to anneal to a corresponding complementary nucleic acid sequence. The hybridization condition can include a hybridization temperature of at least about 65° C., about 68.5° C., and about 67° C. to about 70° C., as well as any number within the recited ranges. For a given at least one target nucleic acid and a given probe, one of ordinary skill in the art can readily determine desired hybridization conditions by routine experimentation. One of ordinary skill in the art will further appreciate that the time and temperature of hybridization must be optimized, one with respect to the other. Thus, higher hybridization temperatures may be carried out for shorter periods of time and vice versa. Without being limited, stringent hybridization conditions may be controlled by increasing the temperature, increasing the ionic conditions to above 0.5M (for example, NaCl), or reducing the concentration of PAA. As a non-limiting example, stringent hybridization conditions may include performing a hybridization reaction at elevated temperatures, such as of at least about 65° C., at least about 68.5° C., between about 67° C. to about 70° C., and between about 69° C. to about 70° C. Stringent hybridization conditions may also include elevated temperatures, such as of at least about 65° C., at least about 68.5° C., and between about 67° C. to about 70° C. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995), incorporated by reference in its entirety.

For present purposes, "stringent conditions" encompass conditions under which hybridization will only occur if there is 25% mismatch or less between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. Calculations regarding hybridization conditions required for attaining particular degrees of stringency are also discussed by Sambrook et al. (ed.), Molecular Cloning: A Laboratory Manual, 2nd ed., vol. 1-3, Cold Spring Harbor Laboratory Press, Cold Spring Harbor, N.Y., 1989, chapters 9 and 11, herein incorporated by reference in its entirety.

In an aspect, the hybridization/capture step is completed at 50° C. in about 15-25 minutes; at 50° C. in about 20-25 minutes; or at 50° C. in about 22.5 minutes.

In one aspect, the sample is suspended in collection medium, the at least one target nucleic acid is denatured with a denaturation reagent, and hybridized to nucleic acid probes suspended in a neutralizing buffer. In another aspect the neutralizing buffer is the probe diluent of the present invention. In another aspect, the probe diluent comprises 2.2 M BES (N,N-bis(2-hydroxyethyl)-2-aminoethanesulfonic acid), 2.6% polyacrylic acid, 0.7 N NaOH and 0.05% sodium azide.

B. Complexing and Capturing the Double-Stranded Nucleic Acid Hybrid

After the probes are allowed to hybridize to the at least one target nucleic acid and form a double-stranded nucleic acid hybrid, the hybrid is captured by a molecule that is specific for the double-stranded nucleic acid hybrid. Molecules specific for the double-stranded nucleic acid hybrids include, but are not limited to, monoclonal antibodies, polyclonal antibodies, proteins such as but not limited to RNAse H, nucleic acids including but not limited to aptamers, or sequence specific nucleic acids. Aptamers are short stretches of random sequences that are successively selected from a library of sequences by hybridizing to a target, amplifying the hybridized aptamers, and repeating the selection process.

In one aspect the molecule specific for the double-stranded nucleic acid hybrid is captured by an antibody, known as an anti-hybrid antibody. In another aspect, the anti-hybrid antibodies are immobilized onto a support before the double-stranded nucleic acid hybrid is captured. Methods of immobilizing antibodies to solid supports are well known in the art. By way of example and not limitation, the antibodies can be covalently linked to the solid support. As another example, the antibody can be adsorbed onto the adsorption, for example, protein-protein interactions, protein-G beads, biotin-streptavidin interaction, EDAC to link to a carboxyl or tosyl group, etc., or hybridization directly onto the solid support using, for example, sequence specific nucleic acids in an affinity column.

In another aspect, the anti-hybrid antibodies may be complexed with the double-stranded nucleic acid hybrid before being immobilized on the solid support. By way of example and not limitation the anti-hybrid antibody may be conjugated with a biotin label, while the support may be conjugated with a streptavidin moiety. Anti-hybrid antibody/double-stranded nucleic acid-hybrid complexes can then be allowed in the absence of the solid support. When the solid support is added to the reaction mixture, the anti-hybrid antibody/double-stranded nucleic acid-hybrid complexes will be immobilized to the solid support by virtue of the interaction between the biotin conjugate and the streptavidin moiety.

Supports include but are not limited to beads; magnetic beads, including paramagnetic, diamagnetic, ferromagnetic, ferrimagnetic, and diamagnetic beads, columns, plates, filter paper, polydimethylsiloxane (PDMS); dipsticks; coated tubes, plates, and dishes; and resin columns. Any support can be used as long as it allows extraction of the liquid phase and provides the ability to separate out bound and unbound antibodies. Paramagnetic beads are particularly useful in that they can be left in the solution and the liquid phase can be extracted or decanted, if a magnetic field is applied to immobilize the beads. Beads that are small and have a high surface area are preferable, such as beads about 1 µm in diameter. Other beads that employ charge switching or silica capture (as opposed to magnetic fields) may be used as well.

The hybrids are incubated with the anti-hybrid antibody attached to the support for a sufficient amount of time to allow capture of the double-stranded nucleic acid hybrids by the immobilized anti-hybrid antibodies. In an aspect, the support is a bead.

The anti-hybrid antibody may be monoclonal or polyclonal. In one aspect the antibody is monoclonal. In one aspect, the antibody is coupled to the support by a 1-ethyl-3-[3-dimethylaminopropyl]carbodiimide hydrochloride (EDAC) linker. In one aspect, the support is a polystyrene bead. In an aspect, the support or bead coupled to the antibody is diluted in a bead dilution buffer. The bead dilution buffer is helpful in minimizing protein denaturation on the bead. One example of a bead dilution buffer comprises 6% casein, 100 mM Tris-HCl, 300 mM NaCl, and 0.05% sodium azide.

In an aspect, the beads coated with the anti-hybrid antibody are incubated with the sample at about 67° C. to about 70° C. for about 30 minutes. In another aspect, the beads and sample are incubated at about 68° C. to about 69° C. for about 30 minutes. In yet another aspect, the beads and sample are incubated at about 68.5° C. for 30 minutes. The incubation time can range from about 5 minutes to about 60 minutes, from about 15 minutes to about 45 minutes, from about 20 minutes to about 40 minutes, or any number within the recited ranges, and is generally inversely proportional to the temperature. It will be understood by those skilled in the art that the incubation time, temperature and/or shaking conditions can be varied to achieve alternative capture kinetics as desired.

Following capture of the at least one target nucleic acid/probe hybrid as described above, the captured hybrid may be separated from the rest of the sample by washing away of non-captured nucleic acids.

III. Amplification

Once the at least one target nucleic acid is purified, it is amplified. Amplification is performed at this time to increase the sensitivity of the method by increasing the amount of the at least one target nucleic acid.

Nucleic acid amplifications can be broadly separated into two categories: temperature cycled amplifications and isothermic amplifications.

In temperature cycled amplifications, the temperature typically is raised above the melting point of the target nucleic acid to "melt" any double stranded portions, and then lowered to a point at which oligonucleotide primers anneal with single stranded portion of the target nucleic acid, then raised again to a temperature at which the primers remain annealed and the polymerase is active.

In isothermic amplifications, an agent is added to the reaction mixture to permit amplification without temperature cycling. For example, in helicase-dependant amplification ("HDA"), an enzyme having helicase activity is added to the amplification mixture. As used herein, "helicase" or "an enzyme with, or having, helicase activity" refers to any enzyme capable of unwinding a double stranded nucleic acid. The helicase functions to unwind double stranded nucleic acids, thus obviating the need for repeated melting cycles. Examplary helicases include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful include RecQ helicase, thermostable UvrD helicases from *T. tengcongensis* and *T. thermophilus*, thermostable DnaB helicase from *T. aquaticus*, and MCM helicase from archaeal and eukaryotic organisms. As another example, in nick-initiated amplification ("NIA"), a nick-inducing agent is used to induce breaks in the phosphodiester bonds of the nucleic acid backbone. A polymerase having strand displacement activity can then initiate amplification at the site of the nick, using one strand of the nucleic acid as a primer and the other strand as a template. As used herein, "nick-inducing agent" refers to any enzymatic or chemical reagent or physical treatment that introduces breaks in the phosphodiester bond between two adjacent nucleotides in one strand of a double-stranded nucleic acid. Examples of nick-inducing enzymes include Bpu10 I, BstNB I, Alw I, BbvC I, BbvC I, Bsm I, BsrD, and *E. coli* endonuclease I.

The amplification in the disclosed methods can be either a temperature cycled amplification or an isothermic amplification. Exemplary methods of amplification include, but are not limited to: polymerase chain reaction ("PCR"), reverse transcriptase ("RT") reaction, RT-PCR, HDA, RT-HDA, thermophilic helicase-dependent amplification ("tHDA"), RT-tHDA, whole genome amplification ("WGA"), RT-WGA, ligase chain reaction ("LCR"), RT-LCR, NIA, and RT-NIA.

Amplification reactions can further be separated into sequence-dependent or sequence-independent amplifications.

"Sequence-dependent amplification" refers to amplification of a target sequence relative to non-target sequences present in a sample with the use of target-specific primers. As used herein, "target-specific primer" refers to a single stranded nucleic acid capable of binding to a pre-determined single stranded region on a target nucleic acid to facilitate polymerase dependent replication of the target nucleic acid to be selectively amplified.

In one aspect, the amplification is a sequence-specific amplification. In another aspect, a pair of target-specific primers, one hybridizing to the 5'-flank of a target sequence within each target nucleic acid and the other hybridizing to the 3'-flank of the target sequence, are used to achieve exponential amplification of the target sequence. Thus arrangement is useful where all of the target nucleic acids comprise a variable region that is sought to be genotyped and where the variable region is flanked on both sides by conserved regions. In another aspect, multiple pairs of target-specific primers are utilized in a single reaction for amplifying multiple targets nucleic acids simultaneously.

Generally, suitable target-specific primer pairs are short synthetic oligonucleotides, for example having a length of more than 10 nucleotides and less than 50 nucleotides. Target-specific, oligonucleotide primer design involves various parameters such as string-based alignment scores, melting temperature, primer length and GC content. When designing a target-specific primer, one of the important factors is to choose a sequence within the target fragment that is specific to the nucleic acid molecule to be amplified. Another important factor is to calculate the melting temperature of a target-specific primer for the reaction. The melting temperature of a target-specific primer is determined by the length and GC content of that oligonucleotide. Preferably the melting temperature of a primer is about 10 to 30° C. higher than the temperature at which primer hybridization and target amplification will take place.

"Primer hybridization" refers to binding of an oligonucleotide primer to a region of the single-stranded nucleic acid template under the conditions in which the primer binds only specifically to its complementary sequence on one of the template strands, not other regions in the template. The specificity of hybridization may be influenced by the length of the oligonucleotide primer, the temperature in which the hybridization reaction is performed, the ionic strength, and the pH of the reaction mixture.

Each target-specific primer hybridizes to each end of the target nucleic acid and may be extended in a 3'→5' direction by a polymerase using the target nucleotide sequence as a template. To achieve specific amplification, a homologous or perfect match target-specific primer is preferred. However, target-specific primers may include sequences at the 5' end which are non-complementary to the target nucleotide sequence(s). Alternatively, target-specific primers may contain nucleotides or sequences throughout that are not exactly complementary to the target nucleic acid.

The target-specific primers may include any of the deoxyribonucleotide bases A, T, G or C and/or one or more ribonucleotide bases, A, C, U, G and/or one or more modified nucleotide (deoxyribonucleotide or ribonucleotide) wherein the modification does not prevent hybridization of the primer to the nucleic acid or elongation of the target-specific primer or denaturation of double stranded molecules. Target-specific primers may be modified with chemical groups such as phosphorothioates or methylphosphonates or with non nucleotide linkers to enhance their performance or to facilitate the characterization of amplification products.

In general, the temperature of denaturation suitable for permitting specificity of target-specific primer-template recognition and subsequent annealing may occur over a range of temperatures, for example 20° C. to 75° C. A preferred denaturation temperature may be selected according to which helicase is selected for the melting process. Tests to determine optimum temperatures for amplification of a nucleic acid in the presence of a selected helicase can be determined by routine experimentation by varying the temperature of the reaction mixture and comparing amplification products using gel electrophoresis.

In a further aspect, amplification is a sequence-independent amplification. As used herein, "sequence-independent amplification" refers to any amplification that does not amplify a specific sequence. By way of example and not limitation, random primer mixtures or nick-inducing agents may be used to initiate sequence-independent amplification.

As used herein, "random primer mixture" refers to mixtures of short randomly generated oligonucleotide sequences.

As used herein, "nick-initiated polymerase activity" refers to polymerase activity in the absence of exogenous primers, which is initiated by single-strand breaks in the template. Synthesis initiates at the single-strand break in the DNA, rather than at the terminus of an exogenous synthetic primer. With nick-initiated synthesis, removal of primers is unnecessary, reducing cost, handling time and potential for loss or degradation of the product. In addition, nick-initiated synthesis reduces false amplification signals caused by self-extension of primers. The nicks may be introduced at defined locations, by using enzymes that nick at a recognition sequence, or may be introduced randomly in a target polynucleotide. As used herein, "nick-inducing agent" refers to any enzymatic or chemical reagent or physical treatment that introduces breaks in the phosphodiester bond between two adjacent nucleotides in one strand of a double-stranded nucleic acid. Examples of nick-inducing enzymes include Bpu10 I, BstNB I, Alw I, BbvC I, BbvC I, Bsm I, BsrD, and E. coli endonuclease I. In one aspect, at least one nick-inducing enzyme is included as a replacement for a helicase in a reaction mixture. In another aspect, at least one nick-inducing enzyme is added to a reaction mixture in addition to at least one helicase.

In one aspect, the amplification is an isothermic amplification. In another aspect, the isothermic amplification is a Whole Genome Amplification ("WGA"). WGA is an isothermal process that uses non-specific primers to generate amplicons using the target nucleic acid sequence as a template. As multiple random primers are used, substantially the entire molecule comprising the target nucleic acid can be amplified using WGA. For example, Phi 29 DNA polymerase can be used in combination with non-specific primers to amplify target nucleic acid sequences. The polymerase can move along the target nucleic acid sequence displacing the complementary strand. The displaced strand becomes a template for replication allowing high yields of high-molecular weight DNA to be generated. In one aspect, the WGA reaction is modified to include at least one helicase, at least one nick-inducing agent, or both.

In a further aspect, the amplicons generated by the amplification step can be fragmented after amplification.

IV. Genotyping

A. Capture

After the at least one target nucleic acid is amplified, it is contacted with at least one polynucleotide probe under a condition sufficient for the one or more polynucleotide capture probes to hybridize to the at least one target nucleic acid. The at least one polynucleotide capture probe can be full length, truncated, or synthetic DNA or full length, truncated, or synthetic RNA.

Where a plurality of target nucleic acids are desired to be genotyped, at least one polynucleotide capture probe specific for each target nucleic acid should be provided. In an aspect, a plurality of polynucleotide probes is used to purify the target nucleic acid. The plurality of polynucleotide probes may consist of only a single nucleic acid probe specific for each target nucleic acid or may consist of a plurality of nucleic acid probes specific for each target nucleic acid. In one aspect, 1, 2, 3, 4, 5, 6, 7, 8, 9, or 10 polynucleotide capture probes specific for each single target nucleic acid may be provided. In another aspect, each polynucleotide capture probe is selected such that it is specific only for one target nucleic acid and does not cross-react with any other target nucleic acid in stringent conditions. In yet another aspect, at least two polynucleotide capture probes are provided for each target nucleic acid, wherein each polynucleotide capture probe hybridizes to a distinct region of the target nucleic acid. By way of example, where the target nucleic acids comprise HPV nucleic acids, at least one polynucleotide capture probe may be selected to hybridize to each of the E6/E7 and L1 regions of each HPV nucleic acid to be tested.

The polynucleotide capture probes can be adapted to be immobilized to a second solid support. In one aspect, the polynucleotide capture probes are immobilized to the second solid support before they are hybridized to the at least one target nucleic acid. Supports include but are not limited to beads; magnetic beads, including paramagnetic, diamagnetic, ferromagnetic, ferrimagnetic, and diamagnetic beads; columns; plates; filter paper; polydimethylsiloxane (PDMS); dipsticks; tubes; dishes; mica chips.

In a further aspect, the second solid support comprises beads. In one aspect, a plurality of beads are provided, wherein each bead of the plurality immobilizes only polynucleotide capture probes specific for only a single target nucleic acid, such that each bead will specifically immobilize only a single target nucleic acid. In a further aspect, each bead of the plurality bears a detectable label, wherein the detectable label corresponds to the genotype of the target nucleic acid for which the bead is specific.

In one aspect, polystyrene microspheres are provided as the second solid support. Polystyrene microspheres can be filled with various dyes, permitting each individual microsphere to be detectably labeled. In one aspect, polystyrene microspheres marketed under the brand name Luminex® are used. Luminex® microspheres are internally dyed with various concentrations of red and infrared fluorophores, such that 100 different spectral signatures can be generated. In this way, microspheres specific for 100 different target nucleic acids may be generated by immobilizing polynucleotide capture probes specific for a single target nucleic acid to a set of beads with a single identifiable label.

In an aspect, the polynucleotide capture probe is capable of hybridizing or binding to nucleic acids at least 75%, at least 80%, at least 85%, at least 90%, at least 95%, at least 96%, at least 97%, at least 98%, at least 98%, at least 99%, or 100% identical to nucleic acids associated with HPV, genetic variants of HPV, HPV DNA of a HR-HPV type, or HPV RNA of a HR-HPV type, or any one of one of HR-HPV types 16, 18, 26, 31, 33, 35, 39, 45, 51, 52, 56, 58, 59, 66, 68, and 82; or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91. In another aspect, the immobilization probe is complementary to HPV, genetic variants of HPV, HPV DNA of a HR-HPV type, HPV RNA of any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of polynucleotide capture probes is provided, the plurality being selected to hybridize to each of a set of target nucleic acids. In one aspect, the plurality of polynucleotide capture probes is capable of hybridizing to each nucleic acid of a set of target nucleic acids consisting of HR-HPV types 16, 18, 26, 31, 33, 35, 39, 45, 51, 52, 56, 58, 59, 66, 68, and 82 nucleic acids, or any subset thereof. In one aspect, the plurality of polynucleotide capture probes is capable of hybridizing to each nucleic acid of a set of target nucleic acids consisting of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In one aspect, the plurality of polynucleotide capture probes is capable of hybridizing to each nucleic acid of a set of target nucleic acids consisting HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In a further aspect, a plurality of second solid supports is provided, consisting of solid supports specific for each nucleic acid of a set of target nucleic acids consisting of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

Hybridization conditions suitable for the particular probes and diluents described herein are employed. For example, the probes and sample nucleic acids can be incubated for a hybridization time, preferably at least about 5 to about 30 minutes, about 5 to about 20 minutes, or from about 7 to about 15 minutes, or about 10 minutes, as well as any number within the recited ranges sufficient to allow the one or more polynucleotide probes to anneal to a corresponding complementary nucleic acid sequence. The hybridization condition can include a hybridization temperature of at least about 65° C., about 68.5° C., and about 67° C. to about 70° C., as well as any number within the recited ranges. For a given at least one target nucleic acid and a given probe, one of ordinary skill in the art can readily determine desired hybridization conditions by routine experimentation. One of ordinary skill in the art will further appreciate that the time and temperature of hybridization must be optimized, one with respect to the other. Thus, higher hybridization temperatures may be carried out for shorter periods of time and vice versa. Without being limited, stringent hybridization conditions may be controlled by increasing the temperature, increasing the ionic conditions to above 0.5M (using, for example, NaCl), or reducing the concentration of PAA. As a non-limiting example, stringent hybridization conditions may include performing a hybridization reaction at elevated temperatures, such as of at least about 65° C., at least about 68.5° C., between about 67° C. to about 70° C., and between about 69° C. to about 70° C. Stringent hybridization conditions may also include elevated temperatures, such as of at least about 65° C., at least about 68.5° C., and between about 67° C. to about 70° C.

B. Detection

In one aspect, the immobilization probe forms a DNA:RNA hybrid with the amplicon when hybridized thereto. In such a circumstance, detection may be performed using a by providing a second antibody that is also specific for double-stranded DNA:RNA hybrids. The second antibody may be detectably labeled, either directly or indirectly, and may be a monoclonal or polyclonal antibody.

Alternatively, the amplicon may be further hybridized to at least one polynucleotide detection probe specific for the at least one target nucleic acid. The detection probe may be DNA, RNA, synRNA, or PNA and may optionally be detectably labeled. In one aspect, the detectable label is biotin, which may be detected by conjugating the biotin with a streptavidin labeled with a fluorophore, including phycoerythrin.

In one aspect, each detection probe is specific for only a single target nucleic acid and does not cross-react with another target nucleic acid.

In another aspect, a plurality of polynucleotide detection probes is used. The plurality of polynucleotide probes may consist of only a single nucleic acid probe specific for each target nucleic acid or may consist of a plurality of nucleic acid probes specific for each target nucleic acid. In one aspect, 1, 2, 3, 4, 5, 6, 7, 8, 9, or 10 polynucleotide capture probes may be provided that are specific for each single target nucleic acid. In another aspect, each polynucleotide capture probe is selected such that it is specific only for one target nucleic acid and does not cross-react with any target nucleic acid in stringent conditions. In yet another aspect, at least two polynucleotide capture probes are provided for each target nucleic acid, wherein each polynucleotide capture probe hybridizes to a distinct region of the target nucleic acid. By way of example, where the target nucleic acids comprise HPV nucleic acids, at least one polynucleotide may be chosen for each of the E6/E7 and L1 regions of the HPV nucleic acid.

In another aspect, a single polynucleotide detection probe is provided that is capable of hybridizing with all of the target nucleic acids under stringent conditions.

In an aspect, the polynucleotide detection probe is capable of hybridizing or binding to nucleic acids at least 75%, at least 80%, at least 85%, at least 90%, at least 95%, at least 96%, at least 97%, at least 98%, at least 98%, at least 99%, or 100% identical to nucleic acids associated with HPV, genetic variants of HPV, HPV DNA of a HR-HPV type, or HPV RNA of a HR-HPV type of HR-HPV types 16, 18, 26, 31, 33, 35, 39, 45, 51, 52, 56, 58, 59, 66, 68, or 82, or LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, or 91. In another aspect, the detection probe is complementary to HPV, genetic variants of HPV, HPV DNA of a HR-HPV type, HPV RNA of a HR-HPV type, or any one of HR-HPV types 16, 18, 26, 31, 33, 35, 39, 45, 51, 52, 56, 58, 59, 66, 68, and 82; or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of polynucleotide detection probes is provided, the plurality being selected to hybridize to each of a set of target nucleic acids. In one aspect, the plurality of polynucleotide detection probes is capable of hybridizing to each nucleic acid of a set of target nucleic acids consisting of HR-HPV types 16, 18, 26, 31, 33, 35, 39, 45, 51, 52, 56, 58, 59, 66, 68, and 82 nucleic acids, or any subset thereof. In one aspect, the plurality of polynucleotide detection probes is capable of hybridizing to each nucleic acid of a set of target nucleic acids consisting of LR-HPV types 6, 11, 40, 43, 53, 61, 67, 69, 70, 71, 72, 81, and 83. In one aspect, the plurality of polynucleotide detection probes is capable of hybridizing to each nucleic acid of a set of target nucleic acids consisting of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

In another aspect, each polynucleotide detection probe bears the same detectable label.

In another aspect, the polynucleotide detection probes are used to generate double stranded nucleic acid hybrids, which can then be detected by providing a second antibody that is also specific for double-stranded nucleic acids hybrids. The second antibody may be detectably labeled, either directly or indirectly, and may be a monoclonal or polyclonal antibody. In an aspect, the second antibody is monoclonal. In another aspect, the second antibody is directly labeled with a detectable marker and is monoclonal. The second antibody is used to detect the presence of double-stranded nucleic acid hybrids. In one aspect, the second antibody has a label that must react with a substrate to provide a signal that can be detected. The second antibody may be dissolved in a suitable buffer. In one aspect the buffer comprises 100 mM TrisHCl, pH 7.4, 0.5 M NaCl, 0.1 mM ZnCl2, 1.0 mM MgCl2, 0.25% Tween 20, 0.2 mg/ml RNase A, 4% hydroxypropyl-b-cyclodextrin (cyclodextrin), 30% bead dilution buffer as discussed previously, 0.05% goat IgG, 0.05% sodium azide.

It will be understood by those skilled in the art that any detectable label such as, but not limited to, an enzyme, radioactive molecule, fluorescent molecule, or metal particle such as gold particle can be used. In certain aspects, the detectable label may be alkaline phosphatase. Methods of conjugating a label to an antibody are known. For example, an antibody can be reduced with dithiothreitol (DTT) to yield monovalent antibody fragments. The reduced antibody can then be directly conjugated to maleinated alkaline phosphatase by the methods of Ishikawa et al., J. Immunoassay 4:209-237 (1983) and Means et al., Chem. 1: 2-12 (1990), the contents of each of which are incorporated herein by reference in its entirety, and the resulting conjugate can be purified by HPLC. The conjugate may also be purified using any type of size-exclusion chromatography. One benefit of purification is that the conjugates of one protein to one antibody can be separated from those conjugates with other ratios of protein to antibody.

In another aspect, the double-stranded nucleic acid hybrids can be detected with a second anti-hybrid antibody that is not directly labeled. For example, the second antibody can be a mouse immunoglobulin that is detected by a labeled goat anti-mouse antibody.

The label present on the labeled solid support may be used to identify the particular genotype of the target nucleic acid. The label on the detection probe or detection antibody may convey information about the quantity of each target nucleic acid purified and may, in addition, convey additional information about the genotype of the target nucleic acids.

Methods for detecting various labels are known in the art. For example, colorimetry, radioactive, surface plasmon resonance, or chemiluminescence methods are described by e.g., Coutlee et al., J. Clin. Microbiol. 27:1002-1007 (1989), the contents of which are incorporated herein by reference in its entirety. For example, a bound alkaline phosphatase conjugate can be detected by chemiluminescence with a reagent such as a LUMI-PHOS 530 reagent (Lumigen, Detroit, Mich.) or DR2 (Applied Biosystems, Foster City, Calif.) using a detector such as an E/LUMINA luminometer (Source Scientific Systems, Inc., Garden Grove, Calif.), an OPTOCOMP I Luminometer (MGM Instruments, Hamden, Conn.), or the like, such as a Veritas Microplate Luminometer by Turner Biosystems. Multiple detection techniques can also be used in sequence or in parallel. For example, the conjugate may be detected by chemiluminescence and fluorescence. In another aspect, the conjugate can be detected by chemiluminescence.

Detectors using different detection techniques for the conjugate may be reversible or irreversibly attached, for example in a modular fashion, to a machine that is capable of performing the method for determining the presence of at least one target nucleic acid in a sample.

All probes used herein (including hybrid, capture, and detection probes) may be short synthetic RNA probes that specifically bind only to the at least one target nucleic acid. Examples are described in U.S. Patent Application Publication No. US 2009-0298187 A1, the contents of which are incorporated herein by reference in its entirety.

The present disclosure also provides for assay compositions, probes, and conditions wherein cross-reactivity between HR-HPV probe sets and LR-HPV types is dramatically reduced when compared to the standard FDA approved HPV assay and probe set. In one aspect, the HPV high-risk probe set is selected from the group consisting of HPV high-risk types 16, 18, 31, 33, 35, 39, 45, 51, 52, 56, 58, 59, 66, 68, and 82 or LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91. Using the present assay with these HR-HPV probes, cross-reactivity between LR-HPV types and HR-HPV probes is reduced. See, for example, U.S. Patent Application Publication No. US 2009-0298187 A1.

The present disclosure also provides methods and assays for detecting cancer, for example cervical cancer, by detecting the presence of a at least one target nucleic acid, such as HPV, in a sample.

It will be understood to those skilled in the art that the present invention can be carried out on a number of platforms including, but not limited to, tubes, dipsticks, microarrays, microplates, 384 well plates, other microtiter plates and microfluidic systems. It will be understood to those skilled in the art that the present, as relevant to developing countries, can utilize low technology methods such as dropper bottles, rubber bulbs, Pasteur pipettes, or squirt bottles for steps involving movement of liquid. These devices deliver relatively precise volumes within the approximate ranges that are needed for the assay. In an aspect, the methods of the disclosure do not include automatic pipettors or other battery powered or energy powered pipetting devices.

In an aspect, 10 copies or fewer of the at least one target nucleic acid can be purified and genotyped by the methods described herein in a volume of about 1 ml-20 ml of collection media in a time period of about 30 minutes to about 3 hours. In other aspects, 10 copies or fewer, 25 copies or fewer, or 50 copies or fewer of a at least one target nucleic acid can be detected by the methods described herein in a volume of about 1 ml of collection media in a time period of about 30 minutes to about 1 hour. In an aspect, the at least one target nucleic acid is at least one HPV nucleic acid selected from the group consisting of HPV high-risk types 16, 18, 31, 33, 35, 39, 45, 51, 52, 56, 58, 59, 66, 68, and 82 and LR-HPV types 6, 11, 40, 43, 53, 61, 67, 69, 70, 71, 72, 81, and 83.

V. Kit

Also provided is a kit for the detection of a at least one target nucleic acid in a sample, the kit comprising, consisting of, or consisting essentially of:
   i. a collection medium;
   ii. a denaturation reagent;
   iii. at least one polynucleotide hybrid probe;
   iv. a bead coated with a first anti-hybrid antibody;
   v. a polymerase;
   vi. a helicase;
   vii. a plurality of beads coated with immobilization probes, wherein each bead is coated with an immobilization probe specific for a single target nucleic acid and wherein each bead is detectably labeled;
   viii. a detection probe, wherein the detection probe may optionally be labeled, wherein the optional label is selected from the group consisting of: biotin, a His tag, protein G, a fluorophore; and
   ix. optionally comprising a detection reagent selected from the group consisting of: a compound that reacts with a detectable label on the detection probe, including streptavidin:HRP complexes; a second anti-hybrid antibodies bearing a second detectable label; and
   x. a wash buffer.

The collection medium, denaturation reagent, beads, first and second antibodies, polynucleotide probes, detection reagents, and wash buffers have been previously described.

In an aspect, a plurality of hybrid probes, a plurality of capture probes, and a plurality of detection probes are provided with the kit, wherein the plurality of each probe is specific for a set of target nucleic acids consisting of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

The kit may also include instructions for describing procedures associated with the disclosed methods and assays. The kit may also include a means for transcribing patient information. In an aspect, the means includes paper, a computer, or a device capable of transmitting patient information. The kit can include all the necessary components to complete the methods at the same location where the patient sample is taken.

In an aspect, the kit may include color coded reagents associated with the detection assay. The reagent vials are color coded for ease of use and can be included in a kit. The reagent bottles may also be identified by symbols, letters, or other known identifiers.

As the individual components of the kit come together in an easy to use platform, one advantage of the kit described herein is that it provides for immediate testing of samples. This allows for rapid determination of patient results.

In an aspect, methods of the disclosure can include the collection, processing, and performing the purifying step on patient samples in the field. In one aspect, after the samples are collected, some of the method steps are conducted at the same location where the patient samples are collected. The location may be a village, clinic, laboratory, or communal area where individuals receive medical checkups and evaluations. The location may be permanent or temporary. In an aspect, the nucleic acid is detected at a location, such as a laboratory or clinic, which is different from where the samples are taken. In an aspect, the kit is designed for use in a developing country or geographical areas where access to medical care is not readily available.

This method is further compatible with STM and PC samples.

The following examples are illustrative only and are not intended to limit the disclosure in any way.

EXAMPLES

Among the many possible target nucleic acid sequences which may be purified, detected, and/or characterized by the above-described method, HPV nucleic acid sequences provide an excellent illustrative example.

Members of the HPV family are associated with a number of different disorders and/or infections, including common warts, genital warts, and cancers of the head, neck, throat, penis, anus, cervix, vulva, and vagina. Over 100 types of HPV viruses have been described, 56 of which have been associated with mucosal and/or cutaneous lesions to date. These 56 mucosal and/or cutaneous lesion-associated HPV types are typically segregated into "high-risk" and "low-risk" groups. HR-HPV are those that are associated with malignant lesions and may include, for example, HPV types 16, 18, 26, 31, 33, 35, 39, 45, 51, 52, 56, 58, 59, 66, 68, and 82. LR-HPV are associated benign lesions and may include, for example, HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

However, prior to the development of the above-described method, there were no tests available which were able to genotype all known HR- and LR-HPV types. Other molecular diagnostic methods of detecting HPV are limited in their multiplexing capability, decreasing the usefulness of those methods for genotyping. Chemiluminescent methods, such as Hybrid Capture 2, are sensitive and reliable, but have a homogeneous output, necessitating separate wells for each genotype to be detected. PCR and PCR-like tests rely on the use of consensus primer (e.g. GP5+/6+, MY09/MY11, etc.). These tests inherently have different efficiencies for different targets, resulting in amplification bias, making detection of multiple HPV infection difficult and unreliable. Additionally, cross-talk among fluorophores, competition during amplication, and increasing problems with primer-dimers negatively affect and limit the number of targets that can be amplified and detected simultaneuously. Moreover, another limitation is the relatively small size of the targeted amplicon region which in turn results in assays that are sensitive to deletions, mutations, or insertions. For example, if this targeted region is deleted during viral integration into the host genome (as has been shown with the L1 region), the infection will be missed. Additionally, false negatives may occur when there are mutations or deletions in the region targeted by the detection probe.

In the following examples, the above described methods were used to purify, detect, and characterize 26 HPV types, including all currently known HR-HPVs.

Example 1

Assay Design

The following examples all utilize the same general assay design. First, HPV nucleic acids are isolated from the sample through the use of hybrid capture. Then, the isolated HPV nucleic acids are amplified using whole genome amplification. The amplified HPV nucleic acids are then segregated according to HPV serotype using capture probes specific for each individual HPV serotype immobilized to a uniquely labeled bead. A biotinylated detection probe is then hybridized to the segregated HPV nucleic acids and a streptavidin/phycoerythrin (SA-PE) conjugate is bound to the detection probe to generate a signal. Both the unique label of the bead and the signal generated by the SA-PE are measured using flow cytometry. The bead label is used to indicate the genotype bound to the bead, while the SA-PE signal is used to indicate the presence or absence of bound HPV nucleic acid to each bead.

A. Purification Probe Preparation.

A purification probe set was designed so as to be able to isolate nucleic acids of all of the HPV serotypes being. Although in principle the probes could be any length, short 25-mer probes were selected to provide flexibility of probe design and ease of manufacture.

The purification probe set was prepared using two basic criteria. First, the probes were selected such that they were dispersed throughout the target genome so as to capture all regions of the genome. Second, multiple probes were clustered around specific regions to ensure that each region being tested was purified.

To minimize the total number of required probes, the probes were designed so that a single probe could be used as a consensus probe for two or more HPV types. To discover the consensus sequences, alignments of the HPV sequences being tested were performed in a family-wise fashion. For example, all members of the A9 (HPV 16) family, comprising HPVs 16, 31, 33, 35, 52, 58, & 67, or the A7 (HPV18) family, comprising HPV18, HPV39, HPV45, HPV59, HPV68, HPV70, and HPV85, were aligned by ClustalW and the consensus sequence was analyzed for the presence of a contiguous 25-mer sequence. Such a sequence would then be chosen as a probe candidate. Based on the phylogenetic tree constructed during the analysis, the two most closely related sequences were then aligned with one another and the search for consensus sequences was repeated. Thus, the probes enumerated in Table 1 (below) were designed.

TABLE 1

PURIFICATION PROBE SEQUENCES FOR 27 TYPES OF HPV

| SEQ ID NO. | Name | Sequence |
|---|---|---|
| 1 | HPV16-E6E7-1 | AACCGAAACCGGUUAGUAUAAAAGC |
| 2 | HPV16-E6E7-2 | UUAGAAUGUGUGUACUGCAAGCAAC |
| 3 | HPV16-E6E7-3 | GGUAUAUGACUUUGCUUUUCGGGAU |
| 4 | HPV16-E6E7-4 | AGUAUAUAGAGAUGGGAAUCCAUAU |
| 5 | HPV16-E6E7-5 | ACAACAAACCGUUGUGUGAUUUGUU |
| 6 | HPV16-E6E7-6 | UUAGGUGUAUUAACUGUCAAAAGCC |
| 7 | HPV16-E6E7-7 | GAUUCCAUAAUAUAAGGGGUCGGUG |
| 8 | HPV16-L1-1 | AUGUUGCACGCACAAACAUAUAUUA |
| 9 | HPV16-L1-2 | GUUCCUAAAGUAUCAGGAUUACAAU |
| 10 | HPV16-L1-3 | UCCCUAUUUUCCUAUUAAAAAACCU |
| 11 | HPV16-L1-4 | GUUUGGGCCUGUGUAGGUGUUGAGG |
| 12 | HPV16-L1-5 | GUCAGCCAUUAGGUGUGGGCAUUAG |
| 13 | HPV16-L1-6 | UGUGUUUAAUUGGUUGCAAACCACC |
| 14 | HPV16-L1-7 | GGUGAUUGUCCACCAUUAGAGUUAA |
| 15 | HPV16-L1-8 | CAGUUAUUCAGGAUGGUGAUAUGGU |
| 16 | HPV16-A9-1 | GAAAUCCUUUUUCUCAAGGACGUGG |
| 17 | HPV16-A9-2 | CAAUGUGUAGACAUUAUAAACGAGC |
| 18 | HPV16-A9-3 | UUAGACAUUUAUUUAAUAGGGCUGG |
| 19 | HPV16-A9-5 | CAUAUGAUAAUCCUGCAUAUGAAGG |
| 20 | HPV16-A9-6 | AAUAUGAUUUACAGUUUAUUUUUCA |
| 21 | HPV16-A9-7 | AUCCUUUAUUAAAUAAAUUGGAUGA |
| 22 | HPV16/35-A9-8 | CUAUUAGUACACAUAAUUAUGAAGA |
| 23 | HPV31/35-A9-1 | GGUACAAUGGGCAUAUGACAAUGAU |
| 24 | HPV31/35-A9-2 | GACAAACAGUAUUACAGCAUAGUUU |
| 25 | HPV31/35-A9-3 | GAUGGUAUAGAUAUAGUGUGUAUGG |
| 26 | HPV31/35-A9-4 | GAUUAAAUUUGCACGAGGAAAGAGG |
| 27 | HPV31-E6E7-1 | ACGAUGAACUAAGAUUGAAUUGUGU |
| 28 | HPV31-E6E7-2 | ACAGAGGUAUUAGAUUUUGCAUUUA |
| 29 | HPV31-E6E7-3 | UUAAUUAGGUGUAUAACGUGUCAAA |
| 30 | HPV31-E6E7-4 | AGAAGAAAACAAAGACAUUUGGAU |
| 31 | HPV31-E6E7-5 | AGGAAGGUGGACAGGACGUUGCAUA |
| 32 | HPV31-L1-1 | GAACCAACAUAUAUUAUCACGCAGG |
| 33 | HPV31-L1-2 | AUCCAUAUUAUUCCAUACCUAAAUC |
| 34 | HPV31-L1-3 | UCAGGAUUACAAUAUAGGGUAUUUA |
| 35 | HPV31-L1-4 | GACACUGAAAACUCUAAUAGAUAUG |
| 36 | HPV31-L1-5 | AAUGUAUAUCAAUGGAUUAUAAACA |
| 37 | HPV31-L1-6 | CUAUUGGAGAGCAUUGGGGUAAAGG |
| 38 | HPV31-L1-7 | GGUGAUUGUCCUCCAUUAGAAUUAA |
| 39 | HPV31-E6E7-6 | UAGUAUAUAGGGACGACACACCACA |
| 40 | HPV31-E6E7-7 | CUGAAACCCAAGUGUAAACAUGCGU |
| 41 | HPV35-E6E7-1 | GCUAUGAUUUGUGUAUAGUAUAUAG |
| 42 | HPV35-E6E7-2 | UCCAGUUGAAAAGCAAAGACAUUUA |
| 43 | HPV35-E6E7-3 | UUGUAAAUGUGAGGCGACACUACGU |
| 44 | HPV35-E6E7-4 | AAGAUUUAUUAAUGGGCACAUUUGG |
| 45 | HPV35-L1-1 | GCACAAACAUCUACUAUCAUGCAGG |
| 46 | HPV35-L1-2 | CAAUACAGAGUAUUUAGAGUAAAAU |
| 47 | HPV35-L1-3 | CUAAUAAGUUUGGAUUUCCAGACAC |
| 48 | HPV35-L1-4 | UGGUUUGGGCCUGUACAGGAGUUGA |
| 49 | HPV35-L1-5 | GUACAGAUAACAGGGAAUGCAUUUC |
| 50 | HPV67-E6E7-1 | UAACCGAAAACGGUUUGACCGAAAA |
| 51 | HPV67-E6E7-2 | CGAAAAACCACGCAACCUGCACGAA |
| 52 | HPV67-E6E7-3 | CUUUGGAAACCACGGUGCAUGAAAU |
| 53 | HPV67-E6E7-4 | CUUUGGACAGAAACGAGGUAUAUGA |
| 54 | HPV67-E6E7-5 | UCUGUGAGUGCACUUUGCGUUUGUG |
| 55 | HPV67-E6E7-6 | AAUCCAGCAGAUGCUUAUGAACACA |
| 56 | HPV67-L1-1 | UAUUGAAAUAGGGCGAGGACAGCCU |
| 57 | HPV67-L1-2 | CUGAUAAUAGGGAAUGCUUGUCUAU |
| 58 | HPV67-L1-3 | UUUGGAACUUAUGAAUACUGUUAUU |
| 59 | HPV67-L1-4 | GAGCAGGUAAAUUAGGGGAGGAUGU |
| 60 | HPV67-L1-5 | GCAAACACUUCUGCACUGCAAACCU |
| 61 | HPV67-L1-6 | GCUAAACCUAAACUAAAACGUUCUU |
| 62 | HPV67-L1-7 | CAAAACGUAAAAAGGUUAAAAGGUA |
| 63 | HPV52-E6E7-1 | GUGUAGCUAACGCACGGCCAUGUUU |
| 64 | HPV52-E6E7-2 | UGCACGAAUUGUGUGAGGUGCUGGA |
| 65 | HPV52-E6E7-3 | UACAACGAAGAGAGGUAUACAAGUU |
| 66 | HPV52-E6E7-4 | ACGAAUAGUAUAUAGAGACAAUAAU |
| 67 | HPV52-E6E7-5 | GGCAUUAUCAAUAUUCACUGUAUGG |
| 68 | HPV52-E6E7-6 | CUAUGAGCAAUUAGGGUGACAGCUCA |
| 69 | HPV52-E6E7-7 | GCCAGAUGGACAAGCAGAACAAGCC |
| 70 | HPV52-L1-1 | UAACAGUAGGACAUCCCUAUUUUUC |
| 71 | HPV52-L1-2 | AAAAAAGUUUUAGUUCCCAAGGUGU |

TABLE 1-continued

PURIFICATION PROBE SEQUENCES FOR 27 TYPES OF HPV

| SEQ ID NO. | Name | Sequence |
|---|---|---|
| 72 | HPV52-L1-3 | UUUGAUGAUACUGAAACCAGUAACA |
| 73 | HPV52-L1-4 | AGGGAAUGUUUAUCUAUGGAUUAUA |
| 74 | HPV52-L1-5 | UGCAAACCUCCUAUAGGUGAACAUU |
| 75 | HPV52-L1-6 | AGGAUGGGGACAUGGUAGAUACAGG |
| 76 | HPV33/58-A9-1 | UAGAAGACAGCGGAUAUGGCAAUAC |
| 77 | HPV33/58-A9-2 | GCUGUACAGAUUGGUGUAUAACAGG |
| 78 | HPV33/58-A9-3 | AUUGGUUUAGAACAGCAAUGUCAAA |
| 79 | HPV33/58-A9-4 | UCAUAUUUUGGAAUGAGUUUAAUAC |
| 80 | HPV33/58-A9-5 | UUUUGGUUGCAGCCAUUAUCAGAUG |
| 81 | HPV33/58-A9-6 | AAUAGAGGAAGAGGACAAGGAAAAC |
| 82 | HPV33/58-A9-7 | AUGGAGGAAAUAUCAGCACGUUUAA |
| 83 | HPV33/58-A9-8 | CAUCACAAAUUGAACAUUGGAAACU |
| 84 | HPV33/58-A9-9 | GGACAUUGCAACAAACAAGCUUAGA |
| 85 | HPV33/58-A9-10 | AUUUUAAAUAUUUUAAAGAGGAUGC |
| 86 | HPV33/58-A9-11 | AAUAUCCACUACUGAAACUGCUGAC |
| 87 | HPV33/58-A9-12 | CAAAUAGUUUAAAAUGUUUAAGAUA |
| 88 | HPV33/58-A9-13 | UGAUGUGUAUUAAUUUUCAUGCACA |
| 89 | HPV33/58-A9-14 | UCUACAAGGCGCAAGCGUGCAUCUG |
| 90 | HPV33/58-A9-15 | GAAAACAUACCAAUGGAUACCUUUG |
| 91 | HPV33/58-A9-16 | GCCCUGUGGCACGCCUUGGUUUAUA |
| 92 | HPV33/58-A9-17 | CAGAUGUCCGUGUGGCGGCCUAGUG |
| 93 | HPV33/58-A9-18 | ACAUUGCAGGCUAAUAAAAGUGAUG |
| 94 | HPV33/58-A9-19 | CAGUACAUGCAAAUAUCCAGAUUAU |
| 95 | HPV52/67-A9-1 | GAGAAAUGGUGCAAUGGGCAUAUGA |
| 96 | HPV52/67-A9-2 | UUUUAAAAGGUAUACCUAAAAAAA |
| 97 | HPV52/67-A9-3 | UAACAGUGCAAUACGAUAAUGAUAA |
| 98 | HPV52/67-A9-4 | CAGAUGUCCGUGUGGCGGCCUAGUG |
| 99 | HPV52/67-A9-5 | AGGCCACUGUGUACCUGCCUCCUGU |
| 100 | HPV52/67-A9-6 | UUAGAGGACUGGCAAUUUGGCUUA |
| 101 | HPV52/67-A9-7 | CAUGUUUUAAACUGCUUUUAGGCAC |
| 102 | HPV18/45-A7-1 | AUGCUGCAUGCCAUAAAUGUAUAGA |
| 103 | HPV18/45-A7-2 | UUAAAACGAAAGUUUGCAGGAGGCA |
| 104 | HPV18/45-A7-3 | UCAGAUAGUGGCUAUGGCUGUUCUG |
| 105 | HPV18/45-A7-4 | UUAGAAAUUUUAAAGUGAUAAAAC |
| 106 | HPV18/45-A7-5 | UGUAAAUGGGGAGUAUUAAUAUUAG |
| 107 | HPV18/45-A7-6 | CACCAAAAUUGCGAAGUAGUGUUGC |
| 108 | HPV18/45-A7-7 | AUGCAUUCCAUUUGAUAAAAAUGG |
| 109 | HPV18/45-A7-8 | GAAAGGACAUGGUCCAGAUUAGAUU |
| 110 | HPV18/45-A7-9 | UUGAUUGUAAUGACUCUAUGUGCAG |
| 111 | HPV18/45-A7-10 | UACCAGUGACGACACGGUAUCCGCU |
| 112 | HPV18/45-A7-11 | GUGGUAACACUACGCCUAUAAUACA |
| 113 | HPV18/45-A7-12 | GUAAUAAAACUGCUUUUAGGCACAU |
| 114 | HPV18-E6E7-1 | AGGAUCCAACACGGCGACCCUACAA |
| 115 | HPV18-E6E7-2 | CUUCACUGCAAGCAUAGAAAUAAC |
| 116 | HPV18-E6E7-3 | AGGUAUUUGAAUUUGCAUUUAAAGA |
| 117 | HPV18-E6E7-4 | GAGGCCAGUGCCAUUCGUGCUGCAA |
| 118 | HPV18-L1-1 | UGGUAAUCCAUAUUUUAGGGUUCCU |
| 119 | HPV18-L1-2 | UUCCUAAGGUUUCUGCAUACCAAUA |
| 120 | HPV18-L1-3 | AUCCUGAAACACAACGUUUAGUGUG |
| 121 | HPV18-L1-4 | AGGACGUUAGGGACAAUGUGUCUGU |
| 122 | HPV45-E6E7-1 | UGACGAUCCAAAGCAACGACCCUAC |
| 123 | HPV45-E6E7-2 | UAGACACCUUAAGGACAAACGAAGA |
| 124 | HPV45-E6E7-3 | GUGUGACGGCAGAAUUGAGCUUACA |
| 125 | HPV45-E6E7-4 | UACAGCAGCUGUUUUUGAGCACCUU |
| 126 | HPV45-L1-1 | UGUAGGCAAUCCAUAUUUUAGGGUU |
| 127 | HPV45-L1-2 | UUCCUAAGGUAUCCGCAUAUCAGUA |
| 128 | HPV45-L1-3 | AUAAUCCUGAAACACAACGUUUGGU |
| 129 | HPV45-L1-4 | AGGAUGUUAGGGAUAAUGUGUCAGU |
| 130 | HPV39/68-A7-1 | CCAUACAAAUUGCCAGACCUGUGCA |
| 131 | HPV39/68-A7-2 | UCGGUGUAUGCAACUACAUUAGAAA |
| 132 | HPV39/68-A7-3 | UACAAUGAAAUACAGCCGGUUGACC |
| 133 | HPV39/68-A7-4 | UUGUAUGUCACGAGCAAUUAGGAGA |
| 134 | HPV39/68-A7-5 | GAUGAAAUAGAUGAACCCGACCAUG |
| 135 | HPV39/68-A7-6 | AGCGUGAGACAGCACAGGUACUUUU |
| 136 | HPV39/68-A7-7 | AGUGCUAUAGAUGUGAAAACCAGG |
| 137 | HPV39/68-A7-8 | GUAAAAGAUUGUGCAACAAUGUGUA |
| 138 | HPV39/68-A7-9 | AAAUUCCUAAUGCAUUUCCAUUUG |
| 139 | HPV39/68-A7-10 | GAAAAGACUGGUGCAGAUUAGACU |
| 140 | HPV39/68-A7-11 | GACGAGGAUGAAGGAGACAAUGAUG |
| 141 | HPV39/68-A7-12 | AAGCAUAUCAAGCUAUUGAACUGCA |
| 142 | HPV39/68-A7-13 | CAUUGUCCUGACUCUAUGUGCAGUA |
| 143 | HPV39/68-A7-14 | ACACCAGUACCAACAUUUACAGGCA |
| 144 | HPV39/68-A7-15 | CAGGUUCGUGUUAGUAAUUUUGAUU |

TABLE 1-continued

PURIFICATION PROBE SEQUENCES FOR 27 TYPES OF HPV

| SEQ ID NO. | Name | Sequence |
|---|---|---|
| 145 | HPV39/68-A7-16 | CACCCUUCAUCAUUUGUAACAUUUG |
| 146 | HPV39/68-A7-17 | AUAAUCCUGCUUUUGAGCCUGUUGA |
| 147 | HPV39/68-A7-18 | GAUCCGGAUUUUCUGGACAUUGUUC |
| 148 | HPV39/68-A7-19 | UGCAAAUGUCUGCAGAUGUGUAUGG |
| 149 | HPV39/68-A7-20 | CUAAACACAAACGUAAACGUGUGUC |
| 150 | HPV59/70-A7-1 | GCAACAGAUACAGGUUCAGACUUGG |
| 151 | HPV59/70-A7-2 | AUUUGUGUACAGGCAGAGCGCGAGA |
| 152 | HPV59/70-A7-3 | UUAGUCAUCAUCCUGUCCAGGUGCA |
| 153 | HPV70-E6E7-1 | UAUAAAACCAUGCAAAAGUUGCUUG |
| 154 | HPV70-E6E7-2 | CCUGCAGAACGGCCAUACAAAUUGC |
| 155 | HPV70-E6E7-3 | UGCAUGCCAAAAAUGUAUUAAAUUU |
| 156 | HPV70-E6E7-4 | GACGUAUACGAAGAGAAACACAAGU |
| 157 | HPV70-E6E7-5 | ACAUUGCAAGAGAUUGUUUUAGAUU |
| 158 | HPV70-E6E7-6 | CUACACUGCACUUAGUAGUAGAAGC |
| 159 | HPV70-E6E7-7 | GCAGCUGUUUAUGGAGACACUGUCA |
| 160 | HPV70-L1-1 | GGGUAUCCCUACCUGAUCCUAAUAA |
| 161 | HPV70-L1-2 | UAUAAUCCUGACACACAACGCCUGG |
| 162 | HPV70-L1-3 | CUUCAGAGUUAUAUAUUAAAGGCAC |
| 163 | HPV70-L1-4 | AUGUAUAUUCCCCUUCCCCAAGUGG |
| 164 | HPV70-L1-5 | CACGUAGUACUAAUUUUACAUUGUC |
| 165 | HPV70-L1-6 | CUGUAUAUAGCCCUACAAAGUUUAA |
| 166 | HPV70-L1-7 | UCUAAACACAAACGGAAACGUGUGU |
| 167 | HPV59-E6E7-1 | UUAUAGUGUAUAGAGACUGUACACC |
| 168 | HPV59-E6E7-2 | UUUUAUGCAAGAGUAAGAGAAUUAA |
| 169 | HPV59-E6E7-3 | UAUUAUAGAGAUUCCGUGUAUGGAG |
| 170 | HPV59-E6E7-4 | UGCCUAAAACCUCUAUGUCCAACAG |
| 171 | HPV59-E6E7-5 | ACCACAAAAUUAUGAGGAAGUUGAC |
| 172 | HPV59-E6E7-6 | CUCCGAGAAUGAAAAAGAUGAACCA |
| 173 | HPV59-L1-1 | UGGACAUCCAUAUUUUAAAGUACCU |
| 174 | HPV59-L1-2 | UUCCUAAGGUGUCUGCAUAUCAAUA |
| 175 | HPV59-L1-3 | UGGAUGACACUGAAAACUCUCAUGU |
| 176 | HPV59-L1-4 | GAUAAUGUAUCUGUGGAUUAUAAAC |
| 177 | HPV59-L1-5 | UGAAUCACUAUAUAUUAAAGGUACU |
| 178 | HPV59-L1-6 | UAUUCCCCUUCCCCAAGUGGGUCUG |
| 179 | HPV59-L1-7 | GUGCAGCGCCUGCCCCUACCUCUAC |
| 180 | HPV59-L1-8 | UCUUCCAGAAAAUAGUGUUGUUUGU |
| 181 | HPV59-na-1 | UGUAUUGUUUGCCUGUUUGUAUGUU |
| 182 | HPV59-na-2 | CCGUUUUGUUCAAUCUGCUGCUGUA |
| 183 | HPV59-na-3 | AAGACAGCAACGACAAGCGCGUAGU |
| 184 | HPV54-E6E7-1 | AAGCGGAUGUAGAAAACAGUUAUUU |
| 185 | HPV54-E6E7-2 | ACGGACCAGCCGCGUACUCUAGCUG |
| 186 | HPV54-E6E7-3 | UAUGCAUAGUUUGCAACUUCCUUGU |
| 187 | HPV54-E6E7-4 | GCAGAGAUUUAUGCAUUUCAAUAUA |
| 188 | HPV54-E6E7-5 | GUGGAGACACGGCUUUCCACAUGCU |
| 189 | HPV54-E6E7-6 | AAAUAAUUAUAGAAGGCAUCGCGA |
| 190 | HPV54-na-1 | UGCAUGGAAAUGUGGCUACAAUUGA |
| 191 | HPV54-E6E7-7 | GUGGAGGUGUGUGUUGUAAGACAGU |
| 192 | HPV54-E6E7-8 | CAUAAGGGUACUGCAGGAACUGCUU |
| 193 | HPV54-na-2 | AAACGAAAGUAUAUAGGCAGUCCGU |
| 194 | HPV54-na-3 | GAGUUUUAUGGACCUAGCACGGUCC |
| 195 | HPV54-L1-1 | UUAUUGGCUGUUGGACAUCCAUAUU |
| 196 | HPV54-L1-2 | UAUUCCUAAAGUAUCAGGAUAUCAA |
| 197 | HPV54-L1-3 | CUAUAGGUGAACACUGGGCUAAAGG |
| 198 | HPV54-L1-4 | GCUGGUGACUGUCCUCCUUUGGAAU |
| 199 | HPV54-L1-5 | GGAUUUUAAAACCCUACAAACCUCA |
| 200 | HPV54-L1-6 | AUUUGUAAAUAUCCUGAUUACCUUA |
| 201 | HPV54-L1-7 | GUAGUACUAACCUAACAUUGUGUGC |
| 202 | HPV54-L1-8 | UUCUGACUUUAGGGAGUAUAUUAGA |
| 203 | HPV54-na-4 | UAUGCUGCAACUCCUAGUGGCUCUA |
| 204 | HPV70/85-A7-1 | UAGAUGACAGUGUAUUUGACCUGUC |
| 205 | HPV70/85-A7-2 | UAUGGGGACAGUAUGUUUUUUUGUU |
| 206 | HPV70/85-A7-3 | GAGGAAUAUGAUUUACAAUUUAUAU |
| 207 | HPV85-E6E7-1 | CUACCCGACCCUACAAACUACCAGA |
| 208 | HPV85-E6E7-2 | AAGAUAUAGAAAUAAGCUGUGUAUA |
| 209 | HPV85-E6E7-3 | AUAGCGACUCUGUGUAUGGGGAAAC |
| 210 | HPV85-E6E7-4 | AUGAUAUUAUAAUAAGGUGUUUACG |
| 211 | HPV85-E6E7-5 | AUAUAAUGAAGUGCAAGAGGUUGAC |
| 212 | HPV85-E6E7-6 | AGGAAGAAAUAGAUGAACCAGAUAA |
| 213 | HPV85-L1-1 | AUGACACAGAAAAUUCCCAUGUUGC |
| 214 | HPV85-L1-2 | GAUAAUGUGUCAGUGGAUUAUAAAC |
| 215 | HPV85-L1-3 | GGGAACAUGGGCUAAGGGUACUGC |
| 216 | HPV85-L1-4 | UGUCCUCCAUUAGAACUAGUAAAUA |
| 217 | HPV85-L1-5 | GAAACUUAUAUAUAAAAGGUACUAA |

TABLE 1-continued

PURIFICATION PROBE SEQUENCES FOR 27 TYPES OF HPV

| SEQ ID NO. | Name | Sequence |
|---|---|---|
| 218 | HPV85-L1-6 | UAUUCUCCAUCACCUAGUGGGUCUA |
| 219 | HPV85-L1-7 | CAUCUGCCAUUACAUGUCAGAAGGA |
| 220 | HPV85-L1-8 | UAUGAAAAUUAAAGUUUUGGAAUG |
| 221 | HPV85-na-1 | GUUUUUACUUGCUUUAAUUACACUA |
| 222 | HPV85-na-2 | ACAAGAAAUAUCGUUAAAUAGCUAU |
| 223 | HPV85-na-3 | CAAGGGAGCAUGGUCUUAAAACAAU |
| 224 | HPV26/69-E6E7-1 | GCAGGUACAGUGUGUAUAUUGCAAG |
| 225 | HPV26/69-E6E7-2 | GUGCCGCAACCCGAAAUUGACCUAC |
| 226 | HPV26/69-E6E7-3 | GGACUAUGAACAAUUUGACAGCUCA |
| 227 | HPV26/69-E6E7-4 | GUAAUAGUAUAGUGCAGCUAGCUGU |
| 228 | HPV26/69-E6E7-5 | GUACAGGGUGGUUUUCAGUAGAAGC |
| 229 | HPV26/69-E6E7-6 | AGAACAGCCCGUUGCAAGACAUAAC |
| 230 | HPV26/69-E6E7-7 | AUACUGAAGUGGAAACUCUUACGCC |
| 231 | HPV26/69-E6E7-8 | AGUGUGUGUAGUCAGGGGGGGUCAA |
| 232 | HPV26/69-na-1 | UGUGGCAGGCUCUGUAGCAGAAAGU |
| 233 | HPV26/69-na-2 | AUUUAUCAAAAAUGGUGCAAUGGGC |
| 234 | HPV26/69-na-3 | GGCAAAAUAUGUAAAAGACUGUGCA |
| 235 | HPV26/69-na-4 | GACAGCAAUGGGAAUCCUGUAUAUG |
| 236 | HPV26/69-na-5 | UGGUCCAGAUUAGAUUUGGAGGAGG |
| 237 | HPV26/69-na-6 | AUCUACCUGGCAUUGGACCAGUAAU |
| 238 | HPV26/69-na-7 | GUUUGUGCUUUGCGUGUGUGUGUGU |
| 239 | HPV26/69-L1-1 | CCUUUGAUAAUCCUGCAUAUGAACC |
| 240 | HPV26/69-L1-2 | GUACUAGUGACAGCAAGGUAUAUCU |
| 241 | HPV26/69-L1-3 | GAAACAGCAUGUUUUUUUUCUUCG |
| 242 | HPV26/69-L1-4 | ACAACACAUCCUGCCUCCUACGCUU |
| 243 | HPV26/69-L1-5 | AAUAAAACUGCUGUUAGGCACAUAU |
| 244 | HPV51/82-E6E7-1 | CACUUGGGCCUGAAGAAAAGCAAAA |
| 245 | HPV51/82-E6E7-2 | GUGUAAUAAAGCCAUGCGUGGUAAU |
| 246 | HPV51/82-E6E7-3 | AAAUUGACUUGCAAUGCUACGAGCA |
| 247 | HPV51/82-E6E7-4 | UGGACAGGCUACGUGUUACAGAAUU |
| 248 | HPV51/82-E6E7-5 | AGCAGCCCAUUAGGAGACAUUACAA |
| 249 | HPV51/82-E6E7-6 | GAUUACUGGACAGUUAUCCGGACAG |
| 250 | HPV51/82-E6E7-7 | UGUGGAAGCAACGUUGCAGGUAGAU |
| 251 | HPV51/82-na-1 | ACAGCCACUAGAGGAUGCUAAAAUA |
| 252 | HPV51/82-na-2 | GUCCAGAUUAGAUUUGGAGGAGGAA |
| 253 | HPV51/82-na-3 | UGCCAGGAGAAAAUACUAGACUGUU |
| 254 | HPV51/82-na-4 | UCAACCUGGCAUUGGACCAGUAAUA |
| 255 | HPV51/82-na-5 | ACAAGCCAAUAUGUGCUGCUAAUUG |
| 256 | HPV51/82-na-6 | UGUGUGUGUGUCUUGUGUUGUGUUG |
| 257 | HPV51/82-na-7 | ACAUGCAAAGCUGCUGGUACAUGUC |
| 258 | HPV51/82-na-8 | UGGAGUGGGUUGGGUAUAUUUUUGG |
| 259 | HPV51/82-L1-1 | GAACUUGAAAUGCAGCCUUUACUUU |
| 260 | HPV51/82-L1-2 | UGUCUUCAUCUUUAUGCAAAUGUUAC |
| 261 | HPV51/82-L1-3 | UGGGGAUUACUAUUUGUGGCCCUAU |
| 262 | HPV51/82-L1-4 | AAACGCCGUAAACGUAUACCCUAUU |
| 263 | HPV51/82-L1-5 | UCUUCCUCUUCCUCUUCAGCCAAAC |
| 264 | HPV30/53-E6E7-1 | CCGAAAACGGUACAUAUAAAAGCAC |
| 265 | HPV30/53-E6E7-2 | GACACCAGAGGAAAAACAGUUACAC |
| 266 | HPV30/53-E6E7-3 | AUGAGCAAUUGAACAGCUCAGAGGA |
| 267 | HPV30/53-E6E7-4 | CAAUGGCGUCACCUGAAGGUACAGA |
| 268 | HPV30/53-E6E7-5 | UAAAACGAAAGUAUUUAGGCAGUCC |
| 269 | HPV30/53-na-1 | CAGCGGGUAUGGCAAUACUUUGGAA |
| 270 | HPV30/53-na-2 | ACACAGUCACUUUUGGUUACAACCG |
| 271 | HPV30/53-na-3 | GAAAGGACAUGGUCCAGAUUAGAUU |
| 272 | HPV30/53-na-4 | CGUGCCAGGAGAAAAUUCUAGACUG |
| 273 | HPV30/53-na-5 | UACAAGUGUGUAAAGCAAAGGCAUG |
| 274 | HPV30/53-na-6 | UAAAGGCACAUGGGAAGUGCAUAUG |
| 275 | HPV30/53-na-7 | GUAUUUAUUGUCCCGACUCUGUGUC |
| 276 | HPV30/53-L1-1 | GAAAUACCUAUGCAAACAUUUGCUG |
| 277 | HPV30/53-L1-2 | CACAGACCUGCCUUUACAACACGUA |
| 278 | HPV30/53-L1-3 | GGUGGUGUGCGUUUUAGUAGGCUUG |
| 279 | HPV30/53-L1-4 | AGAAGUGGCAAACAAAUAGGUGCUC |
| 280 | HPV30/53-L1-5 | GAUGGCCUAUAUGAUAUUUAUGCAA |
| 281 | HPV30/53-L1-6 | UUCCCUAUUUUCUUGCAGAUGGCGG |
| 282 | HPV30/53-L1-7 | GCUUAGAGGACAAAUACAGAUAUGU |
| 283 | HPV30/53-L1-8 | UGUAUGACUGUAUGUAUGUGUAAUG |
| 284 | HPV56/66-E6E7-1 | CCGAAAACGGUACAUAUAAAAGGCA |
| 285 | HPV56/66-E6E7-2 | CUCAGAGGAUGAGGAUGAGGAUGAA |
| 286 | HPV56/66-E6E7-3 | GCGGCCACAGCAAGCUAGACAAGCU |
| 287 | HPV56/66-E6E7-4 | GCGUUAACAGUAACGUGCCCACUCU |
| 288 | HPV56/66-E6E7-5 | GCAAGUACAAACAGCACAUGCAGAU |
| 289 | HPV56/66-na-1 | ACAGACGUUGCAAAAACUAAAACGA |
| 290 | HPV56/66-na-2 | AUGAAUAUGUGCCAGUGGAUAAAGC |

TABLE 1-continued

PURIFICATION PROBE SEQUENCES FOR 27 TYPES OF HPV

| SEQ ID NO. | Name | Sequence |
|---|---|---|
| 291 | HPV56/66-na-3 | UGAAGGGGUGAUUGGAAACCCAUU |
| 292 | HPV56/66-na-4 | GGAUAACGACGAGGACAAAGAAAAC |
| 293 | HPV56/66-na-5 | UGUAAAGCAAAAGCAUGUAGUGCAA |
| 294 | HPV56/66-na-6 | GUCCUGACUCUGUGUCUAGUACCUG |
| 295 | HPV56/66-na-7 | GUAUCCCACAGACCAGGAAAACGAC |
| 296 | HPV56/66-na-8 | GUUUGCGCUUUGCUUUUGUGUUUGU |
| 297 | HPV56/66-na-9 | AUAGGCCUGCAUUUACUACACGUAG |
| 298 | HPV56/66-L1-1 | GAUAUAAGUCCUAUUGCACAGGCUG |
| 299 | HPV56/66-L1-2 | AGGCGCCGUAAACGUAUUCCCUAUU |
| 300 | HPV56/66-L1-3 | CUACCUCCAACACCUGUUUCAAAGG |
| 301 | HPV56/66-L1-4 | UUCUAUGUGGUUUUACUUACGCAGG |
| 302 | HPV56/66-L1-5 | AUAAACCUUAUUGGUUGCAACGUGC |
| 303 | HPV56/66-L1-6 | ACGCGUGGUUGCAUAAACUAAGGUG |
| 304 | HPV34/73-E6E7-1 | UAAUAAGGUGCGGAAAAUGCCAAAA |
| 305 | HPV34/73-E6E7-2 | GACAACUCAGAGGAUGAGGAUGAAA |
| 306 | HPV34/73-E6E7-3 | AGAAGAUGGCUGAUUCAGGUAAUUG |
| 307 | HPV34/73-E6E7-4 | CGGGAUGGUUUAAUGUAGAAGCCAU |
| 308 | HPV34/73-E6E7-5 | UGGGGGAUUUUAUUGAUAAUGCACA |
| 309 | HPV34/73-E6E7-6 | AAUGCAGACAAUGAGGCUAUACGUG |
| 310 | HPV34/73-E6E7-7 | GAUAUGGCAAUACUGAAGUGGAAAC |
| 311 | HPV34/73-E6E7-8 | UAGUGGGUCCAGUAGCAUUUCAAAU |
| 312 | HPV34/73-na-1 | UUUAACAGAGGACGACGACAAGGAA |
| 313 | HPV34/73-na-2 | AAGCCUUGCAGUAUCACGAUCCAAA |
| 314 | HPV34/73-na-3 | UGUUGCAACCUCCUCCACCCUUAGA |
| 315 | HPV34/73-na-4 | GCCUCUGGCAGACAUUUUAUUUUCAA |
| 316 | HPV34/73-na-5 | AACAGGUUAAGGUUGUAGACCCUGC |
| 317 | HPV34/73-na-6 | CAGCACAGUGACUUGCAUAAUGCUC |
| 318 | HPV34/73-na-7 | UACUAGAAGUGGCAAACGUAUAGGU |
| 319 | HPV34/73-L1-1 | AAAGGUAUACCUGCCCCCUGUGUCU |
| 320 | HPV34/73-L1-2 | AAAGUUUCAGGUUUGCAAUACAGGG |
| 321 | HPV34/73-L1-3 | CUGUUGUAGAUACUACUAGAAGCAC |
| 322 | HPV34/73-L1-4 | UUUUGGCUUCCUGCAGGCAACUUGG |
| 323 | HPV34/73-L1-5 | UGCACACACAUUUUUUACCCACCCU |
| 324 | HPV6/11-E6E7-1 | GAAAACGGUUCAACCGAAAACGGUU |
| 325 | HPV6/11-E6E7-2 | GACCAGUUGUGCAAGACGUUUAAUC |
| 326 | HPV6/11-E6E7-3 | ACUGCUGGACAACAUGCAUGGAAGA |
| 327 | HPV6/11-E6E7-4 | GACCCUGUAGGGUUACAUUGCUAUG |
| 328 | HPV6/11-E6E7-5 | AGACAGCUCAGAAGAUGAGGUGGAC |
| 329 | HPV6/11-E6E7-6 | GUUGCUGUGGAUGUGACAGCAACGU |
| 330 | HPV6/11-na-7 | CGGACGAUUCAGGUACAGAAAAUGA |
| 331 | HPV6/11-na-8 | CAUUAUGCGACUGUGCAGGACCUAA |
| 332 | HPV6/11-na-1 | ACAGCCAAAAAAGGUAAAGCGACGG |
| 333 | HPV6/11-na-2 | GAAAAUGGGGGAGAUGGUCAGGAAA |
| 334 | HPV6/11-na-3 | GAGGACGAGGAAGAUGGAAGCAAUA |
| 335 | HPV6/11-na-4 | GGCAGCACAGUUAUAUGUUCUCCUG |
| 336 | HPV6/11-na-5 | CUACUACAUACACCCCCGCACAGAC |
| 337 | HPV6/11-na-6 | CUAUGGGAACACCCUUUAGUCCUGU |
| 338 | HPV6/11-L1-7 | ACGCCGUAAACGUAUUCCCUUAUUU |
| 339 | HPV6/11-L1-1 | UAGCGACAGCACAGUAUAUGUGCCU |
| 340 | HPV6/11-L1-2 | CAGGCUUUGGUGCUAUGAAUUUUGC |
| 341 | HPV6/11-L1-3 | CUGUGGUAGAUACCACACGCAGUAC |
| 342 | HPV6/11-L1-4 | GAGUAACCUAAGGUCACACACCUGC |
| 343 | HPV6/11-L1-5 | CCACACCCUACAUAUUUCCUUCUUA |

B. Design of the Immobilization and Detection Probe

To design the immobilization and detection probes, all available HPV genomic sequences were aligned. From these alignments, the most closely related subgroups of HPV types according to phylogenetic tree classification were selected. These closely related HPV subgroups were re-aligned in smaller groups for full length, E6/E7 and L1 regions. Specific oligonucleotide probes for each HPV type were extracted from the nonconsensus regions of the realigned sequences. Probes were selected having 25 to 32 bp and a $T_m$ from 55° C. to 70° C. The probes were then compared against other HPV types present in the NCBI Database using a BLAST search to confirm their uniqueness for each specific HPV type. Multiple probes were designed for each HPV type. A complete list of the probes generated according to this method is found in Table 2 (below). To protect against deletion or mutation causing a false positive in the assay, one probe each for the E6/E7 and L1 regions of the HPV genome was developed. This is especially helpful for integrated targets, as some regions can become disrupted during integration.

The immobilization probes are modified so as to facilitate binding to the detection beads. In the following examples, Luminex® microspheres are utilized as the detection bead, which are coated with carboxy groups to facilitate immobilization of capture probes. Therefore, the immobilization probes all contain a 5'Amino-C12 modification In the following examples, SA-PE is used to detect captured nucleic acids. Accordingly, all of the detection probes in the following examples have a 5' Biotin modification to facilitate detection by SA-PE.

TABLE 2

E6/E7 SPECIFIC IMMOBILIZATION/DETECTION PROBES.

| HPV TYPE | PROBE ID | SEQ ID NO | PROBE SEQUENCE |
|---|---|---|---|
| HPV 2 | E6_-2A | 344 | TGTATGGTGCAAACGGCCGTTATCAGAG |
|  | E6_-2B | 345 | ACATTGCATGAACTGCGGGTCATC |
| HPV 3 | E6_-3A | 346 | TCTACTGTGCAGAAACACCGGAATAGGA |
|  | E6_-3B | 347 | TACGAAACAGCTGACTACAACTGAACTACAA |
|  | E6_-3C | 348 | TCTGGTCATTGGAGGGGAGCTGTCAGTAC |
|  | E6_-3D | 349 | CAGCTGACTACAACTGAACTACAAGC |
| HPV 6 | E6_-6A | 350 | GGCTATCCATATGCAGCCTGCGCGTGC |
|  | E6_-6B | 351 | CAAGACATCTTAGACGTGCTAATTCGG |
|  | E6_-6C | 352 | CAAGACATTTTAGACGTGCTAATTCGG |
|  | E6_-6D | 353 | GGTAAAACATATACTAACCAAGGCGCGG |
|  | E6_-6E | 354 | GGTAAAACATATACTAACCAAGGCACGG |
| HPV 7 | E6_-7A | 355 | ACAGCTAGAACTTTATTTGAATTATGTG |
|  | E6_-7B | 356 | TAACAGCATTTTACAAACAGCTGAGGTGCTG |
|  | E6_-7C | 357 | AGCGTGTGTAAAGTGTTTAGAATTTTAT |
| HPV 10 | E6_-10A | 358 | TGCAGAAGCTATGTCCATGGGTGCACAGGA |
|  | E6_-10B | 359 | GCTTTTGTGTAGAAATTGTGGAATACCTTTG |
|  | E6_-10C | 360 | GGCAGCATTTGCACTTAGAGAATTAT |
| HPV 11 | E6_-11A | 361 | GTGTGCCTGTTGCTTAGAACTGCAAGGG |
|  | E6_-11B | 362 | ACTAAAGCACATATTGGGAAAGGCACGC |
|  | E6_-11C | 363 | GAGTGCACAGACGGAGACATCAGACAACTAC |
| HPV 16 | E6_-16A | 364 | CAGACATTTTATGCACCAAAAAGAACT |
|  | E6_-16B | 365 | AGTTTGTATGGAACAACATTAGAACAGCAAT |
|  | E6_-16C | 366 | CATAAAGTTACCAGATTTATGCACAGAGC |
|  | E6_-16D | 367 | CGATGTATGTCTTGTTGCAGATCATCA |
| HPV 18 | E6_-18A | 368 | GCTACCTGATCTGTGCACGGAACTGAACA |
|  | E6_-18B | 369 | GCAAGACAGTATTGGAACTTACAG |
|  | E6_-18C | 370 | CCGAGCACGACAGGAACGACTCCAACGAGC |
| HPV 26 | E6_-26A | 371 | AGAGAACGACCCAGAACGCTACATGAGC |
|  | E6_-26B | 372 | TGCAATTTGTGACCTAAGAGTAGTATATAGAG |
|  | E6_-26C | 373 | ACGTTCGAGTGCTGGAGCAGATGTTAATGGAA |
|  | E6_-26D | 374 | TCCTTGGTGTGCCATCAGTGTGCTGCACAGT |

TABLE 2-continued

E6/E7 SPECIFIC IMMOBILIZATION/DETECTION PROBES.

| HPV TYPE | PROBE ID | SEQ ID NO | PROBE SEQUENCE |
|---|---|---|---|
| HPV 27b | E6_-27A | 375 | ACACTGCATGCAGTGCGGGTCAAC |
|  | E6_-27B | 376 | GCGTGTATTGCAGACGAGCGCTTTCAGAC |
|  | E6_-27C | 377 | GCGTGTATTGCAGACGAGCGCTTTCAGAC |
|  | E6_-27D | 378 | AGCGCTTTCAGACGCTGATGTATT |
|  | E6_-27E | 379 | AGCGCTTTCAGACGCTGATGTATT |
| HPV 28 | E6_-28A | 380 | GCACTGCATATTCTGCGCCAAAGTGC |
|  | E6_-28B | 381 | GCCAAAGTGCTGACCACAGCGGAGCTAT |
|  | E6_-28C | 382 | ACTGCAGGGCATTGTGCGACGCCTGAAGCAC |
|  | E6_-28D | 383 | TGCATAGCTGGCTACTGGAGAGGGAGCTGTC |
| HPV 29 | E6_-29A | 384 | CAGCCCAGAACTGGCAGCATTTTGC |
|  | E6_-29B | 385 | CGCTGCTTATTGTTTGAAGGCATAAAGC |
|  | E6_-29C | 386 | GTGCCACAAGCCACTTGTCAGAGAGG |
|  | E6_-29D | 387 | CAAAATTTCTGGATACTGGAGAGGGAGTTGC |
| HPV 30 | E6_-30A | 388 | GCACCATCTTTGTGAGGTACAAGAAACATCG |
|  | E6_-30B | 389 | CAAGAAGGAATTATCCAGCTCAGAGG |
|  | E6_-30C | 390 | GACTGGTATATAGGGAGGACAGCCCA |
|  | E6_-30D | 391 | CACAACGTCCACTGAGACAGCAGTATAAT |
|  | E6_30-E | 392 | CTGCGTGCCCTACAACAGATGCTTATGGGC |
| HPV 31 | E6_31A | 393 | CTACTGCAAAGGTCAGTTAACAGAAA |
|  | E6_31B | 394 | CTACTGCAAAGGTCAGTTAACAGAAACA |
|  | E6_31C | 395 | TTGACAAACAAAGGTATATGTGATTTG |
|  | E6_31D | 396 | AAAAAGAAACGATTCCACAACATAGG |
| HPV 32 | E6_-32A | 397 | ACCACTTAACCAGTGCTGAAGCGTATGCA |
|  | E6_-32B | 398 | GCATACAGTAGAACAAGAAACAGGACTACTG |
|  | E6_-32C | 399 | CCTGCCAACGTGTGACCCGACAACGTGC |
|  | E6_-32D | 400 | GCCAGTGTAGTAACCGGGGAAACACC |
| HPV 33 | E6_-33A | 401 | CTGTGTTTGCGGTTCTTATCTAAAATTAGTG |
|  | E6_-33B | 402 | CACAACATTGAACTACAGTGCGTGGAATGC |
|  | E6_-33C | 403 | ATTATTCTGTATATGGACATACATTAGAACA |
|  | E6_-33D | 404 | ATTATTCTGTATATGGAAATACATTAGAACA |
|  | E6_-33E | 405 | TGTAAAAACGCCATGAGAGGACACAAGCC |
|  | E6_-33F | 406 | ACACAACATTGAACTACAGTGCGTGGA |

TABLE 2-continued

E6/E7 SPECIFIC IMMOBILIZATION/DETECTION PROBES.

| HPV TYPE | PROBE ID | SEQ ID NO | PROBE SEQUENCE |
|---|---|---|---|
|  | E6_-33G | 407 | ACACCACATTGAACTACAGTGCGTGGA |
|  | E6_-33H | 408 | ATTATTCGCTATATGGAGAAACATTAGAACA |
|  | E6_-33I | 409 | CAGGATATAAATCTAAAACATATTC |
|  | E6_-33J | 410 | CAGGATGTAAATCTAAAATATATTC |
|  | E6_-33K | 411 | ATCTGCAAATGCAAAATCATATACCTCAG |
|  | E6_-33L | 412 | ATCTGCAAATACAAAGTCATATACCTCAG |
| HPV 34 | E6_-34/64A | 413 | CAGCCTTATGTGAAGAGGTCAACATTTCA |
|  | E6_-34/64B | 414 | GCAGGACATTGTGTTAGATCTGAAACCAACG |
|  | E6_-34/64C | 415 | CACACGCTGACCTATTAGTGTTAGAAGACC |
| HPV 35 | E6_-35A | 416 | AGAAGGCCAGCCATATGGAGTATGCATG |
|  | E6_-35B | 417 | GAAGAAAAAAAACGATTCCATAACATCGG |
|  | E6_-35C | 418 | ACAGAGCACACATTGACATACGTAAATTGG |
| HPV 39 | E6_-39A | 419 | TGCAGACGACCACTACAGCAAACCGAGG |
|  | E6_-39B | 420 | GCAGACGACCACTACAGCAAACCGAGG |
|  | E6_-39C | 421 | CCAGCAGAAAAATTAAGACACCTAAATAGC |
|  | E6_-39D | 422 | AAGAGAAACCCAAGTATAACATCAGATATGCG |
|  | E6_-39E | 423 | CTAACACGAAGAGAAACCCAAGTATAACATC |
| HPV 40 | E6_-40A | 424 | CAGGCCAGGACCCTGTATGAACTGTGTG |
|  | E6_-40B | 425 | AAGACGGTCCTAAAAACAGCTGAGGTACTG |
|  | E6_-40C | 426 | CGCATGTCCACGGTGCCTGGACCTGCAC |
| HPV 42 | E6_-42A | 427 | GCACTTAACAGGCGCAGAGGTGCTCGCG |
|  | E6_-42B | 428 | GTATACAGTGGAGAAAGAAACTGGACTACTT |
|  | E6_-42C | 429 | GTACAGCAGACACAGGTAGAACACGGAC |
| HPV 43 | E6_-43A | 430 | CTTTGACTACGCAGCATATGCAGATACTGT |
|  | E6_-43B | 431 | CAGTGTTTGATTTGTGCATTAGATGC |
|  | E6_-43C | 432 | ATCACCAGTGGAAAAAGTACAGCATA |
|  | E6_-43D | 433 | GCACATCCTGTCTGTGTGTAATTCGAC |
| HPV 44 | E6_-44A | 434 | GAAAAACGTTAAGTACTGCAGAGGTTT |
|  | E6_-44B | 435 | TAAGTCAATTCTGGACGTGCTGATACG |
|  | E6_-44C | 436 | CCACCTGTGGTACATGTAGTCGGAAGG |
| HPV 45 | E6_-45A | 437 | GCATTACAGGATGGCGCGCTT |
|  | E6_-45B | 438 | CCATTGAACCCAGCAGAAAAACG |
|  | E6_-45C | 439 | GTAGAGAGCTCGGCAGAGGACCTTAGAACAC |
| HPV 51 | E6_-51A | 440 | GAAGCTTTGAACGTTTCTATGCACAATATA |
|  | E6_-51C | 441 | CAAAAATTAGAGAGTATAGACGTTATAGCAGG |
|  | E6_-51D | 442 | ATGCGCTAATTGCTGGCAACGTACACGAC |
| HPV 52 | E6_-52A | 443 | GAGGATCCAGCAACACGACCCCGGACCC |
|  | E6_-52B | 444 | GGCTGCAGTGTGTGCAGTGCAAAAAGAGC |
|  | E6_-52C | 445 | CCATATGGCGTGTGTATTATGTGCCTACGC |
|  | E6_-52D | 446 | GATGAGGAGGATACAGATGGTGTGGACCG |
|  | E6_-52E | 447 | GAGGATCCAGCGACACGACCCCGG |
|  | E6_-52F | 448 | AGGCTGCAGTGTGTGCAGTGCAAAAAGAGC |
|  | E6_-52G | 449 | AGGCTGCAGTGTGTGCAGTGTAAAAAGAGC |
|  | E6_-52H | 450 | TGTGCAGTGCAAAAAAGAGCTACAACGAAGA |
|  | E6_-52I | 451 | GGAAAACATTAGAAGAGAGGGTAAAAAAACCA |
|  | E6_-52J | 452 | GGAAAACATTAGAAGAGAGGGTAAGAAAACCA |
|  | E6_-52K | 453 | GGAAAACATTAGAAGAGAGGGTAAAAAGACCA |
|  | E6_-52L | 454 | GGAAAACATTAGAAGAGAGGTTAAAAAAACCA |
|  | E6_-52M | 455 | GGAAAACATTAGAAGAGAGGGTCGAAAAACCA |
| HPV 53 | E6_-53A | 456 | TATATAATTTTGCATATACAGATCTAAGAG |
|  | E6_-53B | 457 | GCAAGAAGGCATTGACAGCGTCAGAGG |
|  | E6_-53C | 458 | GTATAGAGACGGGTATCCGTATGG |
|  | E6_-53D | 459 | ATGGTATAGAGACGGGTATCCGTATGG |
| HPV 54 | E6_-54A | 460 | GGGGGCAATGTCTGCTACTGAACCCCAC |
|  | E6_-54B | 461 | GCCTTTTGCAAGAAGACGGTGTGTACA |
|  | E6_-54C | 462 | GCTTGTGCACTGTGCCTAGAACTGCACGGGC |
|  | E6_-54D | 463 | ACGGCTATGTGTGTATAGCACGCACACAGG |
|  | E6_-54E | 464 | GGGGGCAATGTCTGCTACTGAAC |
|  | E6_-54F | 465 | GACGGTGTGTACAGCAGATATTTATGCA |

TABLE 2-continued

E6/E7 SPECIFIC IMMOBILIZATION/DETECTION PROBES.

| HPV TYPE | PROBE ID | SEQ ID NO | PROBE SEQUENCE |
|---|---|---|---|
| HPV 55 | E6_-55A | 466 | TAAATTACAGAATACCTGGAAGGGTCG |
|  | E6_-55B | 467 | CCACCTGTGGTACATGTAACCGGAACG |
| HPV 56 | E6_-56A | 468 | TTGCAAAAAGAACTAACACGTGCTGAGG |
|  | E6_-56B | 469 | AGTGTATAGGGATGATTTTCCTTATGC |
|  | E6_-56C | 470 | AACATCTAGAGAACCTAGAGAATCTA |
|  | E6_-56D | 471 | GAACTAACACGTGCTGAGGTATATAAT |
| HPV 58 | E6_-58A | 472 | GCAATAAACACCATCTGCAATGGATGACC |
|  | E6_-58B | 473 | CCTGTAACAACGCCATGAGAGGAAACAACCCAACGC |
| HPV 59 | E6_-59A | 474 | GTATGCAGCGTGTCTGAAATGCATTTCA |
|  | E6_-59B | 475 | GAACATTAGAGGCTGAAACCAAGACACC |
|  | E6_-59C | 476 | CATGAGCTGCTGATACGCTGTTATAGA |
|  | E6_-59D | 477 | CTTGTGTGCTACGAGCAATTACCTGACTCCGA |
|  | E6_-59E | 478 | AACATTAGAGGCTGAAACCAAGACACC |
| HPV 61 | E6_-61A | 479 | CCGTAGGGTCAGCAAAGCACACTCATCTAT |
|  | E6_-61B | 480 | GCAGCAAACCGTTAAGTATACAGG |
|  | E6_-61C | 481 | AGCAAACCGTTAAGTATACAGGAAAAGGAGC |
|  | E6_-61D | 482 | GCTACATGAACTACTGCTGGGCGACTTGTCC |
| HPV 62 | E6_-62A | 483 | TGTGGACCTGGACGACCTGCACCTA |
|  | E6_-62B | 484 | ACGGCGGTGGCAGCACTCATGCTTT |
|  | E6_-62C | 485 | GGAAAAGGAGTATCAGGTAGAGAGGGG |
| HPV 66 | E6_-66A | 486 | GATTCCATATTCAGCAATACACAGGAA |
|  | E6_-66B | 487 | GATCCCATATTCAGCAATACACAGGAA |
|  | E6_-66C | 488 | CAAAAAGGAACTTACAAGTTTAGAGC |
|  | E6_-66D | 489 | AGTATATAGAAACAATTGGCCATATGC |
|  | E6_-66E | 490 | CCGGAGTATGGGCAACATTAGAAAGTA |
|  | E6_-66F | 491 | GTATGGGCAACATTAGAAAGTA |
|  | E6_-66G | 492 | TATATAGAAACAATTGGCCATATGC |
|  | E6_-66H | 493 | ATTAGTATATAGAAACAATTGGCCATATGCAG |
| HPV 67 | E6_-67A | 494 | CGGTAAATATATAAAGCACACCAGTGTCCA |
|  | E6_-67B | 495 | CAGTGCAAGAAATATGTTTCAGGACACAGA |
|  | E6_-67C | 496 | AAGTTTGCCCTGCGTGCAGTGCAAAAAA |
|  | E6_-67D | 497 | CATTCACAGTACAGCAGCAGACGTCCGAAC |

TABLE 2-continued

E6/E7 SPECIFIC IMMOBILIZATION/DETECTION PROBES.

| HPV TYPE | PROBE ID | SEQ ID NO | PROBE SEQUENCE |
|---|---|---|---|
| HPV 68 | E6_-68A | 498 | GCAGAAGGCAACTACAACGGACAGAGG |
|  | E6_-68B | 499 | TCAAGAAACACAAGTTTAAGTAACTATGCA |
| HPV 69 | E6_-69A | 500 | CGTCCGAGCGGTGGAGCAGCTGCTGATGGC |
|  | E6_-69B | 501 | GAGTTTGGTGTGCCACCAGTGTGCTACATAC |
|  | E6_-69C | 502 | GAGTTTGGTGTGCCACCAGTGTG |
|  | E6_-69D | 503 | ACGTCCGAGCGGTGGAGCAGCTGCTG |
| HPV 70 | E6_-70A | 504 | CCCATACGGAATGGCGCGATTTCCCAAT |
|  | E6_-70B | 505 | ATAGTATATAGAAACGGGGAGCCATATGC |
|  | E6_-70C | 506 | ATAAATATAAATATGCATGGACCACGGCCG |
|  | E6_-70D | 507 | CTCACAAGAGAACCTGCGATCTCTACT |
|  | E6_-70E | 508 | ACAAGTATAAATATAAATATGCATGGACCACG |
| HPV 71 | E6_-71A | 509 | GTTTGCTGCATGTGCCTGCTGTTTGGAAAT |
|  | E6_-71B | 510 | TAGACACCGGAACGCCAGTTACAGAGCAAC |
|  | E6_-71C | 511 | AGAAAGAATAATTACAGAAGGCAGGCG |
| HPV 72 | E6_-72A | 512 | ACGATACTGGACGTATTCGGGCTACGG |
|  | E6_-72B | 513 | GTCAGGAAAAGGAATATCAGGTGCAGACAGG |
|  | E6_-72C | 514 | ATGAGAGGGACGGTGTTGGTGTGCAG |
| HPV 73 | E6_-73A | 515 | AACCTGGACTGTGTGTTTTGCCAACGTGG |
|  | E6_-73B | 516 | GTATAGGCGATATAGACAATCAGTATATGGCA |
|  | E6_-73C | 517 | ACTTTAGACCTGAAACCAACAACCGAAAT |
|  | E6_-73D | 518 | ACAAAGCTGATTTAAGAGTGATAGAAGAGT |
| HPV 74 | E6_-74A | 519 | CCATTTGCAGCGTGCGCCATTTGCTTA |
|  | E6_-74B | 520 | AAACTAGGCGACACCTGGAAAGGGCGCTGC |
|  | E6_-74C | 521 | GTGCAGTGTACAGGACCAGACATCAACAAT |
| HPV 81 | E6_-81A | 522 | GCTGGGGCCAGCAAATCCTACCAATTTGTTT |
|  | E6_-81B | 523 | CGCAGCGTGCTTGTGCAGAGAAGCTAAAGTAC |
|  | E6_-81C | 524 | GCGGCGGTGGCAATATTCGTGCTTCGGACCA |

TABLE 2-continued

E6/E7 SPECIFIC IMMOBILIZATION/DETECTION PROBES.

| HPV TYPE | PROBE ID | SEQ ID NO | PROBE SEQUENCE |
|---|---|---|---|
| HPV 82 | E6_-82A | 525 | CCACAAGTAAAGGACATAGTGTTGGAG |
| | E6_-82B | 526 | GGTGGTGGACGACAAAAAAAGGTTTCAT |
| | E6_-82C | 527 | GCCTGGTGGGCCCGTGTTGCGCGAACAACT |
| HPV 83 | E6_-83A | 528 | CCACTGGCACAGCTGTATATACGATGCCAT |
| HPV 84 | E6_-84A | 529 | TGTGCTGTGCCAGGAATACGAGGTGGAGTTCGACG |
| | E6_-84B | 530 | AGGAAGAATTAACGGAAGGCGAAGTGC |
| | E6_-84C | 531 | GTAAAGGAATTACTAATTGTTTGGAGG |
| HPV 85 | E6_-85A | 532 | CCTATGCAACACACTGGACACATCACTGC |
| | E6_-85B | 533 | GTTAGAAAAACTAACAAATAGCAATATAT |
| | E6_-85C | 534 | CTGTATTGCTATGAGGAATTAAACAACTCAG |
| | E6_-85D | 535 | GACCTATGCAACACACTGGACACATCACTGC |
| HPV 86 | E6_-86A | 536 | CTAAAGGAATTATTACTGGTCTGGAAA |
| | E6_-86B | 537 | CAAGACACAGGCGTATCATTGGCACACTT |
| | E6_-86C | 538 | CTGCATATGGTGGAATTAAATCTGCAT |
| HPV 87 | E6_-87A | 539 | TTAAGGGAATTATTGCTGGTGTGGAGA |
| | E6_-87B | 540 | GGGAATTATTGCTGGTGTGGAGATTTGG |
| | E6_-87C | 541 | GAGCATATGATACACGCGAATCTGCAC |
| HPV 89 | E6_-89A | 542 | ATATTGCACCAAGGAGCTTACAAC |
| | E6_-89B | 543 | GGCAGCTGCCCCATGGTGTATGTGCACCG |
| | E6_-89C | 544 | CGGCCGCACGCCGACCATCCAGGAT |
| | E6_-89D | 545 | CGTGTGGTGTGTGCTATCGTGCAGTTAGG |
| HPV 91 | E6_-91A | 546 | GTACGCGGCATTAGCAGTAACAGTAGAG |
| | E6_-91B | 547 | CGAGTGCACCTCTTGTTATTGTTCAATTCGT |
| | E6_-91C | 548 | GCACCTCTTGTTATTGTTCAATTCGTC |
| HPV 94 | E6_-94A | 549 | GTGCTGCGTGTTCTGCACCAAACAGC |
| | E6_-94B | 550 | CGTGTTCTGCACCAAACAGCTGACCGTAGCC |
| | E6_-94C | 551 | CAGCTGACCGTAGCCGAATTGACTGC |
| | E6_-94D | 552 | CTGGAGAGGGTGTTGTGCTTATTGCTGGACAC |

TABLE 3

L1 SPECIFIC IMMOBILIZATION/DETECTION PROBES.

| HPV TYPE | PROBE ID | SEQ ID NO | PROBE SEQUENCE |
|---|---|---|---|
| HPV 2 | L1_-2A | 553 | CGATGCTGATTTGTATGATCCAGATACCCA |
| | L1_-2B | 554 | TCAGTTCCAACTCCAGGCAGTCATGTT |
| | L1_-2C | 555 | CAAGCGCGCCGCTGTTTCGGGGACCACGC |
| | L1_-2D | 556 | TCCCTGACCTTTTGGGATGTGGATCTCAGT |
| HPV 3 | L1_-3A | 557 | CCCCAAATCTTCTAATTCCAAGATGGATATT |
| | L1_-3B | 558 | AGCAGAATGCGTCACCGGGTGATTGT |
| | L1_-3C | 559 | TCTAGAGCTTATTACTGCACCTATACAAG |
| | L1_-3D | 560 | GTTGTACATTAAAGGTGACAGTCAGAGCGGC |
| HPV 6 | L1_-6A | 561 | AACAGTGTACTAATACACCTGTACAGGC |
| | L1_-6B | 562 | TCCTATTGACATATGTGGCACTACAGT |
| | L1_-6C | 563 | TATAATTAAGGGTAGTGGAAATCGCACGT |
| | L1_-6D | 564 | GCTGCCCCTAAACGTAAGCGCGCC |
| HPV 10 | L1_-10A | 565 | GGAACCCACCTGCACAGGGCGATTGCC |
| | L1_-10B | 566 | CAACGGTGGGGGCGAGACGTTGGTA |
| | L1_-10C | 567 | TACCAATATGTGCTTGTGTGTTCCTTCT |
| | L1_-10D | 568 | GCCTCCCCTGCCACTACGTATGACGCC |
| HPV 11 | L1_-11A | 569 | TTCATCCCTGTTTGACCCCACTACACAG |
| | L1_-11B | 570 | AGTGGTGGGTATGGTGGTAATCCTGGTCAG |
| | L1_-11C | 571 | GGGTACACAATGTTCAAATACCTCTGTACAAAA |
| | L1_-11D | 572 | TGTTCCCCTTGATATTTGTGGAACTGTCTGC |
| HPV 16 | L1_-16A | 573 | AACATCCAGACTACTTGCAGTTGGA |
| | L1_-16B | 574 | ATTTTACAATCCAGATACACAGCGGCTG |
| | L1_-16C | 575 | AGCAAATGCAGGTGTGGATAATAGA |
| | L1_-16D | 576 | TCCCCATGTAACAATGTTGCAGTAAATCCA |
| HPV 18 | L1_-18A | 577 | GCAGGTGGTGGCAATAAGCAGGATA |
| | L1_-18B | 578 | GGCCTGTGCTGGAGTGGAAATTGGC |
| | L1_-18C | 579 | CCATGCCGCCACGTCTAATGTTTCTG |
| | L1_-18D | 580 | GTCTCCTGTACCTGGGCAATATGATG |

TABLE 3-continued

L1 SPECIFIC IMMOBILIZATION/DETECTION PROBES.

| HPV TYPE | PROBE ID | SEQ ID NO | PROBE SEQUENCE |
|---|---|---|---|
| HPV 26 | L1_-26A | 581 | CCTGCAATAGTTGTGCATGGGATA |
| | L1_-26B | 582 | TGGCCAAAAGGCCGAAATTCCTAAG |
| | L1_-26C | 583 | GACACTGACAACAGGGACAATGTTTCA |
| | L1_-26D | 584 | GGAGCCCCCTACATCTTCTATTTAT |
| | L1_-26E | 585 | AAACCTGCAATAGTTGTGCATGGGATA |
| | L1_-26F | 586 | GGCGGGGGCTGTTGGGGATGCTATA |
| | L1_-26G | 587 | GGGGGCTGTTGGGGATGCTATA |
| | L1_-26H | 588 | ACTGGCCAAAAGGCCGAAATTCCTAAG |
| | L1_-26I | 589 | ATTAAAGGTGCTGAATCAGGCAGGGAGCCC |
| | L1_-26J | 590 | TAAGGCGGGGGCTGTTGGGGATGCTATACCCACCAC |
| | L1_-26K | 591 | CACTAACTTACCTGCAATAGTTGTGCATGGGATA |
| HPV 27 | L1_-27A | 592 | AAAACGCACCGCTGTTGCGGGGCGGCGG |
| | L1_-27B | 593 | AGCTGAGGTGTCTGATAATACTAATTATAAA |
| | L1_-27C | 594 | ACTATCTCGGACCCCGGCAGTCATGTG |
| | L1_-27D | 595 | GGTAGCAATAATAGGTTGGCAGTGCCTAAGGTG |
| HPV 28 | L1_-28A | 596 | ATCATCCACTAACAAAGCAGATGTGCCCAAA |
| | L1_-28B | 597 | GTCAAAATACACAACAGGGAGATTGCCCTCCG |
| | L1_-28C | 598 | TATTACAGGCCAATAAATCGGACGTGCCCT |
| | L1_-28D | 599 | CAGGGCAACGGGAGGGATGTGATTGGT |
| HPV 29 | L1_-29A | 600 | ACATTATTCAATTCCCAAATCCTCTGGTA |
| | L1_-29B | 601 | GGAGGTAGGTCGAGGGCAACCTCTCGGTGTC |
| | L1_-29C | 602 | CACTGTGTGTGCACGCACTAGTTCCGCTGC |
| | L1_-29D | 603 | GTTGTGTGCTACCACAGAGTCTCAACCGTTG |
| HPV 30 | L1_-30A | 604 | GCCCCTCAGGCCCCATTTGACACTACA |
| | L1_-30B | 605 | GGCTGGTAATTCCAAAACAGATGTT |
| | L1_-30C | 606 | AAATAACAGGGATCCCCCGCCAAGCTCA |
| | L1_-30D | 607 | TTCCTTACTATTTATTGTGCATGAATGTATG |
| HPV 31 | L1_-31A | 608 | CAGTGCTAGGCTGCTTACAGTAGGC |
| | L1_-31B | 609 | GACAATCCTAAAAAAATAGTTGTACCAAAGGTG |
| | L1_-31C | 610 | CCGGTGGTCCTGGCACTGATAATAGG |
| | L1_-31D | 611 | TAGTCCTTGTAGTAACAATGCTATTACCCCT |
| HPV 32 | L1_-32A | 612 | GCCATTAGATATTATGAACTCCATTAG |
| | L1_-32B | 613 | GGACATGTATATAAAAGCTTCTAATGG |
| | L1_-32C | 614 | TATCCAACTCCCAGTGGTTCTATGGTCA |
| | L1_-32D | 615 | CTGAAGACACATACAAGTCTACTAAC |
| HPV 33 | L1_-33A | 616 | GCTAAAAATTATTGGTACCCAAAGTATCA |
| | L1_-33B | 617 | AGTATCCTGGACAACCGGGTGCTGATAAT |
| | L1_-33C | 618 | CTTGGATGTAAGCCTCCAACAGGGGAA |
| | L1_-33D | 619 | CACATCCACCCGCACATCGTCTGCA |
| HPV 34/64 | L1_-34/64A | 620 | ACTAATGGGAAACGTAAGATTGCTGTA |
| | L1_-34/64B | 621 | GTGGAAACATAGCAGATAGTAGGGAG |
| | L1_-34/64C | 622 | AGGTACTGTAGGCGATGCTATTCCAGATGACT |
| | L1_-34/64D | 623 | GTCTGCACCTTCATCATCTAGTACAG |
| | L1_-34/64E | 624 | AAAGTGGAAACATAGCAGATAGTAGGGAG |
| HPV 35 | L1_-35A | 625 | CAGTTCTAGGCTATTAGCTGTGGGTCAC |
| | L1_-35B | 626 | GCAGTACCCAAGGTATCTGGTTTG |
| | L1_-35C | 627 | ATCATTTTATGATCCCTGCCTCCAGCGTT |
| | L1_-35D | 628 | AAATATGTTGGTAACTCTGGTAACTCTG |
| HPV 39 | L1_-39A | 629 | ATATAGGGTATTTCGCGTGACATTGCCC |
| | L1_-39B | 630 | AAAGGCATGCAAGCCCAATAATGTATCTA |
| | L1_-39C | 631 | ACGTGCAAACCCCGGTAGTTCTGTATACTG |
| | L1_-39D | 632 | CAGTTGGTAGACACTTACAGATACC |
| HPV 42 | L1_-42A | 633 | CAAAAAGGCCAAATAAGACATCTATCCCCAAA |
| | L1_-42B | 634 | TAATTTATATAACCCAGATACGCAGCGCA |
| | L1_-42C | 635 | ACATATGGTGGAGGCCCTGGTACAGAC |
| | L1_-42D | 636 | ACTGTCTGTAGGTAAACGAAAGGCGCTAC |

TABLE 3-continued

L1 SPECIFIC IMMOBILIZATION/DETECTION PROBES.

| HPV TYPE | PROBE ID | SEQ ID NO | PROBE SEQUENCE |
|---|---|---|---|
| HPV 45 | L1_-45A | 637 | GTACCTAATGGTGCAGGTAATAAACAGGCTG |
|  | L1_-45B | 638 | GTTTAGAGTAGCTTTACCCGATCCT |
|  | L1_-45C | 639 | TTGGGCATGTGTAGGTATGGAAATTGGT |
|  | L1_-45D | 640 | GCTCATGCAGCTACAGCTGTTATTACGC |
| HPV 51 | L1_-51A | 641 | CCAAGCATTCTATTGTTATACTAGGTGGGG |
|  | L1_-51B | 642 | CTCAACGCGTGCTGCTATTCCTAAA |
|  | L1_-51C | 643 | GTAATGGCCGTGACCCTATAGAAAG |
|  | L1_-51D | 644 | TATGTTAGTTTTTGTATGCTTGTGCACACT |
|  | L1_-51E | 645 | TTAACTATTAGCACTGCCACTGCTGC |
|  | L1_-51F | 646 | AACCTCAACGCGTGCTGCTATTCCTAAA |
|  | L1_-51G | 647 | AACCTCAACGCGTGCTGCTATTCCTAAAGTA |
| HPV 52 | L1_-52A | 648 | TATTAAAAACACCAGTAGTGGTAATGGT |
|  | L1_-52B | 649 | AATATGCTGGTAAACCTGGTATAGATAAT |
|  | L1_-52C | 650 | AACCCCTTGTAATAATAATTCAGGAA |
|  | L1_-52D | 651 | CCTACAGCTCATTAACAGTGTAATAC |
| HPV 53 | L1_-53A | 652 | ATAGCTATTCAGGATACTGCCCCGGAC |
|  | L1_-53B | 653 | CCCATTGGAACTTATCAATTCACCTATT |
|  | L1_-53C | 654 | CGTTATTGGTGAGGAAATACCTAATGAC |
|  | L1_-53D | 655 | CTTTCCGCAACCACACAGTCTATGTC |
| HPV 54 | L1_-54A | 656 | TTAAAGTACAAAAAACCAATAATAAGCAAAG |
|  | L1_-54B | 657 | CAACCTATGTACACCTAATACATTGGCT |
|  | L1_-54C | 658 | AGTGAGGTACCCCTTGATGTAGCTACCTCA |
|  | L1_-54D | 659 | TACAGCATCCACGCAGGATAGCTTTAATAA |
| HPV 56 | L1_-56A | 660 | GACTAAGGACAATACCAAAACAA |
|  | L1_-56B | 661 | GTACTGCTACAGAACAGTTAAGTAA |
|  | L1_-56C | 662 | GCCAGTGGCCACCAGCCTAGAA |
|  | L1_-56D | 663 | ACTAGGTCAAAGCCTGCTGTAG |
|  | L1_-56E | 664 | AAAATCTGCTCCTACCTCCACCTCTACAC |
|  | L1_-56F | 665 | ATCTGCTCCTACCTCCACCTCTACAC |
| HPV 57 | L1_-57A | 666 | GAGCTCTAGGCTCCTCACAGTAGGCCAT |
|  | L1_-57B | 667 | GAAAAATAGCACTAATAAGGTGTCTGTA |
|  | L1_-57C | 668 | CAACCTCTATGATCCCGACACCCAGCGTCTG |
|  | L1_-57D | 669 | TGTCAAAAGTTCTACCGTCCAGACCCCCGGT |
| HPV 58 | L1_-58A | 670 | CAGTTCCAGACTTTTGGCTGTTGGCA |
|  | L1_-58B | 671 | CAGATATCCCGCACAGCCAGGGTCT |
|  | L1_-58C | 672 | CCCGGATGACCTTTATATTAAAGGG |
|  | L1_-58D | 673 | ATTACACTAACTGCAGAGATAATGAC |
| HPV 59 | L1_-59A | 674 | AAAGGTGGTAATGGTAGACAGGATG |
|  | L1_-59B | 675 | AGCATCTGCTGTTGATACCAAAGATACACGT |
|  | L1_-59C | 676 | GACATACGTGCCAACCCAGGCAGTTATTTA |
|  | L1_-59D | 677 | CCCATCACCAAAACGTGTTAAGCGTCGCAAG |
| HPV 66 | L1_-66A | 678 | CCGTGAAATCAATCAATACCTTCGC |
|  | L1_-66B | 679 | CATTCCTACAGATTTGTATTGGAAGGGTG |
|  | L1_-66C | 680 | TAGACCCCCTAGACCCAAGGCTAGT |
|  | L1_-66D | 681 | AAAGCACATTAACTAAATATGATGCCCGTG |
| HPV 67 | L1_-67A | 682 | TATTAGTGGACATCCATTACTTAATAAG |
|  | L1_-67B | 683 | ATAATAAATACCCTAGCCAGCCTGGTA |
|  | L1_-67C | 684 | ACCTACAGATTTGTATTTTAAGGGATCT |
|  | L1_-67D | 685 | CACCTTCTTCTTCCTCTTCCTCCTCTG |
|  | L1_-67E | 686 | GGTAATTGTATGACTGTTGTGTGT |
| HPV 68 | L1_-68A | 687 | AGTGTTCCTGAGTCTACATTATATAATCCA |
|  | L1_-68B | 688 | ATAAAAATCCTAAAGACAGTAGGGAC |
|  | L1_-68C | 689 | CTTGTAGATACATACCGCTACCTACAA |
|  | L1_-68D | 690 | GGACCAATTCCCATTAGGACGCAAA |
| HPV 69 | L1_-69A | 691 | TCTGGTTCAACAGCAGAAATTCCTAAAGTG |
|  | L1_-69B | 692 | CTCTCGATTATTAACTTTGGGTCATCCC |
|  | L1_-69C | 693 | CTGCTAATGCAGACACTGATAATAGGGAC |
|  | L1_-69D | 694 | TAAAAATGCACAGTCTCAGGTACAGCGTGGC |

TABLE 3-continued

L1 SPECIFIC IMMOBILIZATION/DETECTION PROBES.

| HPV TYPE | PROBE ID | SEQ ID NO | PROBE SEQUENCE |
|---|---|---|---|
| HPV 70 | L1_-70A | 695 | GTTTGGCCTTCCGGATCCTTCCCTT |
|  | L1_-70B | 696 | GGATATACGTGAGCGTCCTGGTACTC |
|  | L1_-70C | 697 | TGCCTGCACCGAAACGGCCATACCTG |
|  | L1_-70D | 698 | GTCAGCTAAATCGTCTTCCTCAGCC |
| HPV 73 | L1_-73A | 699 | CTGGACAAAATACAGATGGTAGAGAA |
|  | L1_-73B | 700 | ACTTCACAAACTGTTAATACTGGTGAT |
|  | L1_-73C | 701 | TGGTGATACCGGTGATAAAATCCCAGATGACC |
|  | L1_-73D | 702 | GGCTAGTAGCTCTACTACAACGTATGCC |
| HPV 82 | L1_-82A | 703 | ACCAGTACACGTGCTGAAATACCTAAG |
|  | L1_-82B | 704 | CCCTTTAGATATAGCTCAGTCCGTGTGT |
|  | L1_-82C | 705 | GCATTACTATAATAGGGCCGGTGTGGTT |
|  | L1_-82D | 706 | TACTGGTACTGGCCGTGACCCTATTGG |
| HPV 84 | L1_-84A | 707 | ACTAATGTGCAATATCGTGCGGGTGATTGC |
|  | L1_-84B | 708 | TTTGGATCTCTGCACCACTACCTGT |
|  | L1_-84C | 709 | TCAGTCTTTTTACCTTAAGGGG |
|  | L1_-84D | 710 | GGGCCGCCGCCGCCAAGCCTAAGGAC |
| HPV 85 | L1_-85A | 711 | TACTTCTGTAGTTACACACGACACTAGA |
|  | L1_-85B | 712 | CTGTAAGCCCGGTGCTGTGCAAACAGGTGAC |
|  | L1_-85C | 713 | TGATAGGGCAACACCTGGAAGCTGTATT |
|  | L1_-85D | 714 | TGTGGTTGTTCCACAAAAAAGGATCCA |
| HPV 86 | L1_-86A | 715 | CCTGTTACTGTTTCCTCCAGCCCTGGAC |
|  | L1_-86B | 716 | AAACCAGGGGACTGCCCCCCATTA |
|  | L1_-86C | 717 | CTCCACAAGTTTGGAGGATACCTACCGT |
|  | L1_-86D | 718 | GGTGTTTTGGGAGGTTGACCTT |
| HPV 87 | L1_-87A | 719 | CAAGACAGGGGATTGTCCACCATTGCAA |
|  | L1_-87B | 720 | CGAAAAGTTACAGGAAAACAAGTCC |
|  | L1_-87C | 721 | CTATTTTTGAAGGGGCGTCGTCT |
|  | L1_-87D | 722 | TAACAAACCCTATTGGCTCAGCGGG |
| HPV 94 | L1_-94A | 723 | GGCCGGTGGTGACCAAAACGTTGGTAG |
|  | L1_-94B | 724 | TGTGCGTCCCTTCTGATGCCTCCACCGCC |
|  | L1_-94C | 725 | CCATCTCTGTCCGCAAACGCTCGGCGACCG |
|  | L1_-94D | 726 | GGCCGGTGGTGACCAAAACGTTGGTA |

C. Sample Purification via Hybrid Capture.

Cervical clinical swabs, liquid-based cytology samples, and urine all have been tested with the presently disclosed methods and determined to be compatible. In principle, any type of sample could be used.

A 50 µl aliquot of a sample is placed in a well of a polystyrene hybridization plate and mixed with 25 µl of alkali Denaturation Agent (DNR) available from Qiagen Gaithersburg, Inc. (Gaithersburg, Md.). The plate is sealed and shaken to mix, then incubated at 57.5° C. for 15 minutes shaking at 900 rpm to denature the nucleic acids in the sample.

Following denaturation, a purification probe mix comprising each of the purification probes prepared in Example 1 in low viscosity NextGen PD is added to each reaction to a final concentration of 1 nM. The plate was shaken to neutralize. A 0.02% solid paramagnetic bead stock in YT blocker is prepared, 25 µl of which is added to each reaction. The plate is then covered with clear sealer and incubated at 57.5° C. for 30 minutes with shaking at 900 rpm.

D. Amplification.

The plate resulting from Example 1(C) is placed on magnetic rack for 2 minutes. The supernatant is decanted and the plate was then blotted with clean low lint absorbent tissue, such as Kimwipes® (Kimberly-Clark Worldwide, Inc.). The beads are washed four times by adding 120 µl of whole genome amplification (WGA) Wash Buffer (available from Qiagen Gaithersburg, Inc. (Gaithersburg, Md.)) into each well, waiting 1-2 minutes, decanting, and blotting. The wash buffer is drawn off using a small volume multichannel. 20 µl of WGA Reaction Mix (set forth in Table 3 below) is then added to each well.

TABLE 3

WGA Reaction Mix with QIAGEN REPLI-g Midi RXN Mix

| Reagents | Rxn (1X) |
|---|---|
| Tris-HCl, pH 7.5 | 50 mM |
| MgCl$_2$ | 15 mM |
| (NH$_4$)$_2$ SO$_4$ | 10 mM |
| KCl | 50 mM |
| dNTP | 4 mM total |
| Primer | 250 µM |
| REPLI-g | 0.5 µl/20 µl |

*0.50 µl REPLI-g Midi per 200 µl reaction
*dNTP and Primers should be vortexed well prior to addition to the reaction mixture.

The plate is shaken to mix, then incubated at 30° C. for 2 hours. The amplicon may be stored at −20° C. or detection may directly be undertaken.

E. Genotyping

A 5 µl aliquot of the amplicon generated in Example 1D is transferred to a new round-bottom 96 well plate and mixed with 10 µl of 0.75×DNR. The plate then is incubated at 70° C. for 30 minutes to denature any nucleic acids.

After denaturation, 5 µl of a 5 nM stock of each detection probe heated to 70° C. is added to each well and the plate is incubated for 2 minutes at 70° C. A 10 µl aliquot of 0.75× HC2-Probe diluent (available from Qiagen Gaithersburg, Inc. (Gaithersburg, Md.)) is added, then mixed on a plate shaker at 800 rpm for 1 minute at room temperature. A 5 µl aliquot of a Luminex® microsphere solution at 1000 beads/µl (5000 beads total/assay) is added to each well, then the plate incubated at 50° C. for 30 minutes with shaking at 400-450 rpm. A 10 µl aliquot of a streptavidin-phycoerythrin solution (prepared in 10% Goat Serum in 1× phosphate buffered saline containing 3% TWEEN-20) is added to each well to an SA-PE final concentration of 400 ng/well). The plate is then incubated at 50° C. for 10 minutes with shaking at 400-450 rpm. Finally, the reaction mixture is diluted by adding 150 µl $H_2O$ to each well.

Thus, each Luminex® microsphere is conjugated with two oligonucleotide probes (one each in the E6/E7 and L1 regions) which are specific to that bead's HPV type. Each bead specific for an HPV type bears a unique fluorescent label. Target detection is achieved by binding specific biotinylated probes to each captured target. SA-PE bound to the biotinylated probe and a fluorescent signal is observed after excitation of the phycoerythrin by a laser. The phycoerythrin label and the fluorescent label of each bead were then independently measured on a luminometer. Measurement of the bead label indicates the genotype of the target nucleic acid bound to each bead. Measurement of the phycoerythrin label is used to determine the relative amount of target bound to each bead. The fluorescent data is then compiled to indicate the relative amounts of each target nucleic acid present in the sample.

Example 2

Demonstration of the Effect of Hybrid Capture Sample Preparation on the Detection of HPV Nucleic Acids The following example demonstrates the inhibitory effect of human genomic DNA on detection of HPV nucleic acids using the method described at Example 1.

Figure 1B:
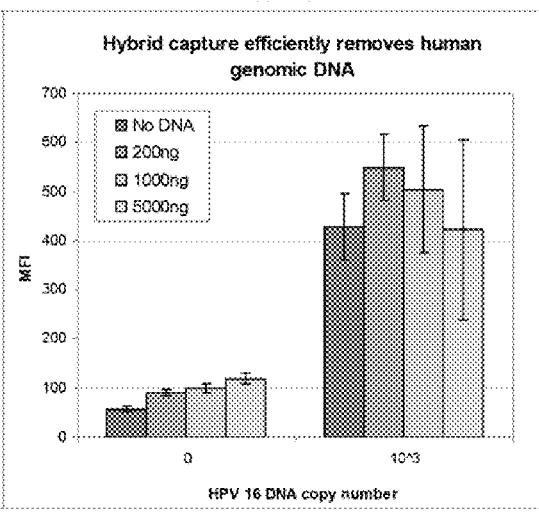
FIG. 1B is a graphical representation of hybrid capture and amplification results and how the desired target's amplification is not reduced by human genomic DNA.

An 0, $10^2$, or $10^3$ copies of a plasmid comprising the HPV 16 genome were mixed with 0, 50, 100, 200, 1000, or 5000 ng of human genomic DNA. One set of samples was subjected to hybrid capture purification, while the other was not. After hybrid capture, the samples were amplified by whole genome amplification and the presence or absence of HPV 16 was determined. Results without hybrid capture sample preparation are shown at FIG. 1A, while results with hybrid capture sample preparation are shown at FIG. 1B. As can be seen, the hybrid capture sample prep efficiently removed inhibiting DNA, enabling whole genome amplification to proceed efficiently. This demonstrates that, under conventional methods, conventional amplification of the HPV target is reduced when extraneous human genomic DNA is present, due to wasteful amplification of undesired target.

Example 3

Detection of Quadruple Infections

Samples comprising a quadruple infection were tested in a 20-plex assay as set forth Example 1, utilizing hybrid capture, immobilization, and detection probes for HPV types 6, 11, 16, 18, 31, 33, 45, 34, 35, 52, 53, 58, 59, 66, 67, 68, 69, 70, 73, and 82. The samples tested had one of the following quadruple infections: (1) HPV 6, 11, 16, 18; (2) HPV 31, 33, 45, 34; (3) HPV 35, 52, 53, 58; HPV 59, 66, 67, 68; and HPV 69, 70, 73, and 82. Results are illustrated in FIG. 2. Under the methods described above, detection of quadruple infections from $10^2$ to $10^7$ of each HPV type can be simultaneously detected in a 20-plex reaction with good specificity and sensitivity.

Example 4

Detection with Small Amplicon Volumes

Figure 3A:
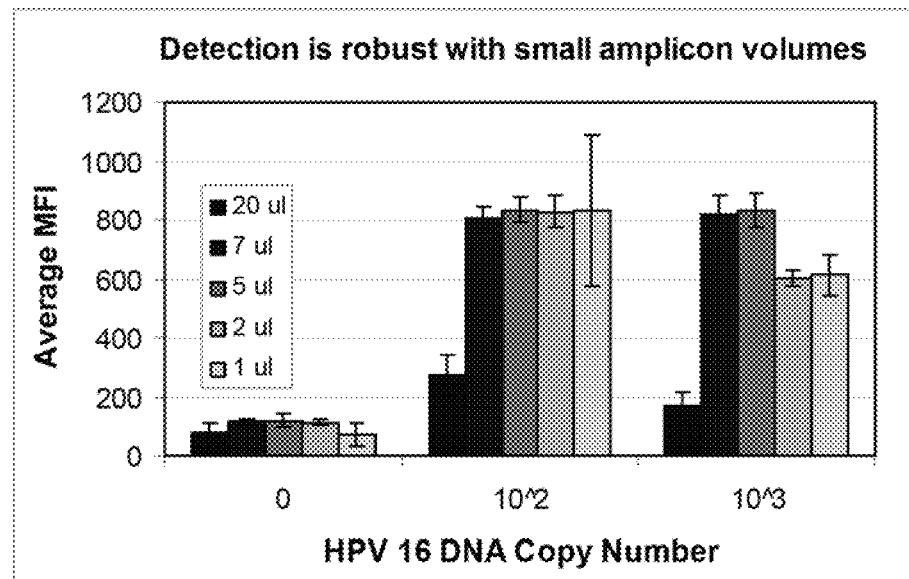
FIG. 3A is a graphical representation of target detection results at various amplicon volumes; and 3B is a graphical representation of target detection results after overnight amplification.

HPV 16 was tested for according to Example 1, except that 1, 2, 5, 7, and 20 µl of amplicon were individually used. The results are illustrated in FIG. 3A. The results show that a small amount of amplicon required for robust detection of low copy numbers. Amplification is very robust, and only a small portion of amplicon is required to saturate the detection method being used. Small volumes of amplicon gives strong signal both at low-copy amplicons, as well as high-copy ($>10^7$) amplicon.

Figure 3B:
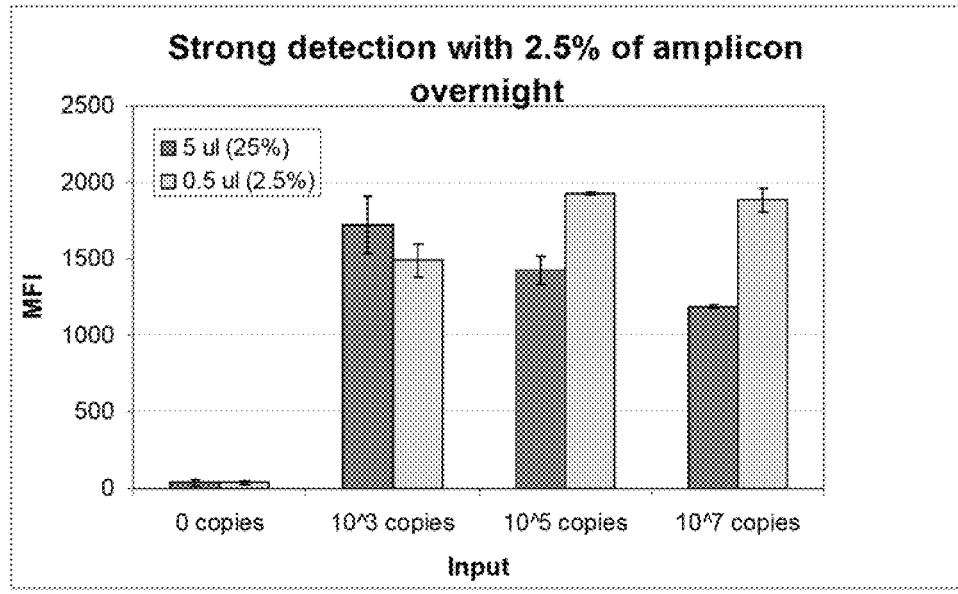

The process was repeated with 0.5 and 5 µl over night. The results are illustrated in FIG. 3B. As is evident, even smaller amounts of amplicon can be effectively used if amplification proceeds overnight.

Example 5

Specific Detection

Figure 4A:
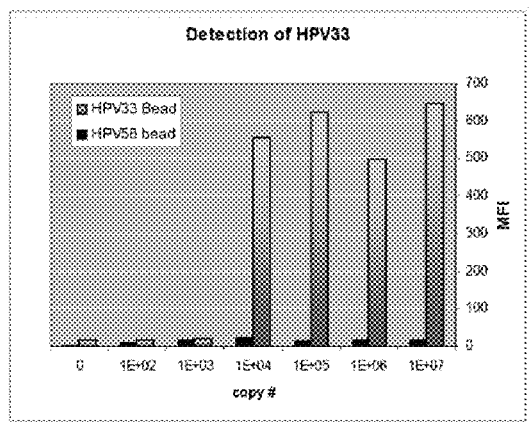
FIGS. 4A and 4B are graphical representations of target detection results for two HPV types.
Figure 4B:
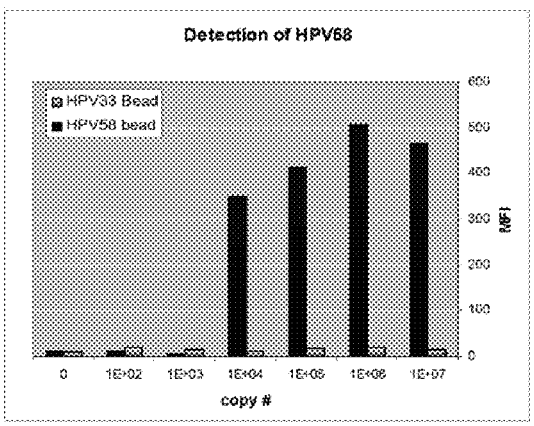

The process outlined in Example 1 was repeated for a sample containing both HPV types 33 and 58. An identical detection probe was used (consensus for HPV 33 and HPV 58), and either HPV 33 or HPV 58 capture probe was used when in the presence of both amplicons. When using the HPV 33 capture probe, only HPV 33 is detected (see FIG. 4A). When using the HPV 58 detection probe, only HPV 58 is detected (see FIG. 4B). The results for each capture probe are illustrated in FIGS. 4A and 4B. Thus, detection of the specific amplicon only occurred on the correct capture bead, regardless of the fact that the detection probe was bound to both amplicons.

Example 6

Sensitivity of Multiplex Experiments

Figure 5:
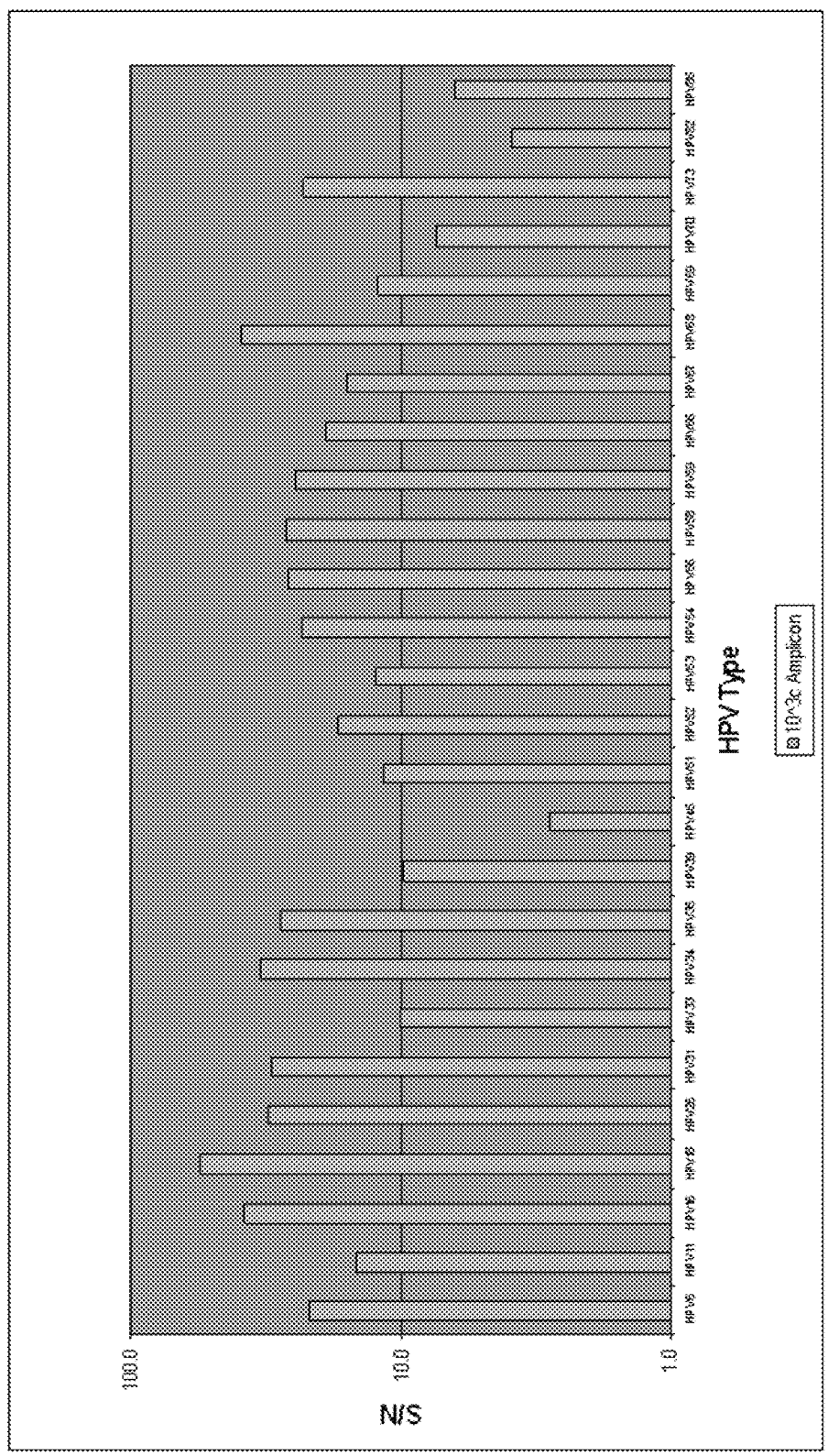
FIG. 5 is a graphical representation of multiplex experiment results testing for 26 HPV types and all HR-HPV types.

Multiplex experiments to test the sensitivity of 26 HPV types by repeating the processes outlined in Example 1 for HPV types 6, 11, 16, 18, 26, 31, 33, 34, 35, 39, 45, 51, 52, 53, 54, 56, 58, 59, 66, 67, 68, 69, 70, 73, 82, and 85. The results are demonstrated in FIG. 5. These results show assay sensitivity at 1000 copies for each of the tested types. Specifically that an S/N of greater than 2 was achieved for all 26 HPV types.

Example 7

Specificity of Multiplex Experiments

Multiplex experiments were performed to test the sensitivity of the disclosed processes for 26 HPV types by repeating the processes outlined in Example 1 for samples comprising HPV types 6, 11, 16, 18, 26, 31, 33, 34, 35, 39, 45, 51, 52, 53, 54, 56, 58, 59, 66, 67, 68, 69, 70, 73, 82, or 85. The results are demonstrated in FIG. 6. These results show that all HR-HPV types were specific against other types at up to $10^6$ copies. As can be seen, the S/N of all non-specific HPV types was less than 2.0 for each data point tested. With only one exception, the S/N of all specific HPV types was approximately 5 or greater.

Example 8

Detection of a Single HPV Infection in a Clinical Sample

Figure 7:
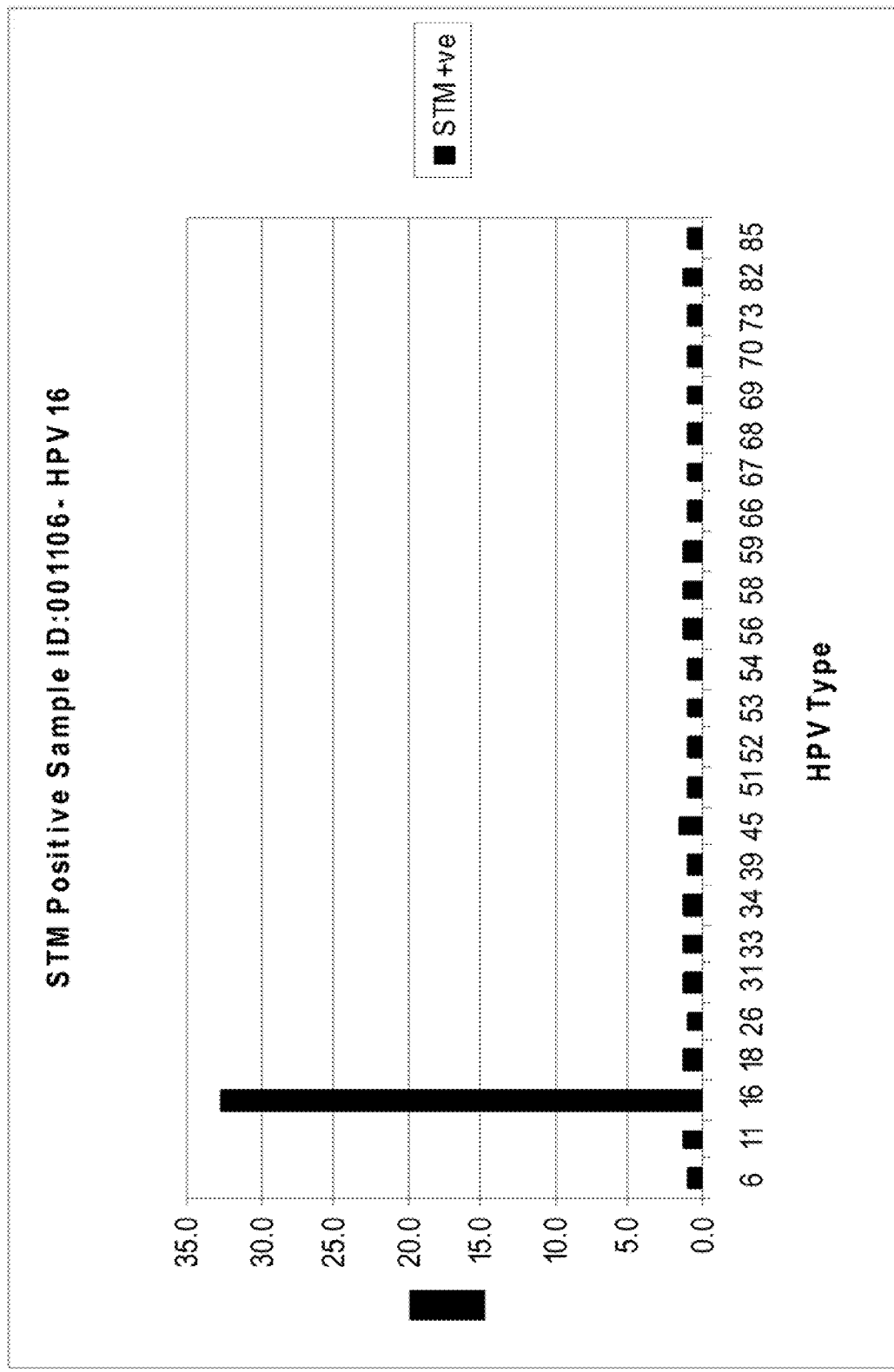
FIG. 7 is a graphical representation of detection results of a single HPV type infection.

The processes outlined in Example 1 were conducted on a clinical sample which was by a reference test shown to have an HPV type 16 infection. The results are represented in FIG. 7 and show successful detection of HPV 16.

Example 9

Detection of a Single HPV Infection in a Clinical Sample

Figure 8:
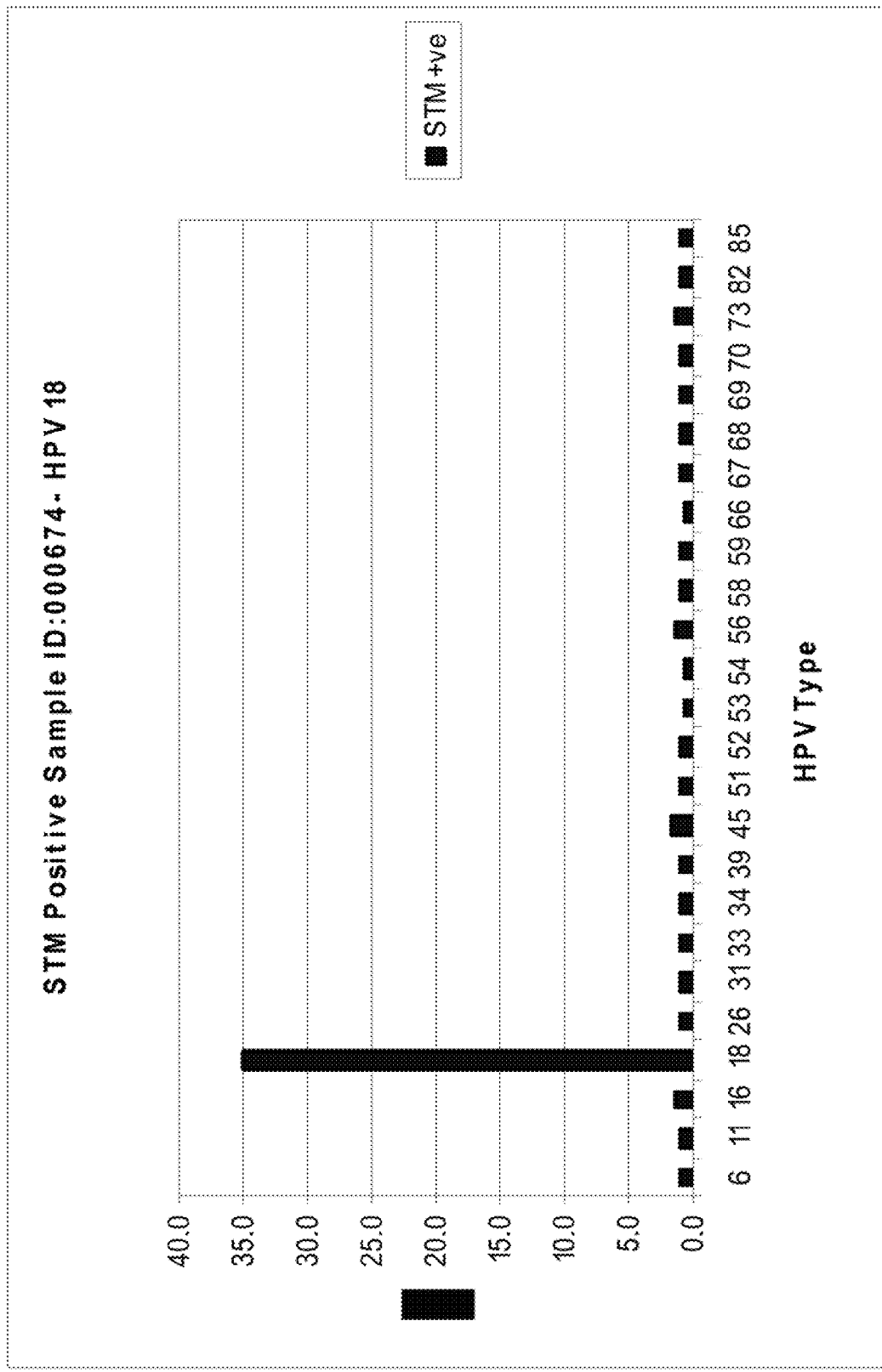
FIG. 8 is a graphical representation of detection results of a single HPV type infection.

The processes outlined in Example 1 were conducted on a clinical sample which was by a reference test shown to have an HPV type 18 infection. The results are represented in FIG. 8 and show successful detection of HPV 18.

Example 10

Detection of a Quadruple HPV Infection in a Clinical Sample

Figure 9:
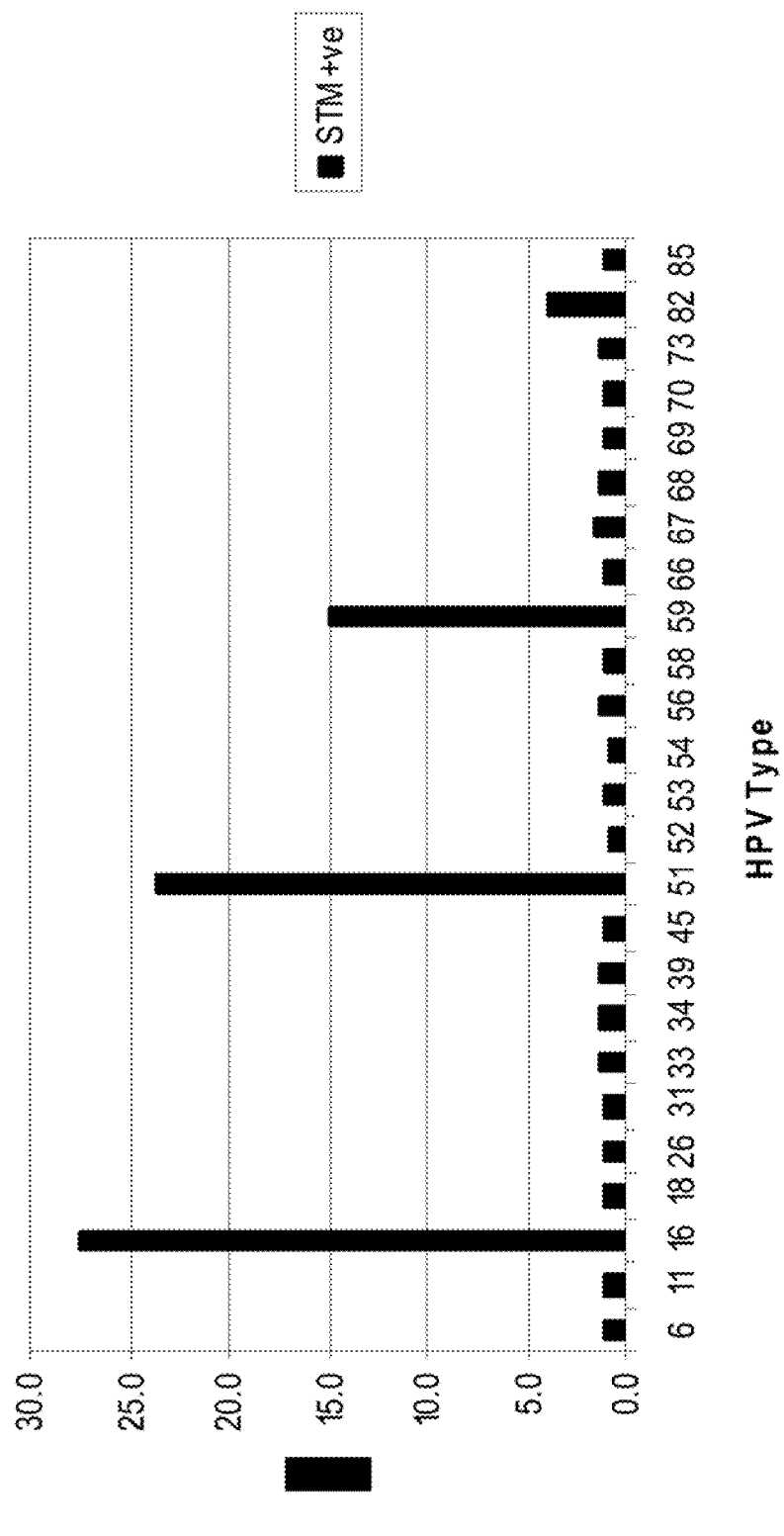
FIG. 9 is a graphical representation of detection results of a quadruple HPV type infection.

The processes outlined in Example 1 were conducted on a clinical sample which was by reference tests shown to have HPV type 16, 51, 59, and 82 infections. The results are represented in FIG. 9 and show successful detection of HPV 16, 51, 59, and 82.

Example 11

Detection of a Double HPV Infection in a Clinical Sample

Figure 10:
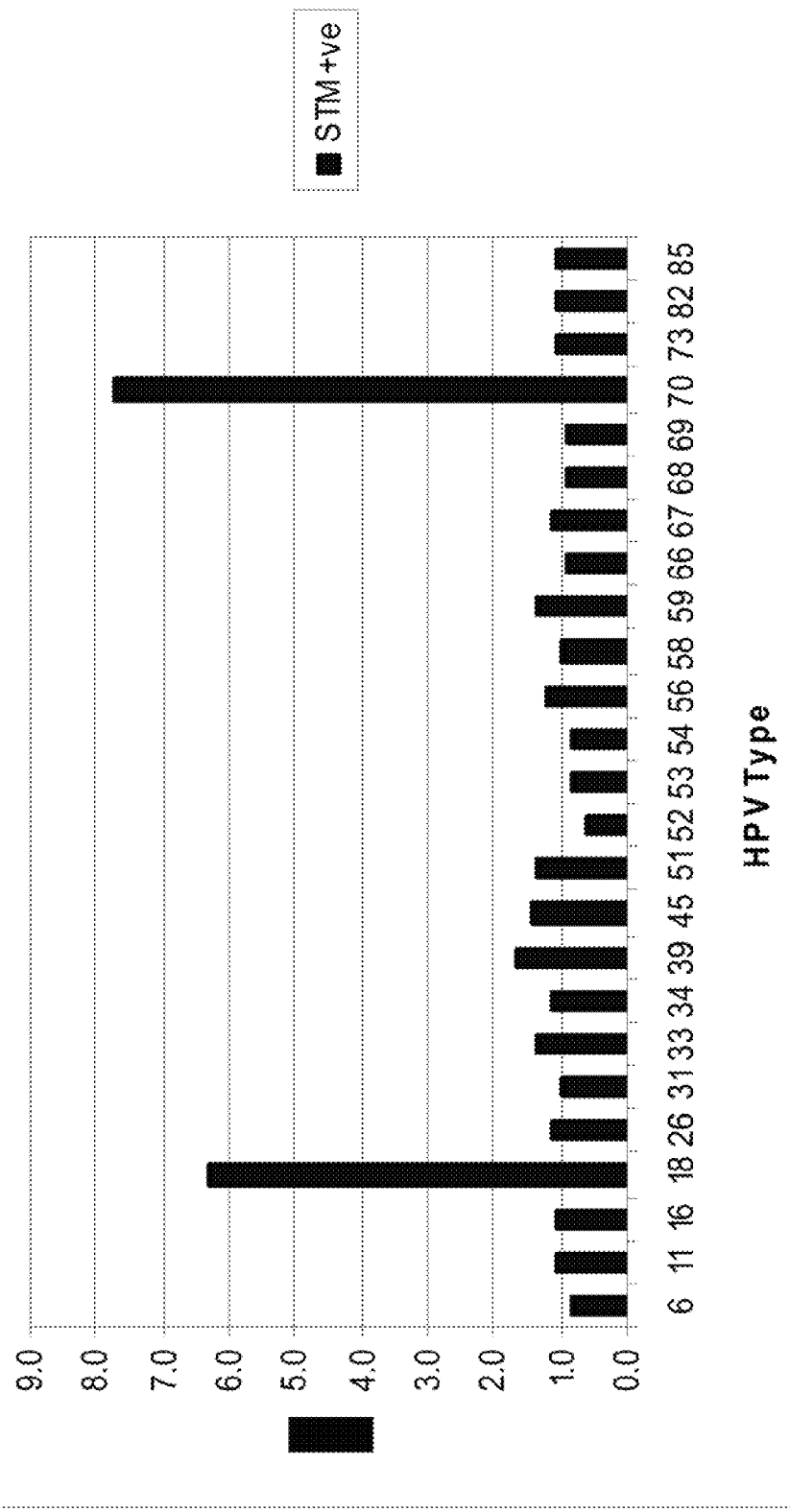
FIG. 10 is a graphical representation of detection results of a double HPV type infection.
Figure 11:
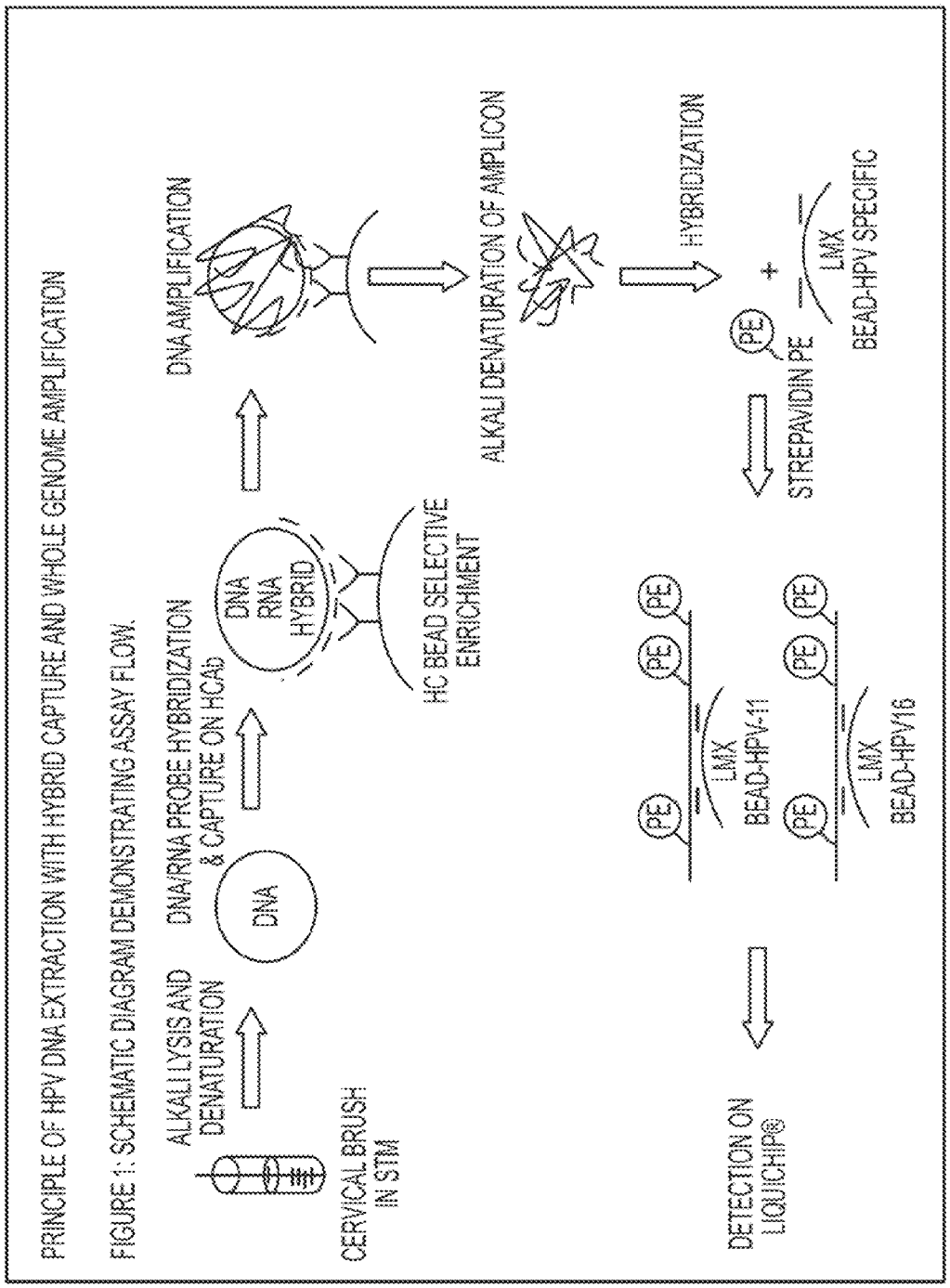
FIG. 11 is a schematic illustrating hybrid capture, whole genome amplification, and detection of the target nucleic acids.

The process outlined in Example 1 was conducted on a clinical sample which was by reference tests shown to have an HPV types 18 and 70 infections. The results are represented in FIG. 10 and show successful detection of HPV 18 and 70.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

---

What is claimed is:

1. A nucleic acid probe set consisting of:
   a) a first nucleic acid probe consisting of one of the nucleotide sequences selected from the group consisting of SEQ ID NO: 102 to SEQ ID NO: 113, and complements thereof and a detectable label, wherein said first nucleic acid probe is capable of hybridizing under selective stringency conditions to a portion of a gene selected from the group consisting of E6 and E7; and
   b) a second nucleic acid probe consisting of one of the nucleotide sequences selected from the group consisting of SEQ ID NO: 577 to SEQ ID NO: 580, wherein said second nucleic acid probe is capable of hybridizing under selective stringency conditions to a portion of an L1 gene;
   wherein the first nucleic acid probe and second nucleic acid probe are capable of hybridizing under stringent conditions to the same HPV genome, and
   wherein the nucleic acid probe set is capable of isolating HPV nucleic acids from non-HPV nucleic acids in a sample.

2. The nucleic acid probe set of claim 1, wherein the first nucleic acid probe further comprises a ligand.

3. The nucleic acid probe set of claim 1, wherein said nucleic acid probe set further comprises:
   (a) a purification probe set, wherein the probes of the purification probe set comprise at least one consensus probe capable of hybridizing to a plurality of target nucleic acids from different HPV types.

4. The nucleic acid probe set of claim 3, wherein the probe set further comprises:
   (b) an immobilization probe set comprising at least one polynucleotide probe specific for one of the plurality of target nucleic acids.

5. The nucleic acid probe set of claim 4, wherein the immobilization probe set comprises at least one probe specific for each of the plurality of target nucleic acids.

6. The nucleic acid probe set of claim 4, wherein the probe set further comprises:
   (c) a detection probe set comprising at least one polynucleotide probe specific for one of the plurality of target nucleic acids.

7. A kit for genotyping a Human Papillomavirus nucleic acid, said kit comprising:
   (a) the nucleic acid probe set according to claim 1;
   (b) a nucleic acid polymerase;
   (c) a primer;
   (d) a first solid support;
   (e) an anti-DNA:RNA hybrid antibody bound to or adapted to be bound to the first solid support; and
   (f) a detectably labeled second solid support.

* * * * *